United States Patent
Han et al.

(10) Patent No.: US 6,225,288 B1
(45) Date of Patent: May 1, 2001

(54) GAMMA-KETOACID DIPEPTIDES AS INHIBITORS OF CASPASE-3

(75) Inventors: Yongxin Han, Kirkland; Andre Giroux, Ste-Anne-de-Bellevue; Erich Grimm, Baie d'Urfe; Renee Aspiotis, Westmount; Sebastien Francoeur, Montreal; Robert Zamboni, Pointe Claire; Petpiboon Prasit, Pierreponds; Christopher Bayly, Beaconsfield; Dan McKay, Ottawa; Cameron Black, Baie d'Urfe, all of (CA)

(73) Assignee: Merk Frosst Canada & Co., Kirkland (CA)

( * ) Notice: Subject to any disclaimer, the term of this patent is extended or adjusted under 35 U.S.C. 154(b) by 0 days.

(21) Appl. No.: 09/526,840

(22) Filed: Mar. 16, 2000

Related U.S. Application Data

(60) Provisional application No. 60/124,622, filed on Mar. 16, 1999.

(51) Int. Cl.[7] .............................. C07K 5/06; A01K 38/05
(52) U.S. Cl. .......................... 514/19; 544/316; 546/247; 546/335; 548/128; 548/131; 548/187; 548/143; 548/247; 548/253; 548/267.6; 548/546; 549/58; 549/77; 549/318; 549/321; 549/501; 562/426; 562/430
(58) Field of Search ..................... 562/426, 430; 514/19

(56) References Cited

U.S. PATENT DOCUMENTS 5,834,508 * 11/1998 Ando .................................. 514/471

FOREIGN PATENT DOCUMENTS

WO98/16505 * 4/1998 (WO).

OTHER PUBLICATIONS

Nicholson, D.W., et al. Nature, vol. 376, No. 6535, pp. 37–43, 1995.

* cited by examiner

*Primary Examiner*—Robert Gerstl
(74) *Attorney, Agent, or Firm*—Raynard Yuro; Richard C. Billups; David L. Rose

(57) ABSTRACT

Compounds represented by formula I:

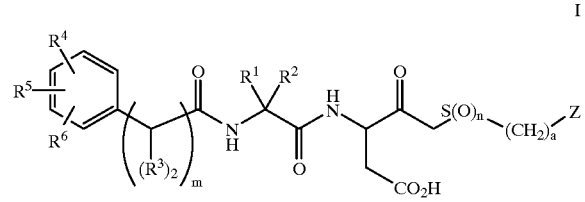

as well as pharmaceutically acceptable salts, esters and hydrates thereof are disclosed along with pharmaceutical compositions and methods of treatment. The compounds are useful as inhibitors of caspase-3, which is implicated in modulating apoptosis.

14 Claims, No Drawings

GAMMA-KETOACID DIPEPTIDES AS INHIBITORS OF CASPASE-3

CROSS REFERENCE TO RELATED APPLICATIONS

This application is a non-provisional application related to U.S. application Ser. No. 60/124,622, filed on Mar. 16, 1999 priority of which is claimed hereunder.

BACKGROUND OF THE INVENTION

Apoptotic cell suicide is a fundamentally important biological process that is required to maintain the integrity and homeostasis of multicellular organisms. Inappropriate apoptosis, however, underlies the etiology of many of the most intractable of human diseases. In only the last few years, many of the molecules that participate in a conserved biochemical pathway that mediates the highly ordered process of apoptotic cell suicide have been identified. At the heart of this pathway are a family of cysteine proteases, the 'caspases', that are related to mammalian interleukin-1β converting enzyme (ICE/caspase-1) and to CED-3, the product of a gene that is necessary for apoptotic suicide in the nematode C. elegans (Nicholson et al., 1997, Trends Biochem Sci 22:299–306). The role of these proteases in cell suicide is to disable critical homeostatic and repair processes as well as to cleave key structural components, resulting in the systematic and orderly disassembly of the dying cell.

The central importance of caspases in these processes has been demonstrated with both macromolecular and peptide-based inhibitors (which prevent apoptosis from occurring in vitro and in vivo) as well as by genetic approaches. Inhibition of apoptosis via attenuation of caspase activity should therefore be useful in the treatment of human diseases where inappropriate apoptosis is prominent or contributes to disease pathogenesis. Caspase inhibitors would thus be useful for the treatment of human diseases including, but not limited to, acute disorders such as cardiac and cerebral ischemia/reperfusion injury (e.g. stroke), spinal cord injury and organ damage during transplantation, as well as chronic disorders such as neurodegenerative diseases (e.g. Alzheimer's, polyglutamine-repeat disorders, Down's, spinal muscular atrophy, multiple sclerosis), immunodeficiency (e.g. HIV), diabetes, alopecia and aging.

Ten caspases have so far been identified in human cells. Each is synthesized as a catalytically dormant proenzyme containing an amino-terminal prodomain followed by the large and small subunits of the heterodimeric active enzyme. The subunits are excised from the proenzyme by cleavage at Asp-X junctions (Nicholson et al., 1997, Trends Biochem Sci 22:299–306). The strict requirement by caspases for Asp in the P1 position of substrates is consistent with a mechanism whereby proenzyme maturation can be either autocatalytic or performed by other caspases. The three dimensional crystal structures of mature caspase-1 and -3 show that the large subunit contains the principle components of the catalytic machinery, including the active site Cys residue which is harbored within the conserved pentapeptide motif, QACxG,1 and residues that stabilize the oxyanion of the tetrahedral transition state (Wilson et al., 1994, Nature 370:270–75; Walker et al., 1994, Cell 78:342–52; Rotonda et al., 1996, Nat Struct Biol 3:619–25). Both subunits contribute residues which stabilize the P1 Asp of substrates while the small subunit appears to contain most of the determinants that dictate substrate specificity and, in particular, those which form the specificity-determining S4 subsite. One distinctive feature of these proteases is the absolute requirement for an aspartic acid residue in the substrate P1 position. The carboxylate side chain of the substrate P1 Asp is tethered by four residues in caspase-1 (Arg179, Gln238 from p20 and Arg341, Ser347 from p10) that are absolutely conserved in all caspase family members. Catalysis involves a typical cysteine protease mechanism involving a catalytic dyad, composed of His237 and Cys285 (contained within an absolutely conserved QACxG pentapeptide) and an 'oxyanion hole' involving Gly238 and Cys285. Inhibitors bind, however, in an unexpected non-transition state configuration (which raises important considerations for inhibitor design) with the oxyanion of the thiohemiacetal being stabilized by the active site His237.

Members of the caspase family can be divided into three functional subgroups based on their substrate specificities which have been defined by a positional-scanning combinatorial substrate approach. The principle effectors of apoptosis (group II caspases, which include caspases-2,-3 and -7 as well as C. elegans CED-3) have specificity for [P4]DExD [P1], a motif found at the cleavage site of most proteins known to be cleaved during apoptosis. On the other hand, the specificity of group III caspases (caspases-6,-8,-9 and -10, as well as CTL-derived granzyme B) is [P4](I,V,L)ExD [P1] which corresponds to the activation site at the junction between the large and small subunits of other caspase proenzymes including group II (effector) family members. This and other evidence indicates that group III caspases function as upstream activators of group II caspases in a proteolytic cascade that amplifies the death signal. The role of group I caspases (caspases-1,-4 and -5) appears to be to mediate cytokine maturation and their role in apoptosis, if any, has not been substantiated.

A tetrapeptide corresponding to the substrate P4-P1 residues is sufficient for specific recognition by caspases and as a consequence has formed the basis for inhibitor design. In addition to the requirement for a P1 Asp, the P4 residue in particular appears to be most important for substrate recognition and specificity. Caspase-1, for example, prefers a hydrophobic residue such as Tyr in P4 (which corresponds to its YVHD cleavage site within proIL-1β) whereas caspase-3 (and other group II enzymes) has a preference for an anionic Asp residue (which corresponds to the DXX) cleavage sites within most polypeptides that are cleaved by these enzymes during apoptosis). Peptide aldehydes, nitriles and ketones are potent reversible inhibitors of these proteases while compounds that form thiomethylketone adducts with the active site cysteine (e.g. peptide (acyloxy) methylketones) are potent irreversible inhibitors. For example, the tetrapeptide aldehyde Ac-YVAD-CHO (which was designed to mimic the YVHD caspase-1 recognition sequence within proIL-1β) is a potent inhibitor of caspase-1 ($K_i$<1 nM) but a poor inhibitor of caspase-3 ($K_i$=12 $\mu$M) (Thornberry et al., 1992, Nature 356:768–74). In contrast, the Ac-DEVD-CHO tetrapeptide aldehyde (which was designed to mimic the caspase-3 recognition site) is a very potent inhibitor of caspase-3 ($K_i$<1 nM) although it is also a weaker but reasonable inhibitor of caspase-1, presumably owing to promiscuity in the S4 subsite of this enzyme (Nicholson et al., 1995, Nature 376:37–43).

Several features plague these peptide-derived inhibitors as a platform for drug design. In addition to their metabolic instability and membrane impermeability, the slow-binding time-dependent inhibition of activity (e.g. kon caspase-1:Ac-YVAD-CHO =3.8×105 M-1s-1; kon caspase-3:Ac-DEVD-CHO 1.3×105 M-1s-1) precludes them from the rapid inhibition characteristics that may be necessary to abolish enzymatic activity in vivo. The present patent application describes the resolution of this issue with the discovery of several novel gamma-ketoacids that make highly suitable caspase inhibitors.

SUMMARY OF THE INVENTION

Compounds represented by formula I:

I as well as pharmaceutically acceptable salts, esters and hydrates thereof are disclosed, wherein:
a is 0 or 1 and
m and n are 0,1 or 2;
Z is selected from the group consisting of:
1) $C_{1-8}$alkyl,
2) $C_{3-11}$cycloalkyl, said alkyl and cycloalkyl groups being optionally substituted with 1–4 halo groups,
3) phenyl or naphthyl, optionally substituted by one or two groups selected from the group consisting of: halo, nitro, $C_{1-4}$alkyl and $C_{1-4}$alkoxy, said alkyl and alkoxy groups being optionally substituted with 1–3 halo groups; and
4) $HET^1$ wherein $HET^1$ represents a 5 or 6 membered aromatic or non-aromatic ring, and the benzofused analogs thereof, containing from 1–3 heteroatoms selected from 0, S and N, and optionally substituted with 1–2 groups selected from halo, $C_{1-4}$alkyl and $C_{1-4}$acyl;
$R^1$ represents a member selected from the group consisting of: H, aryl,
$C_{1-6}$alkyl optionally substituted by $OR^7$, and $C_{5-7}$cycloalkyl optionally containing one heteroatom selected from O, S and $NR^8$, and
$R^2$ represents H,
or in the alternative, $R^1$ and $R^2$ are taken in combination and represent a ring of 4–7 members, said ring optionally containing one heteroatom selected from O, S and $NR^8$;
$R^7$ is selected from the group consisting of: H, $C_{1-5}$alkyl and benzyl optionally substituted with 1–2 groups selected from halo, $C_{1-4}$alkyl and $C_{1-4}$alkoxy; and
$R^8$ is H or $C_{1-4}$alkyl;
each $R^3$ is independently selected from the group consisting of: H, $C_{1-6}$alkyl optionally containing 1–2 oxo groups, $C_{1-4}$alkoxy and halo;
$R^4$, $R^5$ and $R^6$ are independently selected from the group consisting of:
1) H,
2) halo,
3) $C_{1-4}$alkoxy optionally substituted with 1–3 halo atoms,
4) $NO_2$,
5) OH,
6) benzyloxy, the benzyl portion of which is optionally substituted with 1–2 members selected from the group consisting of: halo, CN, $C_{1-4}$alkyl and $C_{1-4}$alkoxy, said alkyl and alkoxy being optionally substituted with 1–3 halo groups,
7) NH—$C_{1-4}$acyl,
8) $C_{1-4}$acyl,
9) O—$C_{1-4}$alkyl-$CO_2$H, optionally esterified with a $C_{1-6}$ alkyl or $C_{5-7}$ cycloalkyl group,
10) CH=CH—$CO_2$H,
11) $C_{0-5}$alkyl$CO_2$H,
12) $C_{0-5}$alkylC(O)$NH_2$, optionally substituted on the nitrogen atom by 1–2 $C_{1-4}$alkyl groups;
13) $C_{0-2}$alkylS(O)$_{0-2}C_{1-4}$alkyl;
14) S(O)$_{0-2}$–$C_{1-6}$ alkyl or S(O)$_{0-2}$-phenyl, said alkyl and phenyl portions thereof being optionally substituted with 1–3 members selected from the group consisting of: halo, CN, $C_{1-4}$alkyl and $C_{-4}$alkoxy, said alkyl and alkoxy being optionally substituted by 1–3 halo groups,
15) benzoyl optionally substituted by 1–2 members selected from the group consisting of: halo, CN, $C_{1-4}$alkyl and $C_{1-4}$alkoxy, said alkyl and alkoxy groups being optionally substituted by 1–3 halo groups,
16) phenyl or naphthyl, optionally substituted with 1–2 members selected from the group consisting of: halo, CN, $C_{1-4}$ alkyl and $C_{1-4}$alkoxy, said alkyl and alkoxy being optionally substituted with 1–3 halo groups,
17) CN,
18) —$C_{1-4}$alkyl-$HET^2$, wherein
$HET^2$ represents a 5–7 membered aromatic or non-aromatic ring containing 1–4 heteroatoms selected from O, S and $NR^8$ and optionally containing 1–2 oxo groups, and optionally substituted with 1–3
$C_{1-4}$ alkyl, OH, halo or $C_{1-4}$acyl groups;
19) —$OC_{0-4}$alkyl-$HET^3$, wherein $HET^3$ is a 5 or 6 membered aromatic or non-aromatic ring containing from 1 to 3 heteroatoms selected from O, S and N, and optionally substituted with one or two groups selected from halo and $C_{1-4}$alkyl, and optionally containing 1–2 oxo groups,
and
20) $HET^4$, wherein $HET^4$ is a 5 or 6 membered aromatic or non-aromatic ring, and the benzofused analogs thereof, containing from 1 to 4 heteroatoms selected from O, S and N, and is optionally substituted by one or two groups selected from halo, $C_{1-4}$alkyl and $C_{1-4}$acyl, or
$R^4$ and $R^5$ are taken in combination and represent a fused heteroaryl ring as shown below:

wherein Y is selected from the group consisting of CH and N, and X is selected from O, S and NH, and $R^6$ is as defined above.

Pharmaceutical compositions and methods of treatment are also included.

DETAILED DESCRIPTION

Compounds represented by formula I:

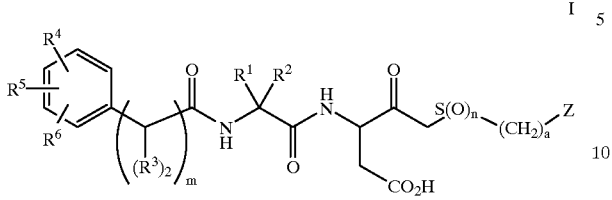

as well as pharmaceutically acceptable salts, esters and hydrates thereof are disclosed, wherein:
a is 0 or 1 and
m and n are 0, 1 or 2;
Z is selected from the group consisting of:
1) $C_{1-8}$alkyl,
2) $C_{3-11}$cycloalkyl, said alkyl and cycloalkyl groups being optionally substituted with 1–4 halo groups,
3) phenyl or naphthyl, optionally substituted by one or two groups selected from the group consisting of: halo, nitro, $C_{1-4}$alkyl and
$C_{1-4}$alkoxy, said alkyl and alkoxy groups being optionally substituted with 1–3 halo groups; and
4) $HET^1$ wherein $HET^1$ represents a 5 or 6 membered aromatic or non-aromatic ring, and the benzofused analogs thereof, containing from 1–3 heteroatoms selected from O, S and N, and optionally substituted with 1–2 groups selected from halo, $C_{1-4}$alkyl and $C_{1-4}$acyl;
$R^1$ represents a member selected from the group consisting of. H, aryl,
$C_{1-6}$alkyl optionally substituted by $OR^7$, and $C_{5-7}$cycloalkyl optionally containing one heteroatom selected from O, S and $NR^8$, and
$R^2$ represents H,
or in the alternative, $R^1$ and $R^2$ are taken in combination and represent a ring of 4–7 members, said ring optionally containing one heteroatom selected from O, S and $NR^8$;
$R^7$ is selected from the group consisting of: H, $C_{1-5}$alkyl and benzyl optionally substituted with 1–2 groups selected from halo, $C_{1-4}$alkyl and $C_{1-4}$alkoxy; and
$R^8$ is H or $C_{1-4}$alkyl;
each $R^3$ is independently selected from the group consisting of: H, $C_{1-6}$alkyl optioally containing 1–2 oxo groups, $C_{1-4}$alkoxy and halo;
$R^4$, $R^5$ and $R^6$ are independently selected from the group consisting of:
1) H,
2) halo,
3) $C_{1-4}$alkoxy optionally substituted with 1–3 halo atoms,
4) $NO_2$,
5) OH,
6) benzyloxy, the benzyl portion of which is optionally substituted with 1–2 members selected from the group consisting of: halo, CN, $C_{1-4}$alkyl and $C_{1-4}$alkoxy, said alkyl and alkoxy being optionally substituted with 1–3 halo groups,
7) NH—$C_{1-4}$acyl,
8) $C_{1-4}$acyl,
9) O—$C_{1-4}$alkyl-$CO_2$H, optionally esterified with a $C_{1-6}$ alkyl or $C_{5-7}$ cycloalkyl group,
10) CH=CH—$CO_2$H,
11) $C_{0-5}$alkyl$CO_2$H,
12) $C_{0-5}$alkylC(O)$NH_2$, optionally substituted on the nitrogen atom by 1–2 $C_{1-4}$alkyl groups;
13) $C_{0-2}$alkylS(0)$_{0-2}C_{1-4}$alkyl;
14) S(O)$_{0-2}$-$C_{1-6}$ alkyl or S(O)$_{0-2}$-phenyl, said alkyl and phenyl portions thereof being optionally substituted with 1–3 members selected from the group consisting of: halo, CN, $C_{1-4}$alkyl and $C_{1-4}$alkoxy, said alkyl and alkoxy being optionally substituted by 1–3 halo groups,
15) benzoyl optionally substituted by 1–2 members selected from the group consisting of: halo, CN, $C_{1-4}$alkyl and $C_{1-4}$ alkoxy, said alkyl and alkoxy groups being optionally substituted by 1–3 halo groups,
16) phenyl or naphthyl, optionally substituted with 1–2 members selected from the group consisting of: halo, CN, $C_{1-4}$alkyl and $C_{1-4}$alkoxy, said alkyl and alkoxy being optionally substituted with 1–3 halo groups,
17) CN,
18) —$C_{1-4}$alkyl-$HET^2$, wherein
$HET^2$ represents a 5–7 membered aromatic or non-aromatic ring containing 1–4 heteroatoms selected from O, S and $NR^8$ and optionally containing 1–2 oxo groups, and optionally substituted with 1–3 $C_{1-4}$ alkyl, OH, halo or $C_{1-4}$acyl groups;
19) —$OC_{0-4}$alkyl-$HET^3$, wherein $HET^3$ is a 5 or 6 membered aromatic or non-aromatic ring containing from 1 to 3 heteroatoms selected from O, S and N, and optionally substituted with one or two groups selected from halo and $C_{1-4}$alkyl, and optionally containing 1–2 oxo groups, and
20) $HET^4$, wherein $HET^4$ is a 5 or 6 membered aromatic or non-aromatic ring, and the benzofused analogs thereof, containing from 1 to 4 heteroatoms selected from O, S and N, and is optionally substituted by one or two groups selected from halo, $C_{1-4}$alkyl and $C_{1-4}$acyl, or
$R^4$ and $R^5$ are taken in combination and represent a fused heteroaryl ring as shown below:

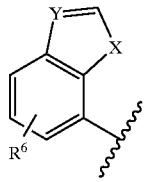

wherein Y is selected from the group consisting of CH and N, and X is selected from O, S and NH, and $R^6$ is as defined above.

The invention also encompasses a pharmaceutical composition comprising a compound of formula I in combination with a pharmacuetically acceptable carrier.

The invention also encompasses a method of treating cardiac and cerebral ischemia/reperfusion injury (e.g. stroke), type I diabetes, immune deficiency syndrome (including AIDS), cerebral and spinal cord trauma injury, organ damage during transplantation, alopecia, aging, Parkinson's disease, Alzheimer's disease, Down's syndrome, spinal muscular atrophy, multiple sclerosis and neurodegenerative disorders, comprising administering to a mammalian patient in need of such treatment an effective amount of a compound of formula I.

For purposes of this specification alkyl means linear, branched or cyclic structures and combinations thereof, containing one to twenty carbon atoms unless otherwise specified. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl-4-propylnonyl, cyclopropyl, cyclopentyl, cycloheptyl, adamantyl, cyclododecylmethyl, 2-ethyl-1-bicyclo[4.4.0]decyl and the like.

Alkylcarbonyl signifies groups having the formula—C(O)-alkyl, wherein alkyl is defined as above.

Alkylsulfonyl signifies groups having the formula—S(O)$_2$-alkyl, wherein alkyl is defined as above.

Fluoroalkyl means linear, branched or cyclic alkyl groups and combinations thereof, of one to ten carbon atoms, in which one or more hydrogen but no more than six is replaced by fluorine. Examples are —$CF_3$, —$CH_2CH_2F$, and —$CH_2CF_3$ and the like.

Alkoxy means alkoxy groups of one to ten carbon atoms of a straight, branched or cyclic configuration. Examples of alkoxy groups include methoxy, ethoxy, propoxy, isopropoxy, and the like.

Alkoxycarbonyl signifies groups having the formula—C(O)-alkoxy, wherein alkoxy is defined as above.

Alkylthio means alkylthio groups of one to ten carbon atoms of a straight, branched or cyclic configuration. Examples of alkylthio groups include methylthio, propylthio, isopropylthio, etc. By way of illustration, the propylthio group signifies —$SCH_2CH_2CH_3$.

Aryl is, for example, phenyl or naphthyl. Heteroaryl is, e.g.,, pyridyl, furyl, thienyl, thiazolyl, isothiazolyl, imidazolyl, benzimidazolyl, pyrazinyl, pyrimidyl, quinolyl, isoquinolyl, benzofuryl, benzothienyl, pyrazolyl, indolyl, purinyl, isoxazolyl, oxazolyl and coumarinyl.

Halo includes F, Cl, Br and I.

For purposes of this specification, the following abbreviations have the indicated meanings:
Alloc=allyloxycarbonyl
APCI=atmospheric pressure chemical ionization
BOC=t-butyloxycarbonyl
CBZ=carbobenzoxy
DCC=1,3-dicyclohexylcarbodiimide
DIBAL=diisobutyl aluminum hydride
DIEA=N,N-diisoproylethylamine
DMAP=4-(dimethylamino)pyridine
EDCI=1-(3-dimethylaminopropyl)-3-ethylcarbodiimide hydrochloride
EDTA=ethylenediaminetetraacetic acid, tetrasodium salt hydrate
ESI=electrospray ionization
FAB=fast atom bombardment
FMOC=9-fluorenylmethoxycarbonyl
HMPA=hexamethylphosphoramide
HATU=O-(7-Azabenzotriazol-1-yl)N,N,N',N'-tetramethyluronium hexafluorophosphate
HOBt=1-hydroxybenzotriazole
HRMS=high resolution mass spectrometry
ICl=iodine monochloride
IBCF=isobutyl chloroformate
KHMDS=potassium hexamethyldisilazane
LDA=lithium diisopropylamide
MCPBA=metachloroperbenzoic acid
Ms =methanesulfonyl=mesyl
MsO=methanesulfonate=mesylate
NBS=N-bromosuccinimide
NMM=4-methylmorpholine
PCC=pyridinium chlorochromate
PDC=pyridinium dichromate
Ph=phenyl
PPTS=pyridinium p-toluene sulfonate
pTSA=p-toluene sulfonic acid
r.t.=room temperature
rac.=racemic
TfO=trifluoromethanesulfonate=triflate
TLC=thin layer chromatography
Alkyl group abbreviations:
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl One aspect of the invention that is of particular interest relates to compounds of formula I wherein a is 1.

Another preferred aspect of the invention relates to compounds of formula I wherein m is 1.

Another preferred aspect of the invention relates to compounds of formula I wherein n is 0.

Another preferred aspect of the invention relates to compounds of formula I wherein Z is phenyl optionally substituted by one or two groups selected from halo, nitro, $C_{1-4}$alkoxy optionally substituted by up to 3 halogen atoms, or $C_{1-4}$alkyl optionally substituted by up to 3 halogen atoms.

Another preferred aspect of the invention relates to compounds of formula I wherein RI is $C_{1-5}$alkyl optionally substituted by $OR^7$. Within this subset, all other variables are as originally defined.

Another preferred aspect of the invention relates to compounds of formula I wherein R2 is hydrogen. Within this subset, all other variables are as originally defined.

Another preferred aspect of the invention relates to compounds of formula I wherein $R^3$ is hydrogen. Within this subset, all other variables are as originally defined.

Another preferred aspect of the invention relates to compounds of formula I wherein $R^2$ is H and n is 0. Within this subset, all other variables are as originally defined.

Another preferred aspect of the invention relates to compounds of formula I wherein $R^1$ represents a member selected from the group consisting of: H, $C_{1-4}$alkyl optionally substituted by $OR^7$ and $C_{5-7}$cycloalkyl optionally containing one heteroatom selected from O, S and $NR^8$. Within this subset, all other variables are as originally defined.

Another preferred aspect of the invention relates to compounds of formula I wherein Z represents $HET^1$ and $HET^1$ represents a 5 or 6 membered aromatic ring, or the benzo-fused analog thereof, containing from 1–3 heteroatoms selected from O, S and N, and optionally substituted with 1–2 groups selected from halo, $C_{1-4}$alkyl and $C_{1-4}$acyl. Within this subset, all other variables are as originally defined.

Examples of $HET^1$ include: pyridine, pyrimidine, pyridazine, furan, thiophene, thiazole and oxazole.

Examples of $HET^2$ include butyrolactone, tetrahydrofuran, tetrahydropyran and 2-pyrrolidinone.

Examples of $HET^3$ include butyrolactone, tetrahydrofuran, tetrahydropyran, 2-pyrrolidinone, pyridine and pyrimidine.

Examples of $HET^4$ include 1,2,3-oxadiazole, 1,2,4-oxadiazole, 1,3,4-oxadiazole, 1,2,3-thiadiazole, 1,2,4-thiadiazole, 1,3,4-thiadiazole, thiophene, pyrrole, pyridine, tetrazole, oxazole, thiazole, 1,2,3-triazole, 1,2,4-triazole and 1,3,4-triazole.

A subset of compounds that is of particular interest includes compounds of formula I wherein:

a and m are 1;

n is 0;

Z is phenyl optionally substituted by one or two groups selected from halo, nitro, $C_{1-4}$alkoxy optionally substituted by up to 3 halogen atoms, or $C_{1-4}$alkyl optionally substituted by up to 3 halogen atoms;

$R^1$ represents a member selected from the group consisting of: H, $C_{1-4}$alkyl optionally substituted by $OR^7$ and $C_{5-7}$cycloalkyl optionally containing one heteroatom selected from O, S and $NR^8$.

$R^2$ is hydrogen;

$R^3$ is hydrogen

Z represents $HET^1$ and $HET^1$ represents pyridine, pyrimidine, pyridazine, furan, thiophene, thiazole or oxazole, optionally substituted with 1–2 groups selected from halo, $C_{1-4}$alkyl and $C_{1-4}$acyl;

$HET^2$ is selected from the group consisting of: butyrolactone, tetrahydrofuran, tetrahydropyran and 2-pyrrolidinone;

$HET^3$ is selected from the group consisting of: butyrolactone, tetrahydrofuran, tetrahydropyran, 2-pyrrolidinone, pyridine and pyrimidine;

and $HET^4$ is selected from the group consisting of: 1,2,3-oxadiazole, 1,2,4-oxadiazole, 1,3,4-oxadiazole, 1,2,3-thiadiazole, 1,2,4-thiadiazole, 1,3,4-thiadiazole, thiophene, pyrrole, pyridine, tetrazole, oxazole, thiazole, 1,2,3-triazole, 1,2,4-triazole and 1,3,4-triazole.

Within this subset, all other variables are as originally defined.

L-amino acids and abbreviations:

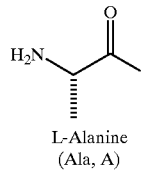
L-Alanine
(Ala, A)

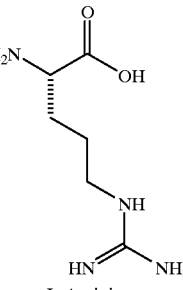
L-Arginine
(Arg, R)

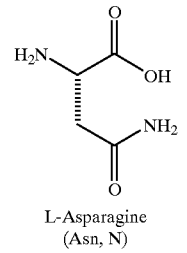
L-Asparagine
(Asn, N)

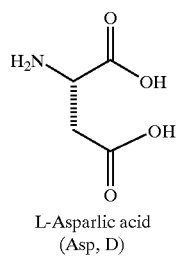
L-Asparlic acid
(Asp, D)

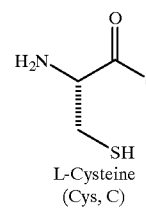
L-Cysteine
(Cys, C)

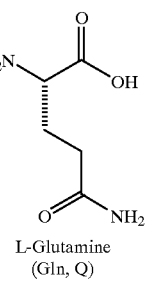
L-Glutamine
(Gln, Q)

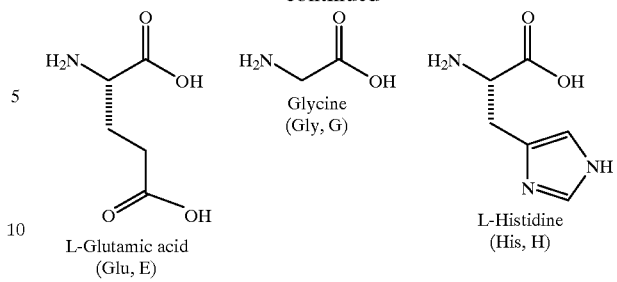
L-Glutamic acid (Glu, E)    Glycine (Gly, G)    L-Histidine (His, H)

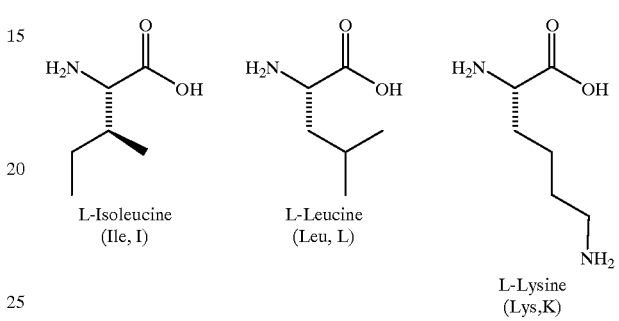
L-Isoleucine (Ile, I)    L-Leucine (Leu, L)    L-Lysine (Lys, K)

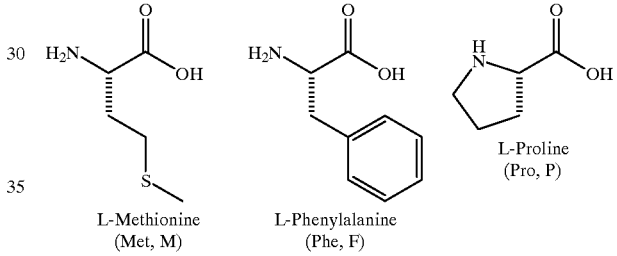
L-Methionine (Met, M)    L-Phenylalanine (Phe, F)    L-Proline (Pro, P)

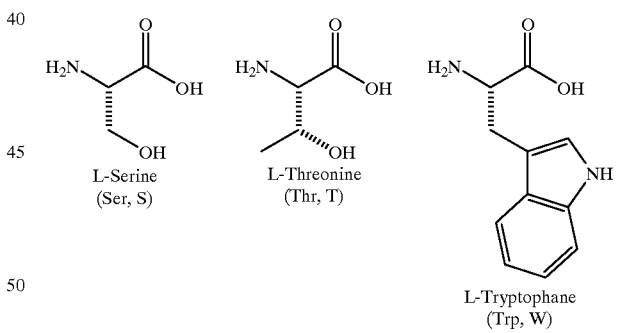
L-Serine (Ser, S)    L-Threonine (Thr, T)    L-Tryptophane (Trp, W)

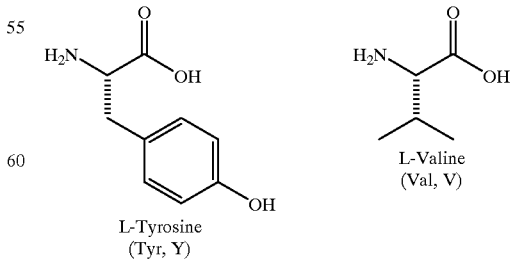
L-Tyrosine (Tyr, Y)    L-Valine (Val, V)

Representative examples of compounds of formula I are found in Table I below.

TABLE I
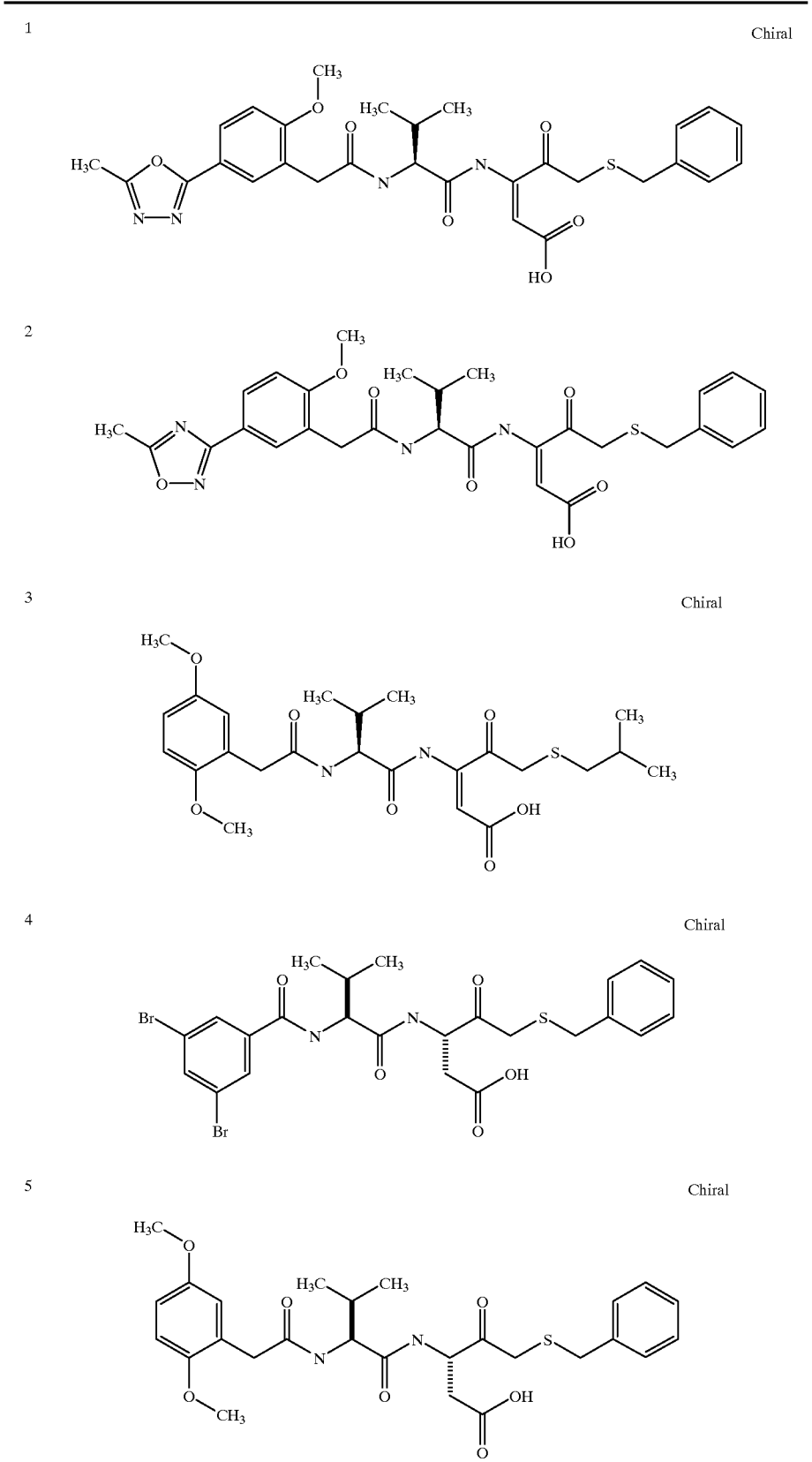

TABLE I-continued
6 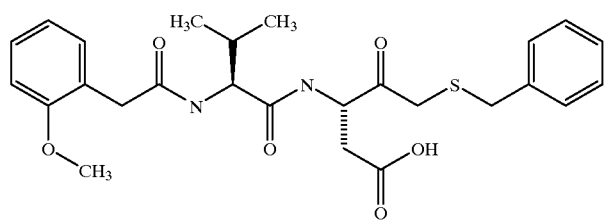 Chiral
7 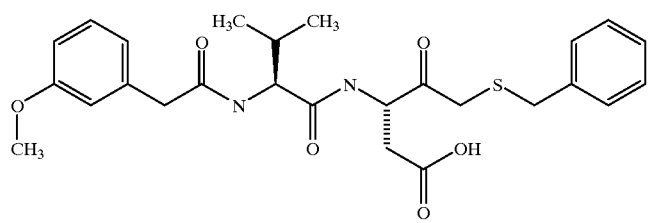 Chiral
8 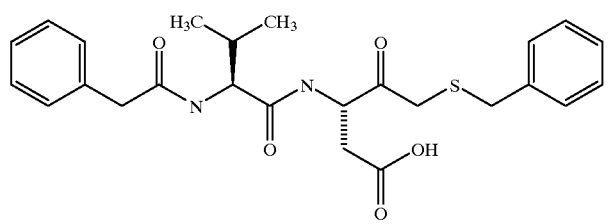 Chiral
9 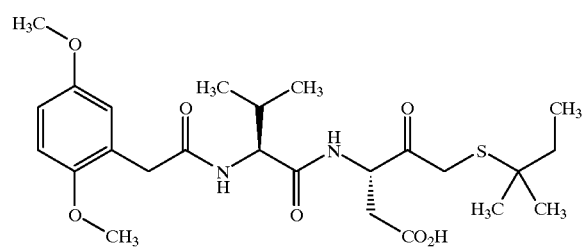 Chiral
10 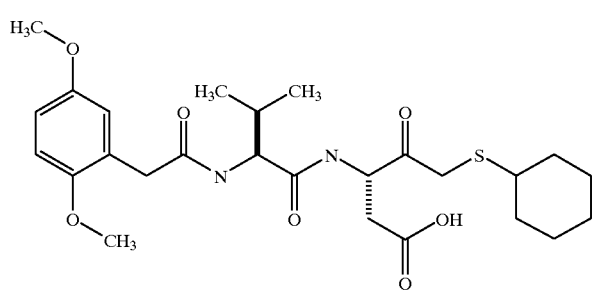 Chiral TABLE I-continued
11 Chiral
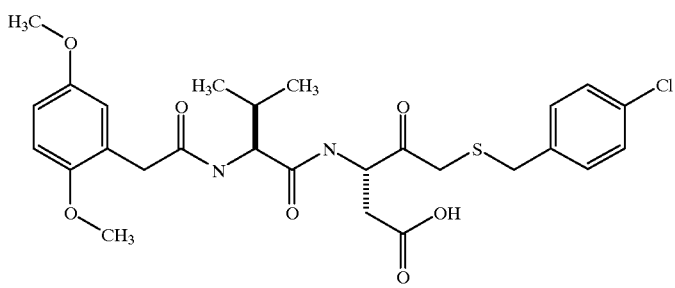
12 Chiral
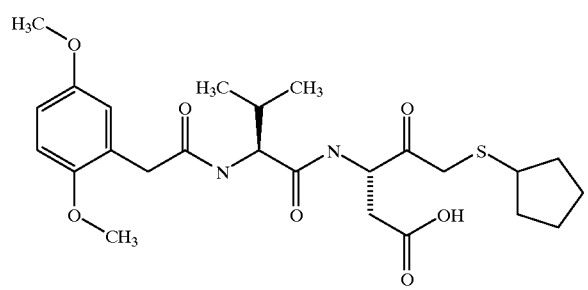
13 Chiral
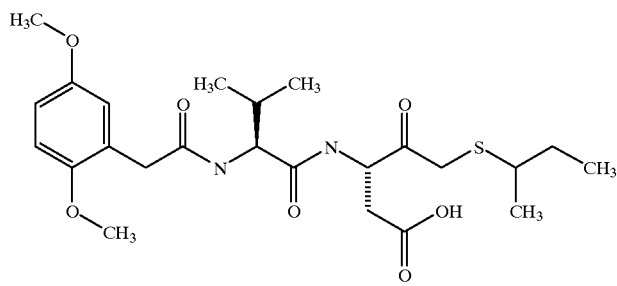
14 Chiral
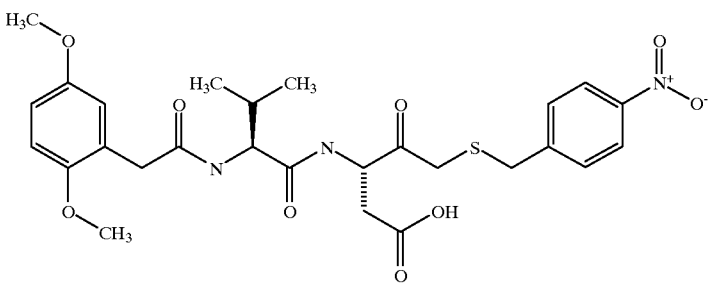

TABLE I-continued
15 Chiral
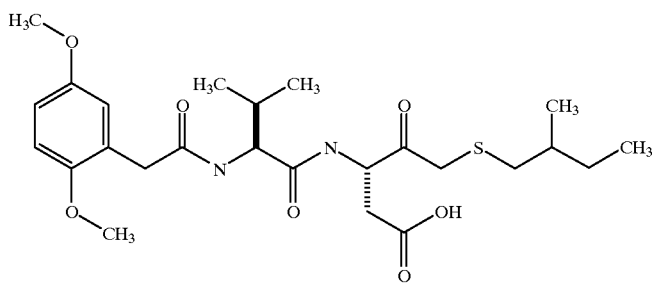
16 Chiral
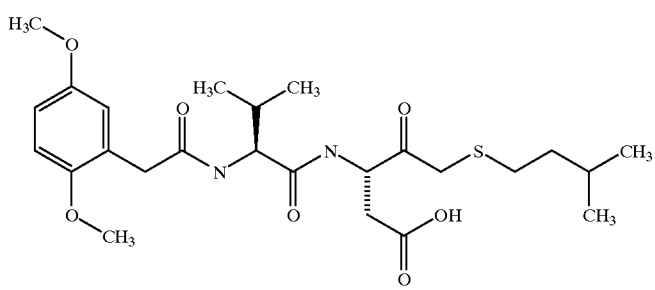
17 Chiral
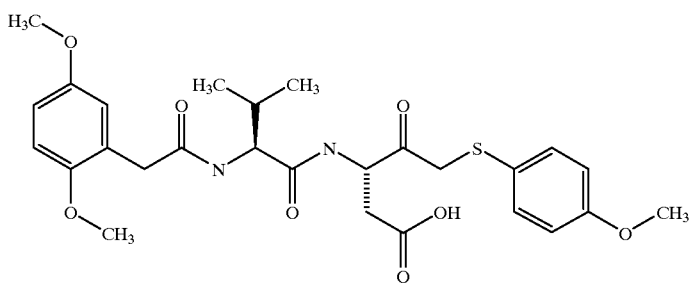
18 Chiral
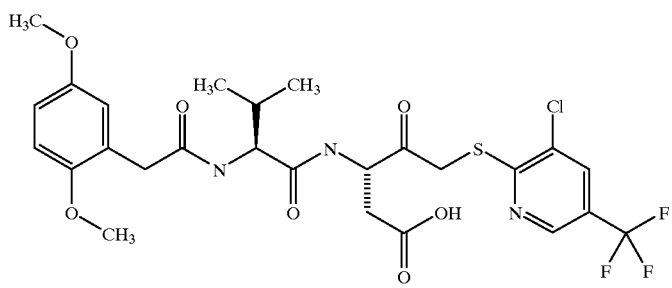

TABLE I-continued
19 Chiral
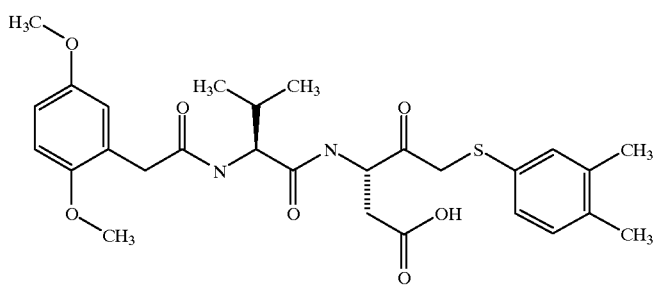
20 Chiral
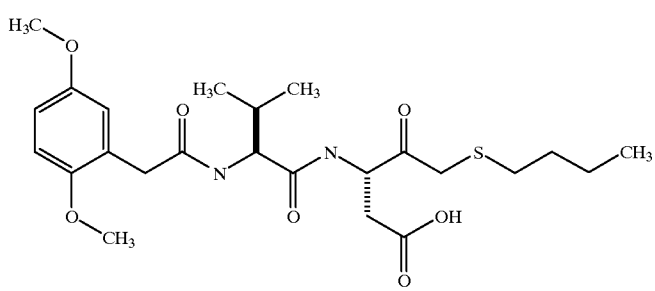
21 Chiral
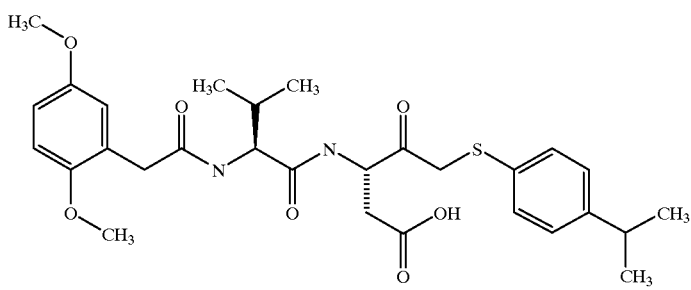
22 Chiral
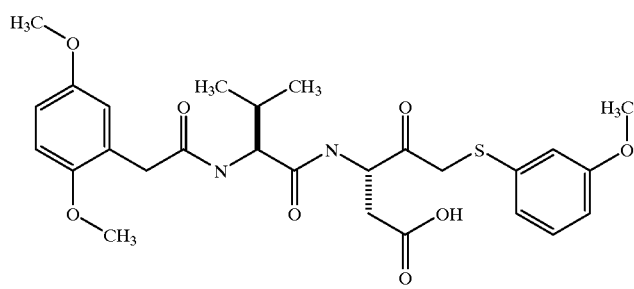

TABLE I-continued
| 23 | 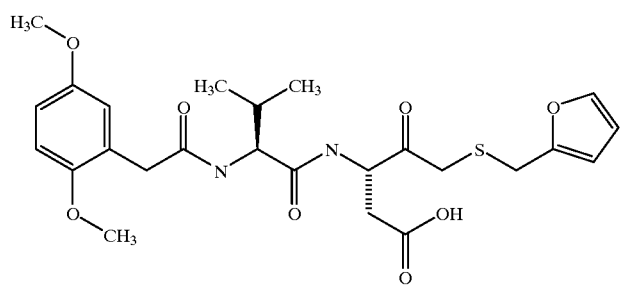 | Chiral |
| 24 | 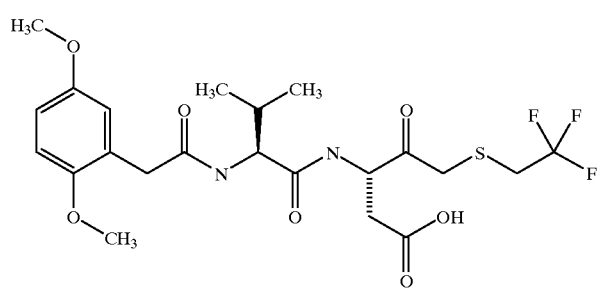 | Chiral |
| 25 | 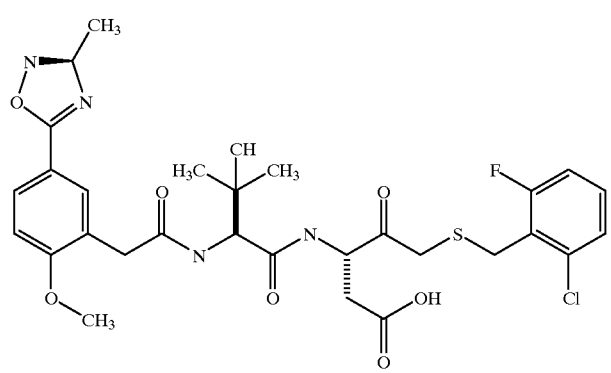 | Chiral |
| 26 | 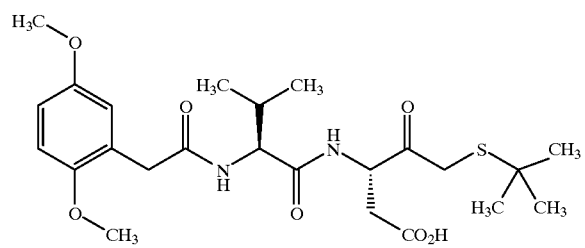 | Chiral |

TABLE I-continued
27 Chiral
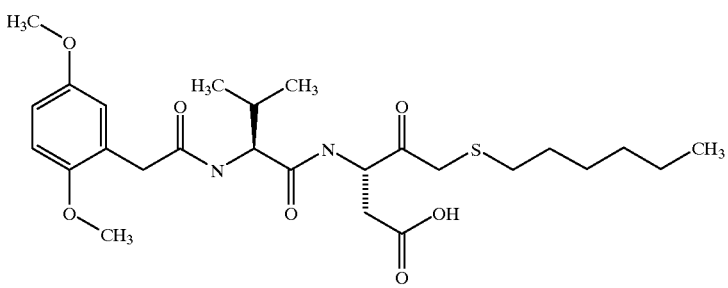
28 Chiral
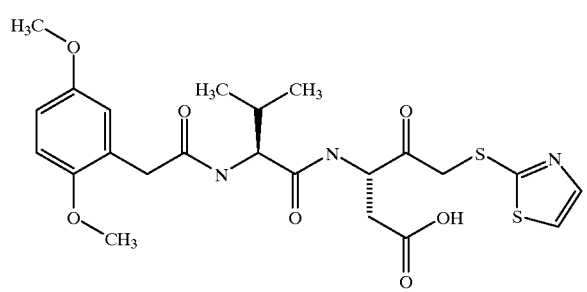
29 Chiral
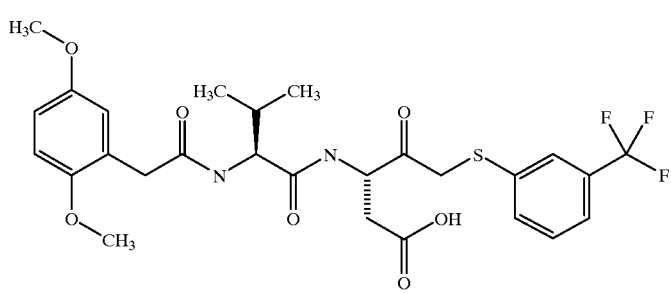
30 Chiral
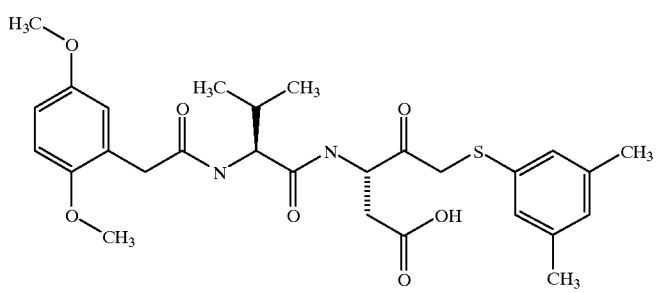

TABLE I-continued
31 Chiral
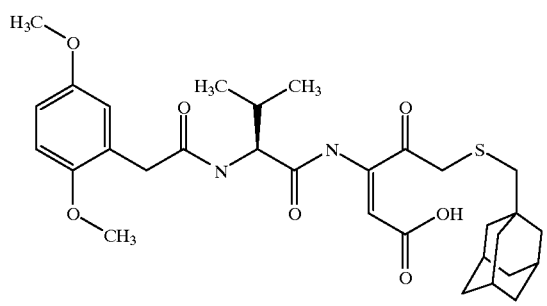
32 Chiral
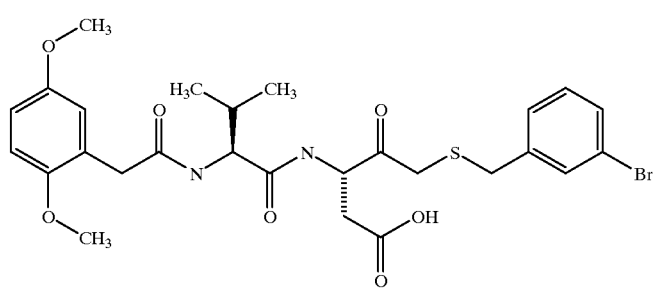
33 Chiral
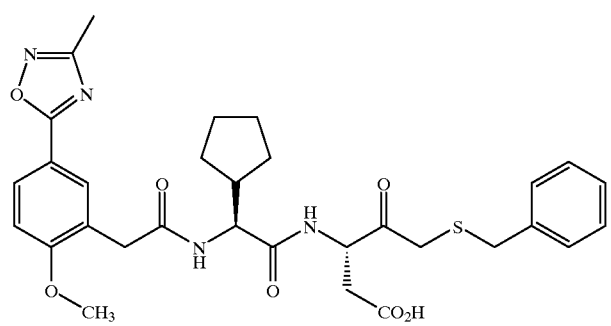
34 Chiral
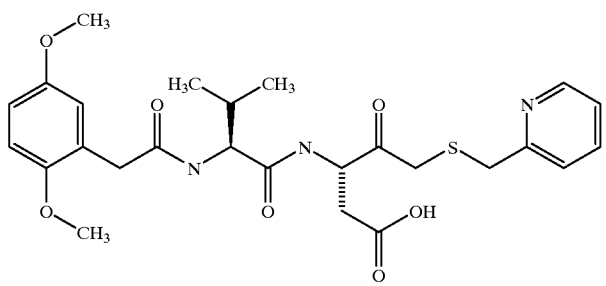

TABLE I-continued
| | | |
|---|---|---|
| 35 | 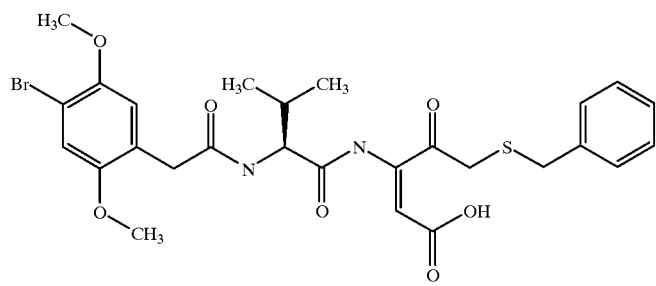 | Chiral |
| 36 | 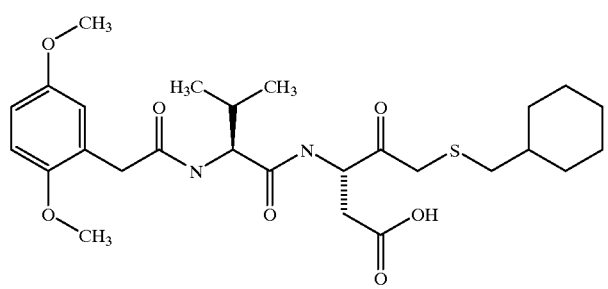 | Chiral |
| 37 | 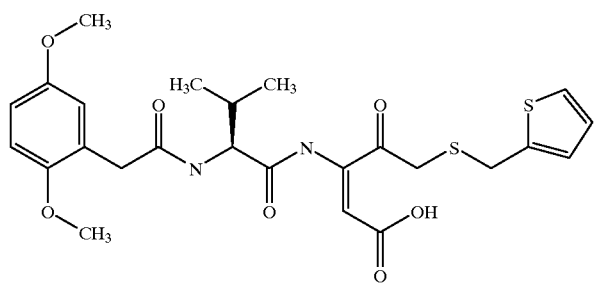 | Chiral |
| 38 | 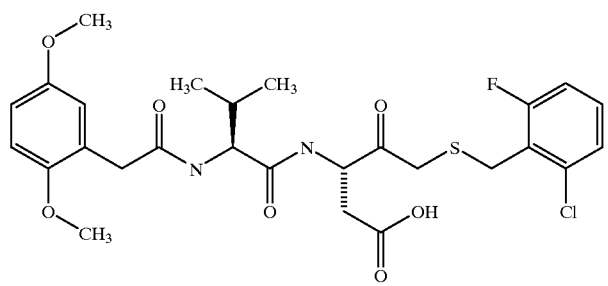 | Chiral |

TABLE I-continued
| 39 | 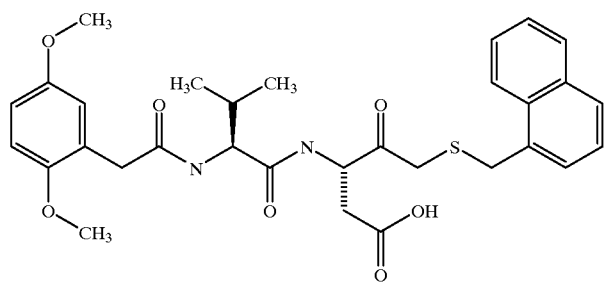 | Chiral |
| --- | --- | --- |
| 40 | 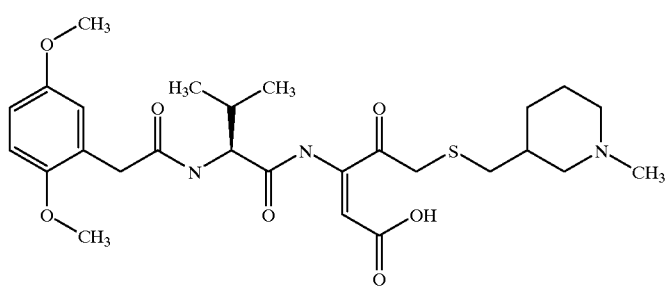 | Chiral |
| 41 | 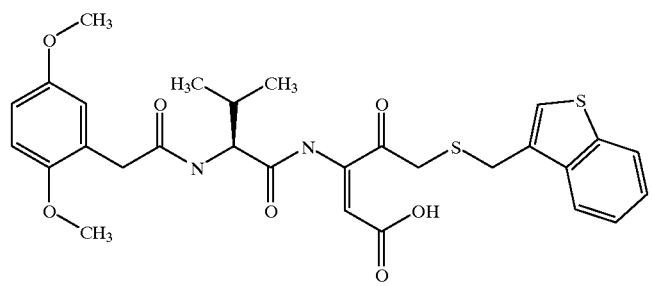 | Chiral |
| 42 | 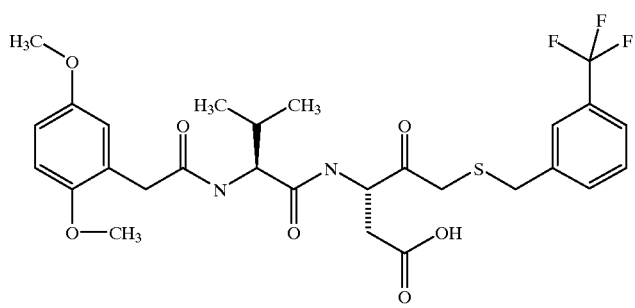 | Chiral |

TABLE I-continued
| 43 | 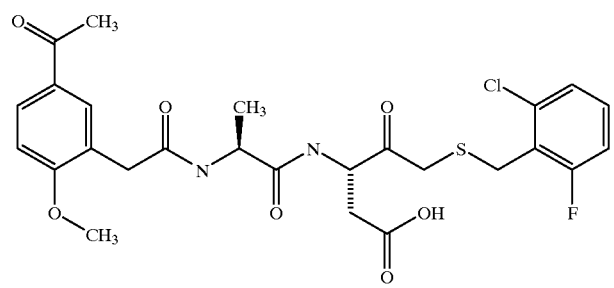 | Chiral |
|---|---|---|
| 44 | 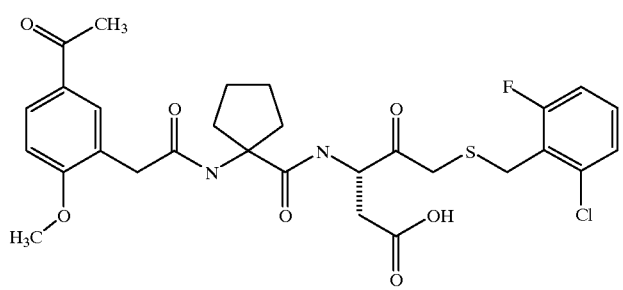 | Chiral |
| 45 | 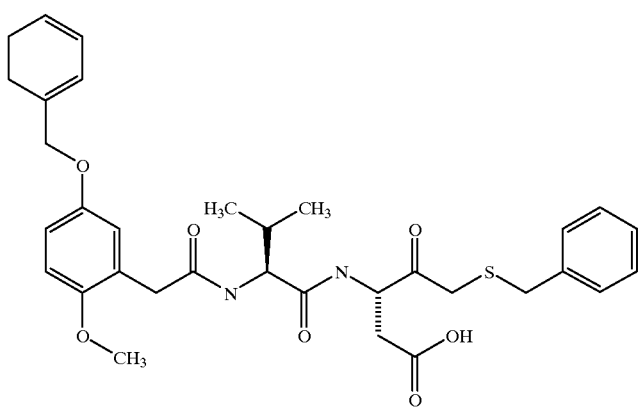 | Chiral |
| 46 | 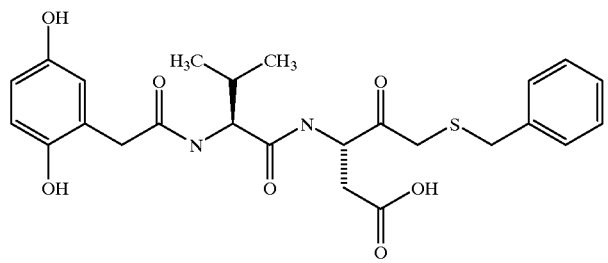 | Chiral |

TABLE I-continued
47 Chiral
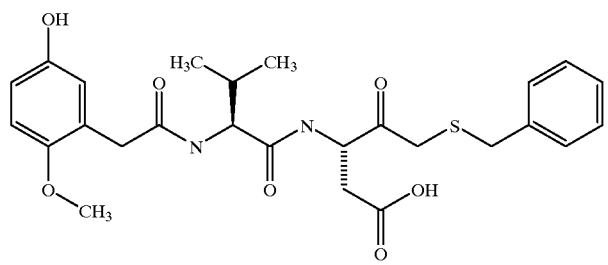
48 Chiral
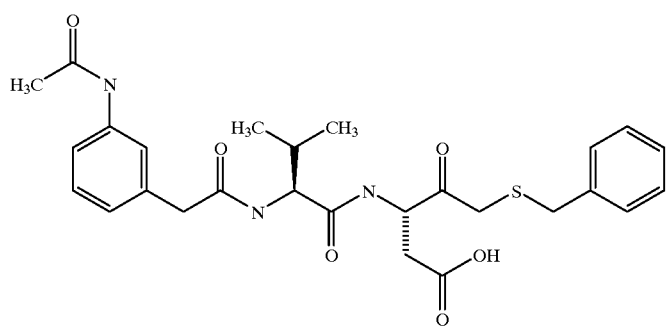
49 Chiral
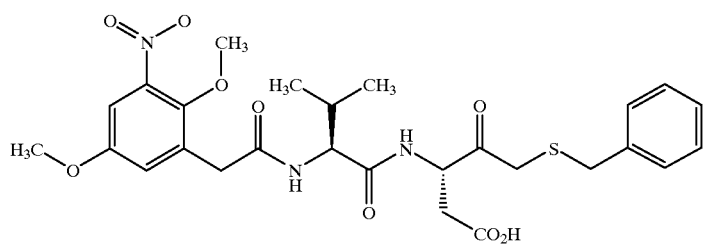
50 Chiral
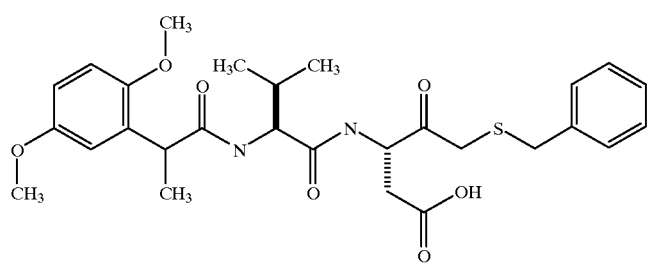

TABLE I-continued
51 Chiral
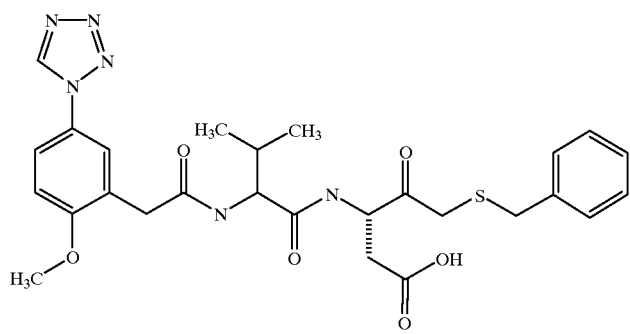
52 Chiral
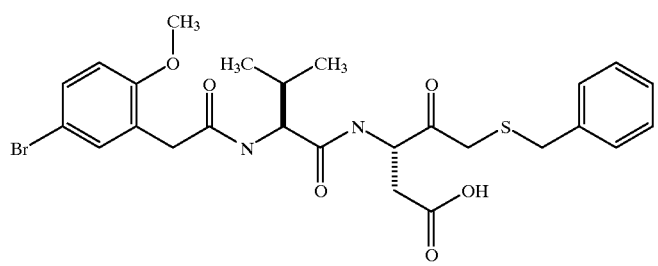
53 Chiral
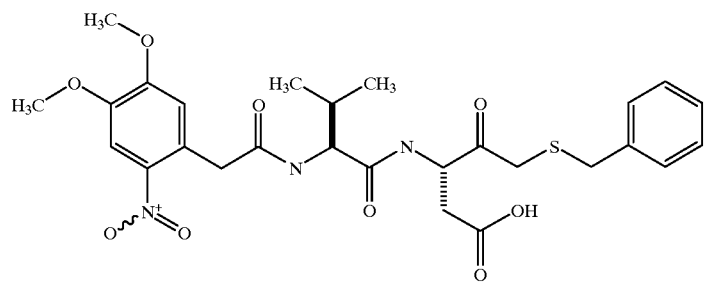
54 Chiral
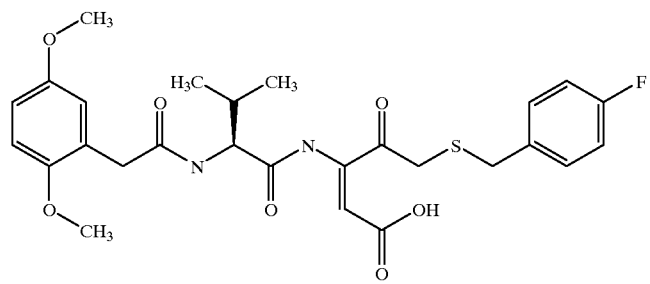

TABLE I-continued
55 Chiral
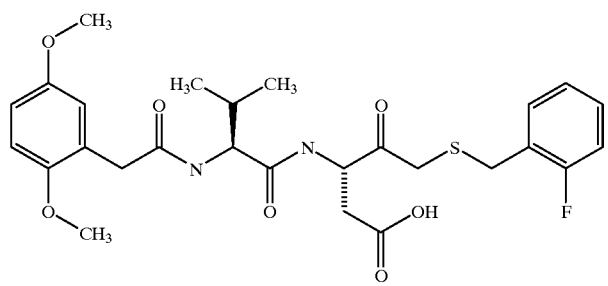
56 Chiral
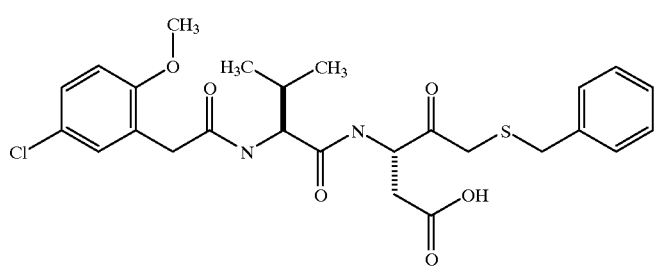
57 Chiral
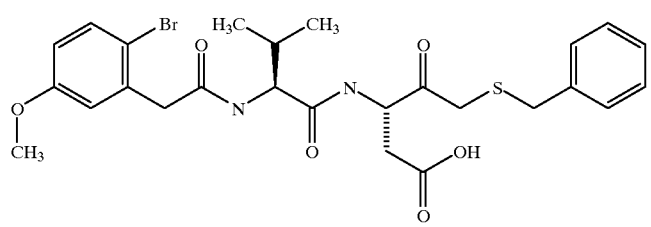
58 Chiral
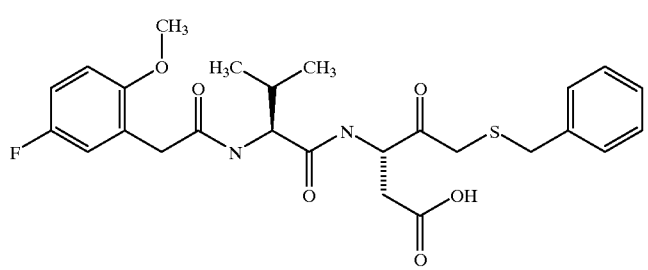
59 Chiral
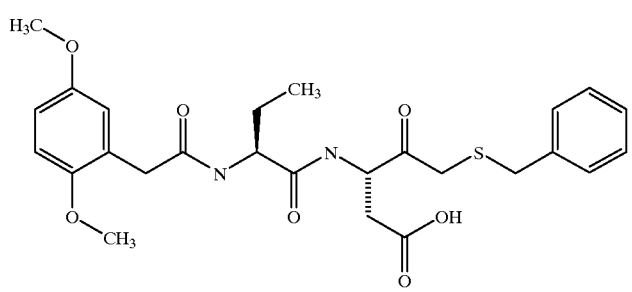

TABLE I-continued
60 Chiral
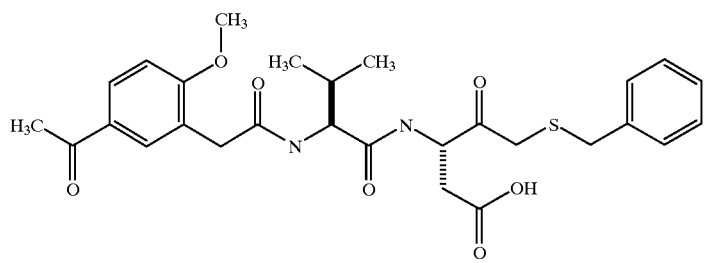
61 Chiral
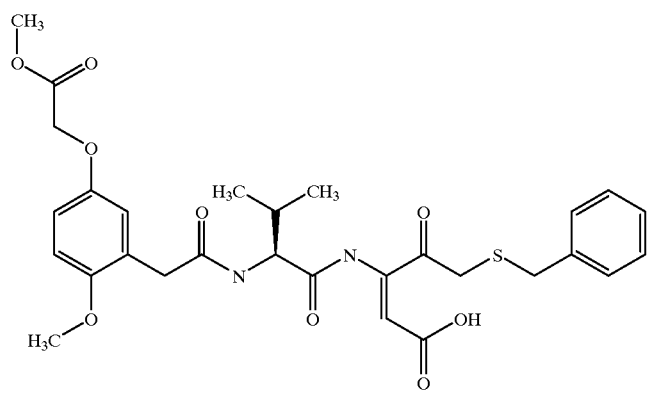
62 Chiral
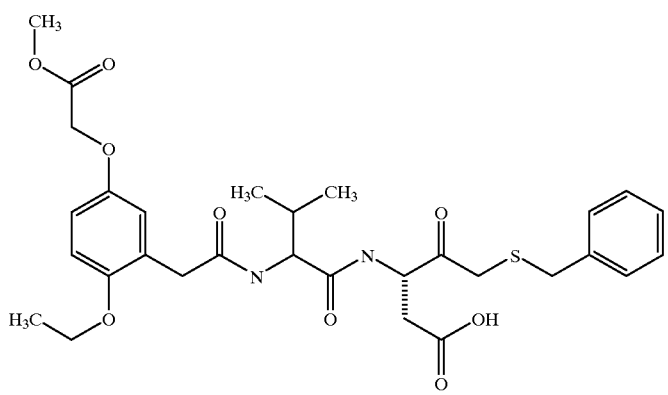

TABLE I-continued
| 63 | 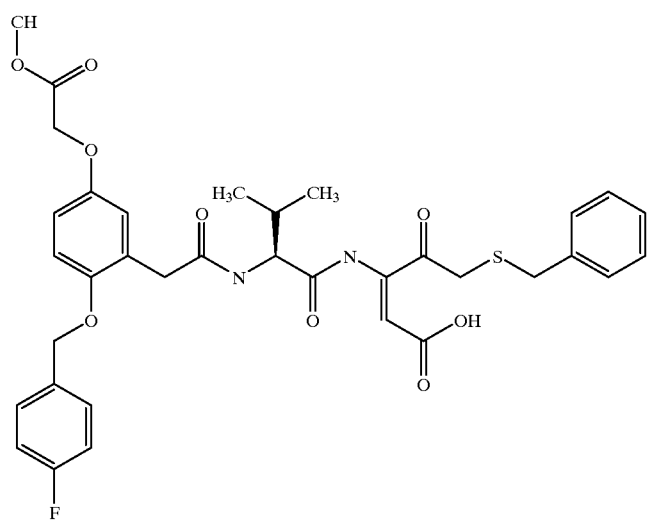 | Chiral |
|---|---|---|
| 64 | 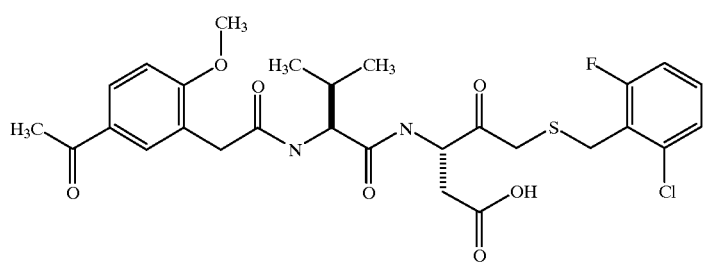 | Chiral |
| 65 | 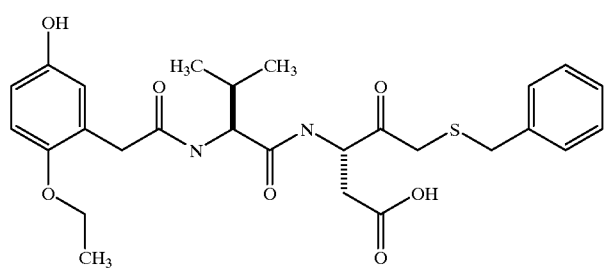 | Chiral |
| 66 | 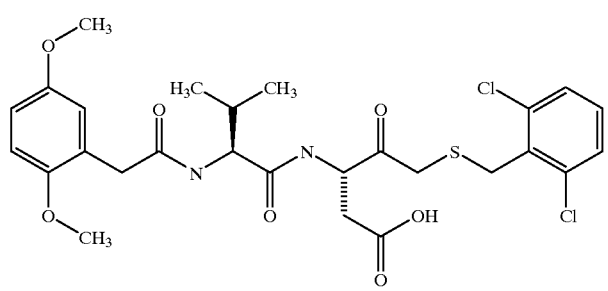 | Chiral |

TABLE I-continued
| 67 | 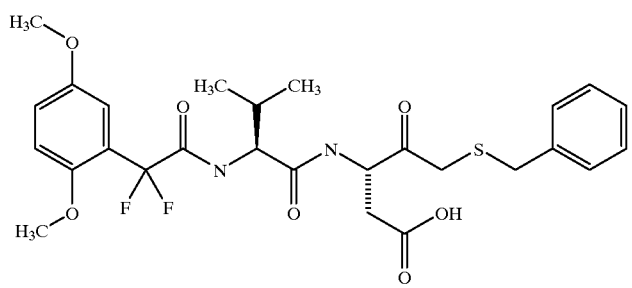 | Chiral |
| 68 | 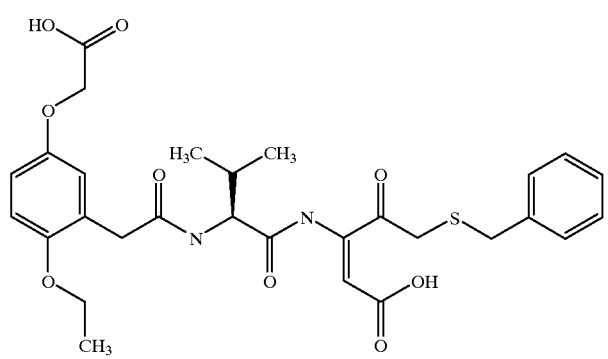 | Chiral |
| 69 | 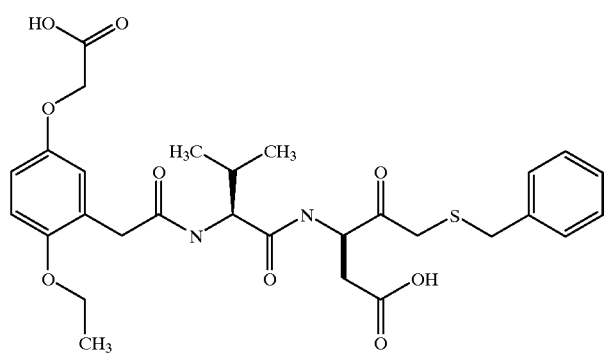 | Chiral |
| 70 | 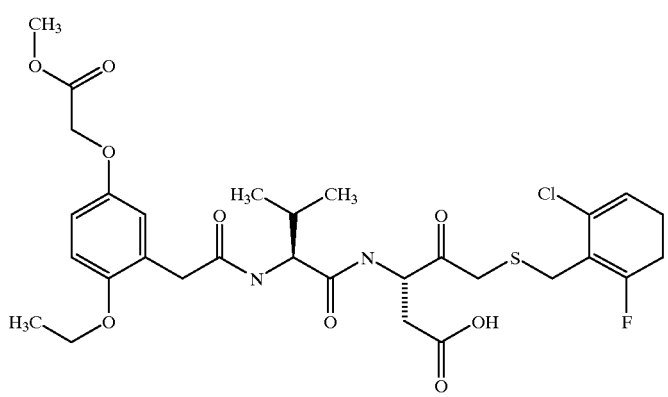 | Chiral |

TABLE I-continued
| | |
|---|---|
| 71 | Chiral |
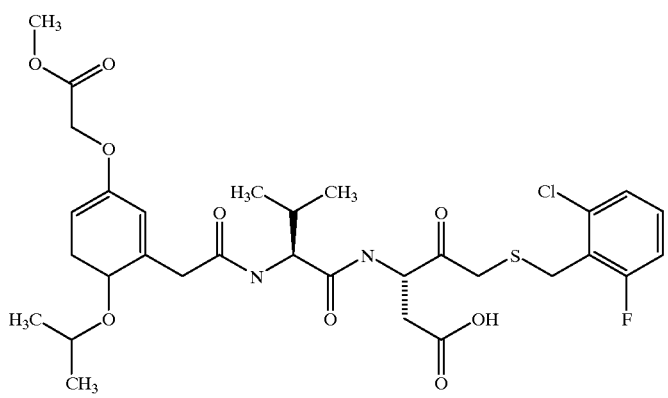
| | |
|---|---|
| 72 | Chiral |
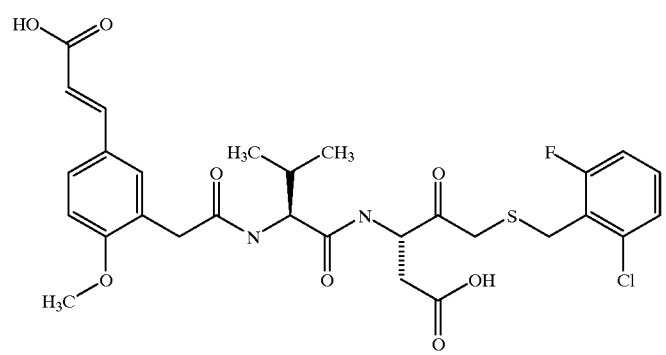
| | |
|---|---|
| 73 | Chiral |
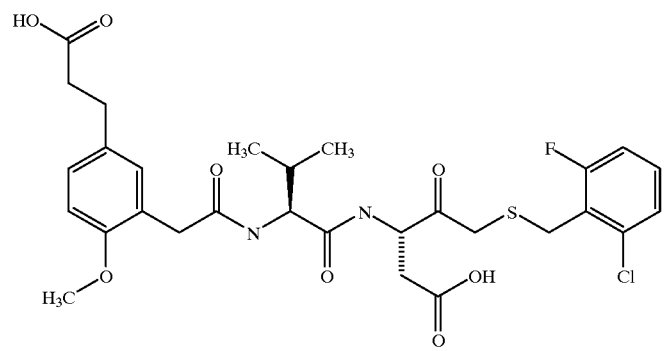
| | |
|---|---|
| 74 | Chiral |
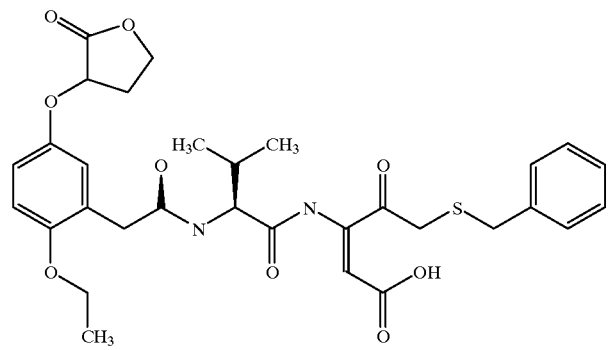

TABLE I-continued
75 Chiral
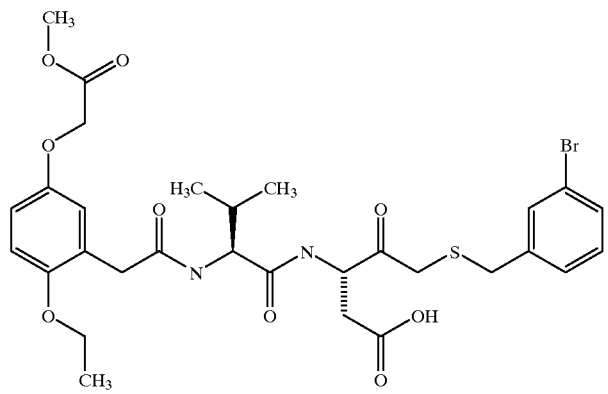
76 Chiral
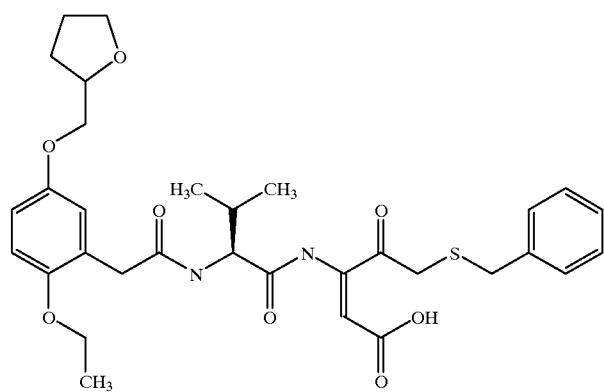
77 Chiral
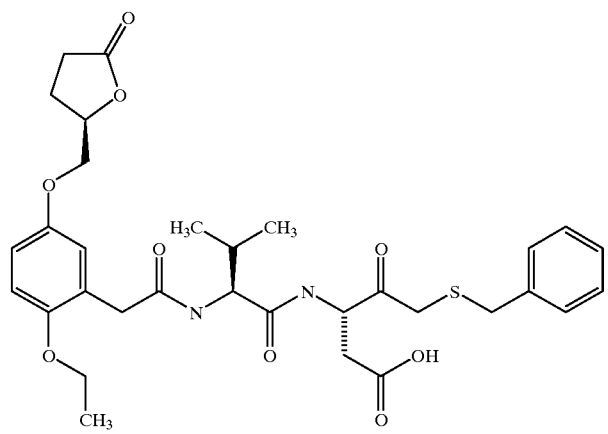

TABLE I-continued
78                                                                                                          Chiral
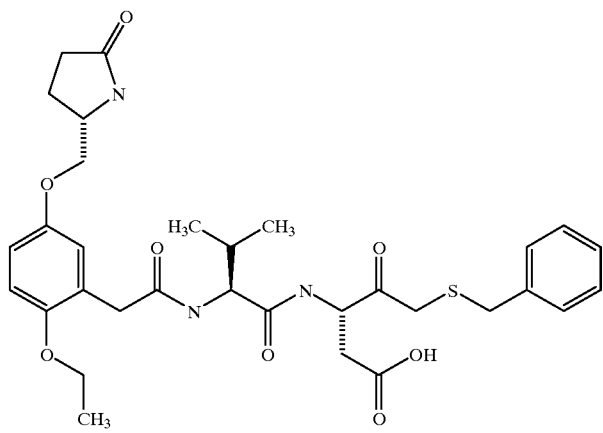
79                                                                                                          Chiral
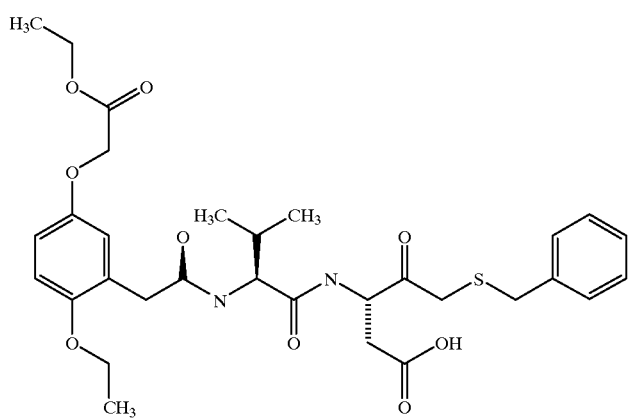
80                                                                                                          Chiral
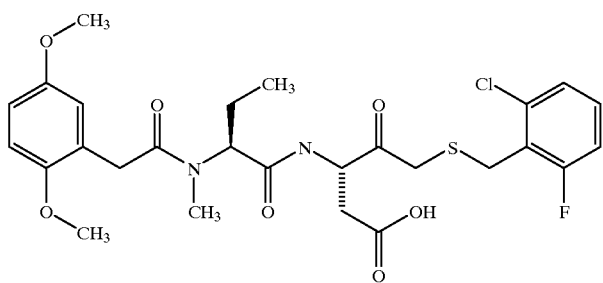

TABLE I-continued
81 Chiral
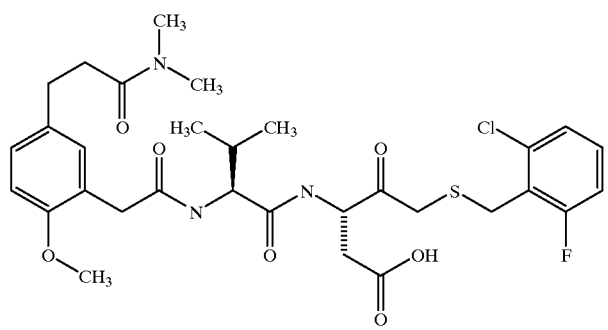
82 Chiral
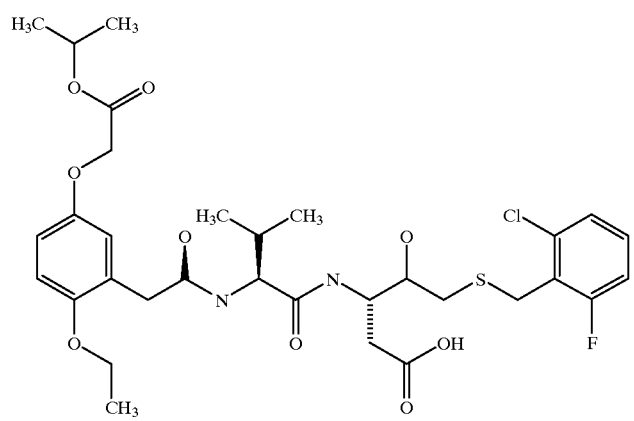
83 Chiral
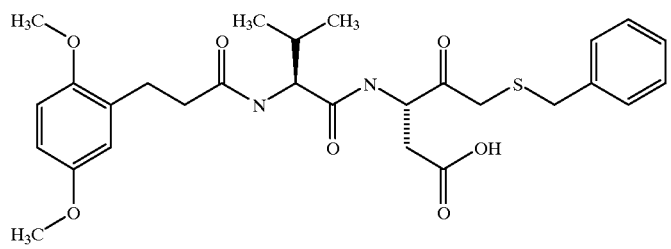
84 Chiral
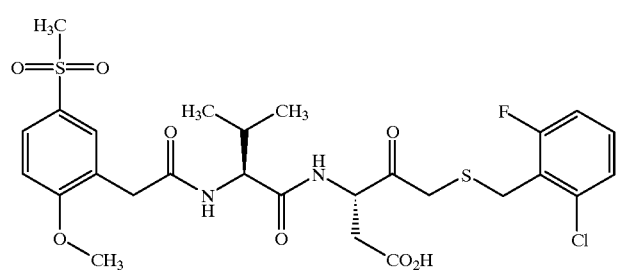

TABLE I-continued
| | | |
|---|---|---|
| 85 | 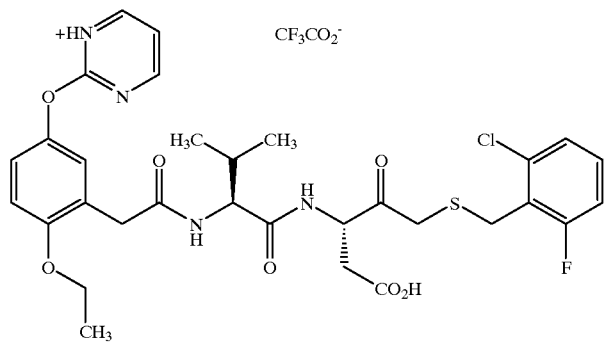 | Chiral |
| 86 | 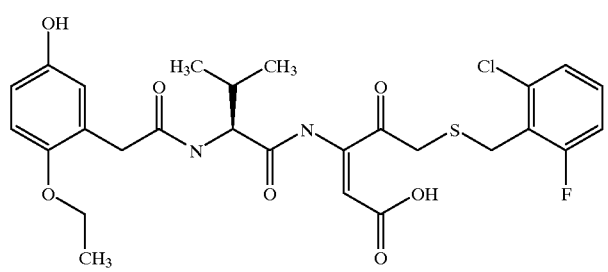 | Chiral |
| 87 | 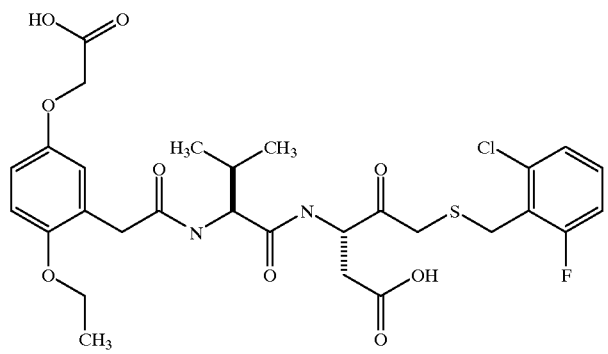 | Chiral |
| 88 | 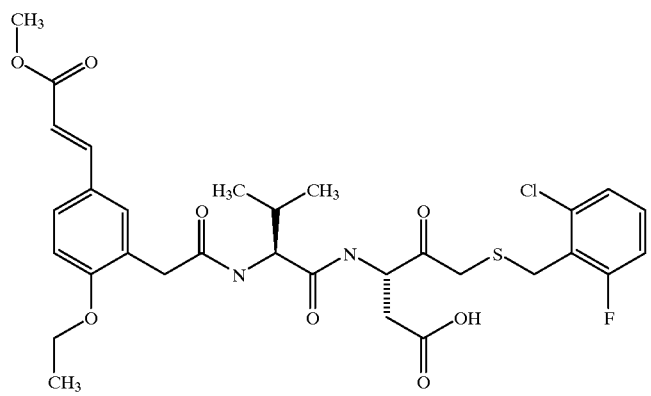 | Chiral |

TABLE I-continued
| | | |
|---|---|---|
| 89 | 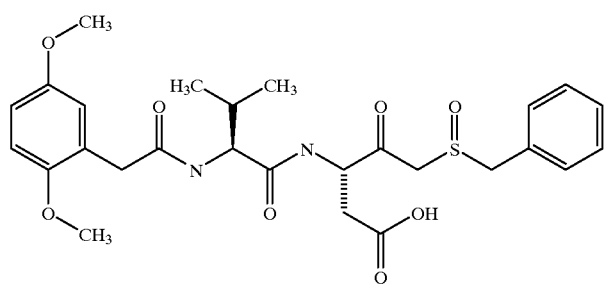 | Chiral |
| 90 | 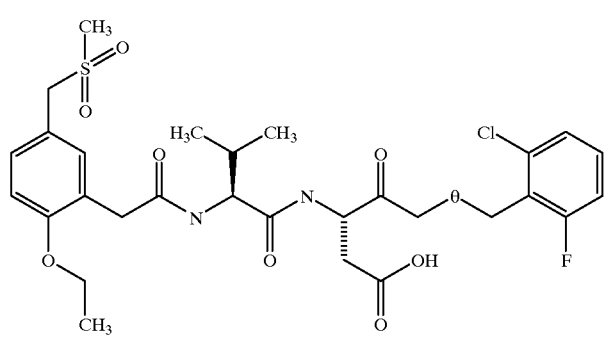 | Chiral |
| 91 | 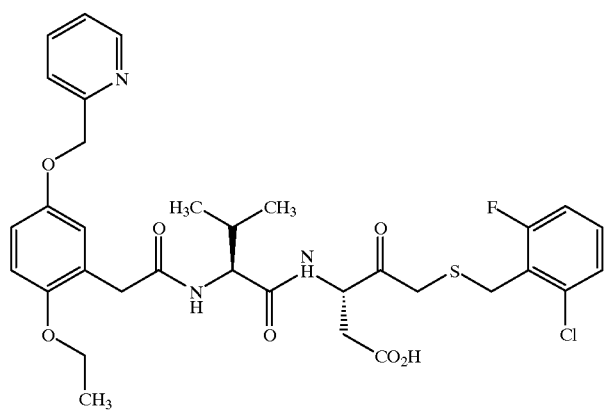 | Chiral |
| 92 | 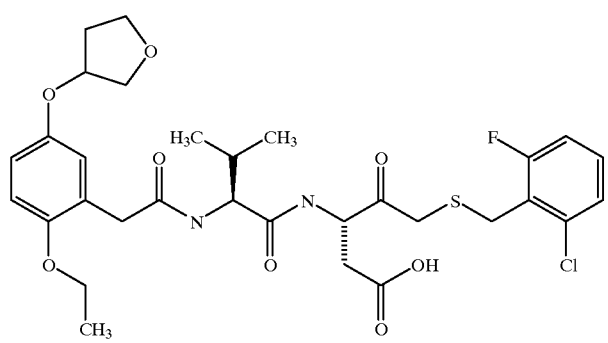 | Chiral |

TABLE I-continued
93 Chiral
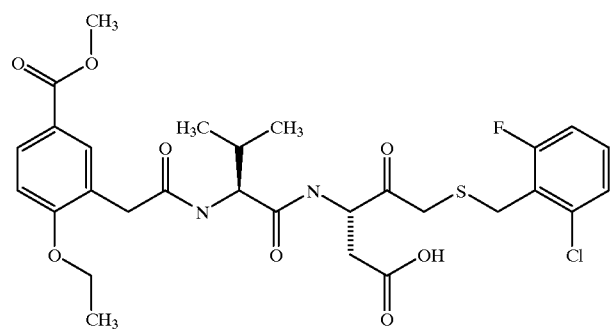
94 Chiral
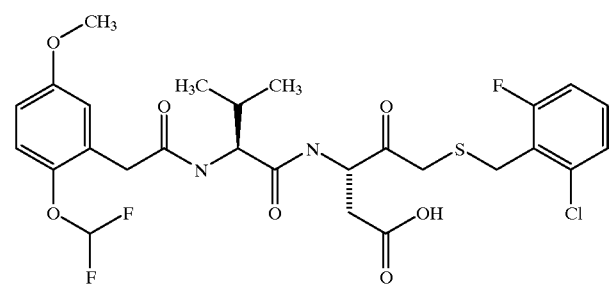
95 Chiral
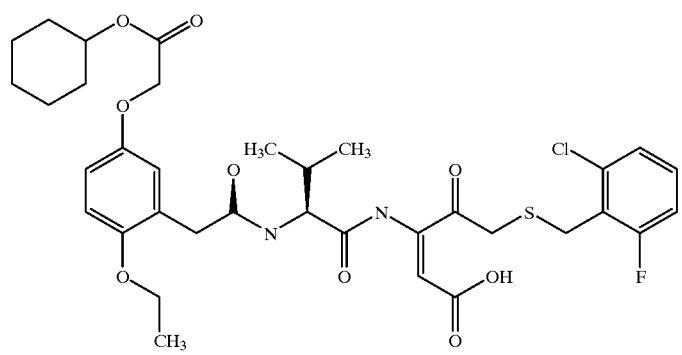
96 Chiral
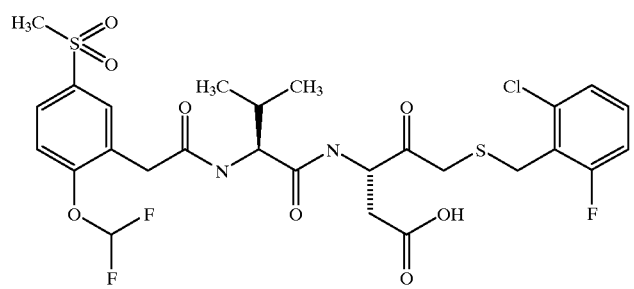

TABLE I-continued
| 97 | 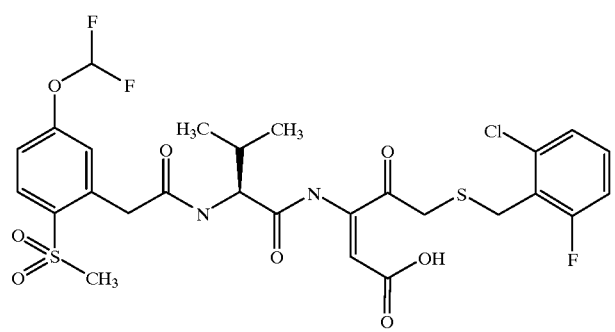 | Chiral |
| --- | --- | --- |
| 98 | 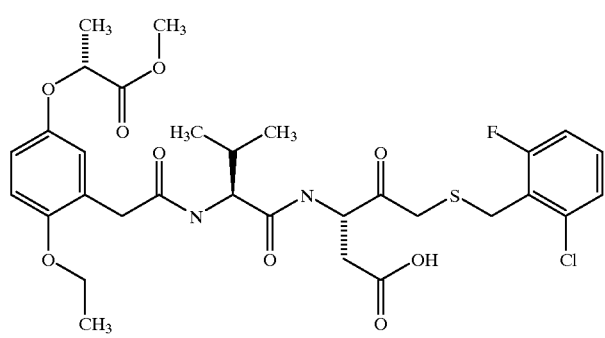 | Chiral |
| 99 | 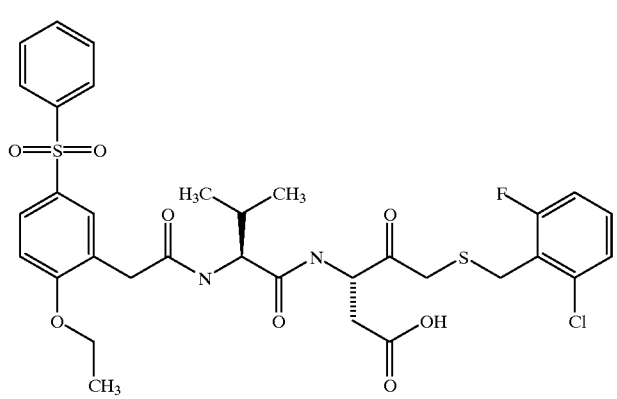 | Chiral |
| 100 | 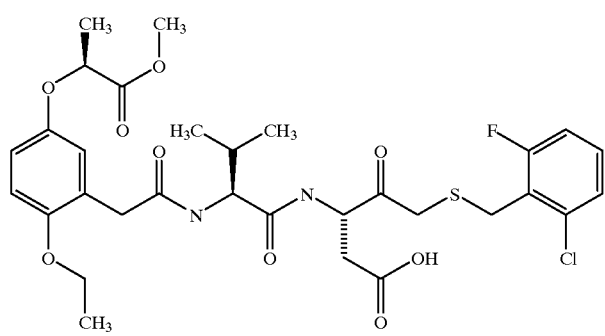 | Chiral |

TABLE I-continued
101 Chiral
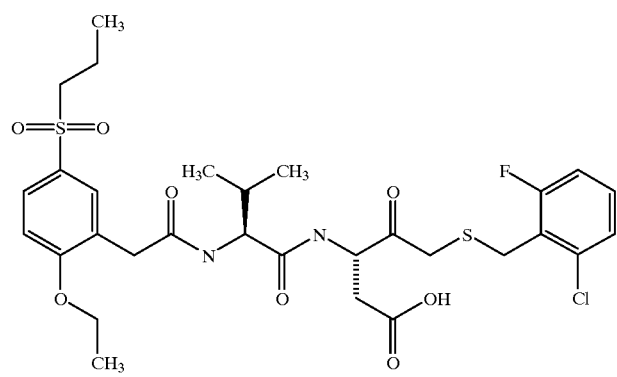
102 Chiral
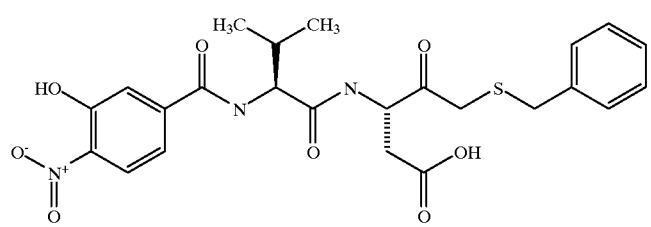
103 Chiral
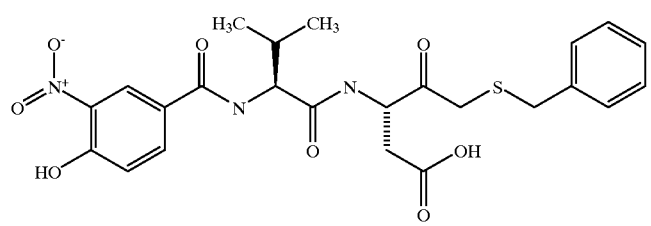
104 Chiral
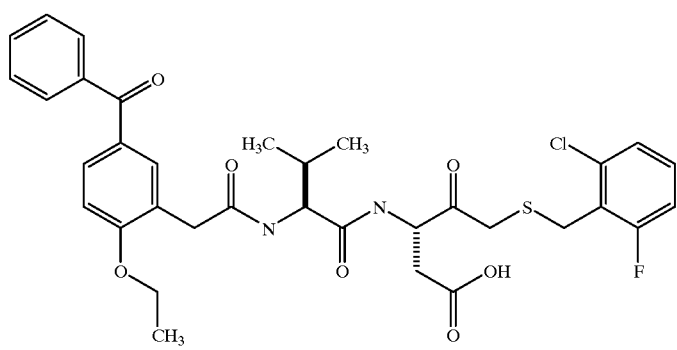

TABLE I-continued
| 105 | 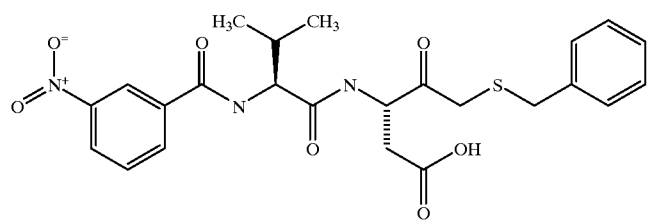 | Chiral |
| 106 | 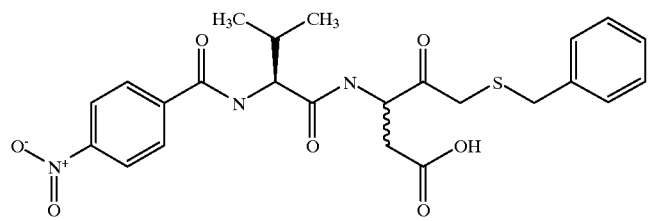 | Chiral |
| 107 | 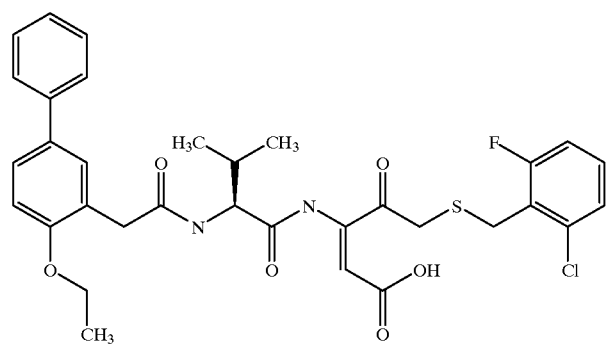 | Chiral |
| 108 | 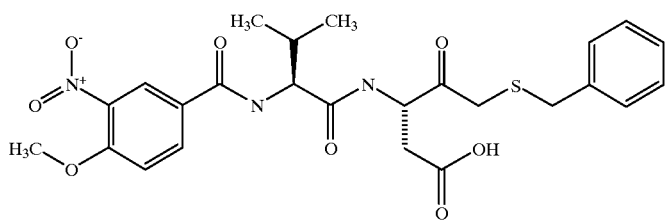 | Chiral |
| 109 | 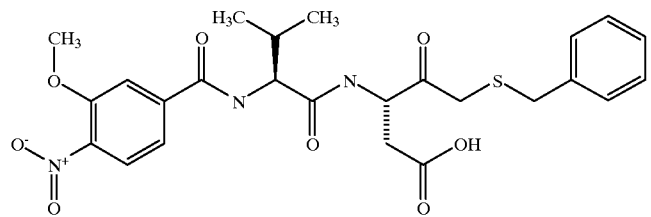 | Chiral |

TABLE I-continued
110 Chiral
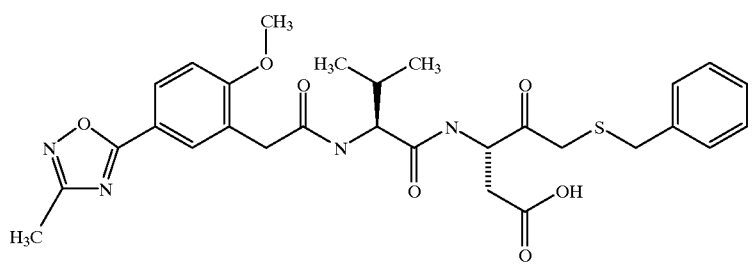
111 Chiral
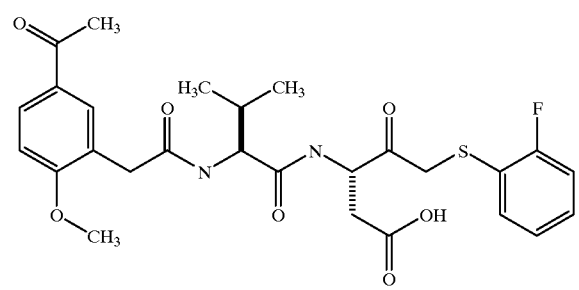
112 Chiral
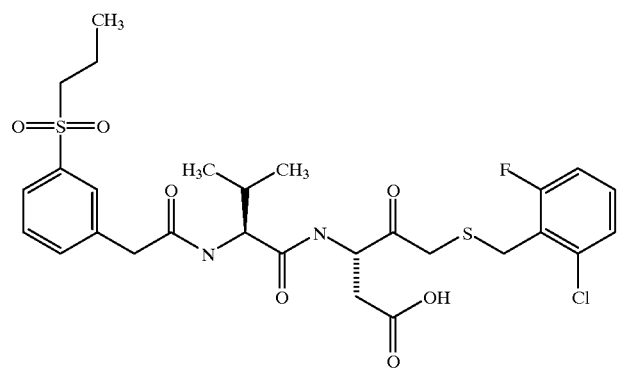
113 Chiral
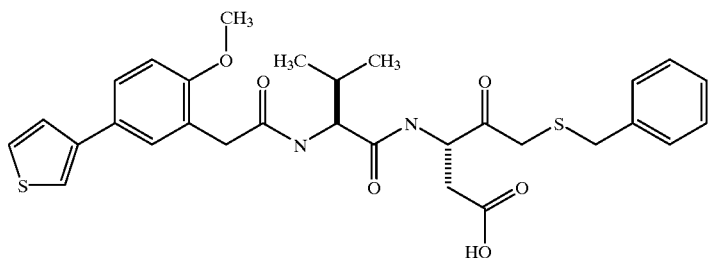

TABLE I-continued
| 114 | 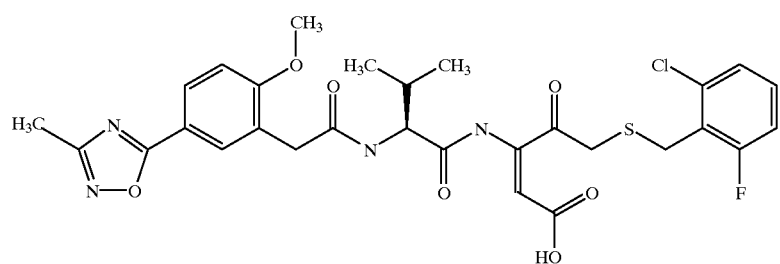 | Chiral |
|---|---|---|
| 115 | 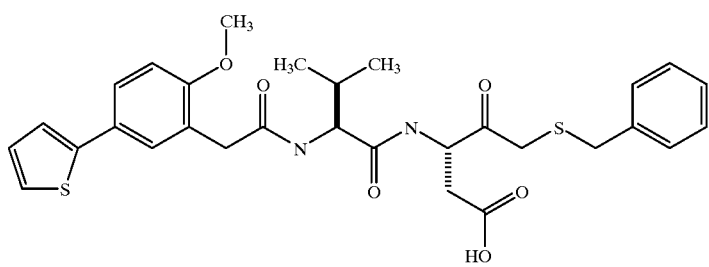 | Chiral |
| 116 | 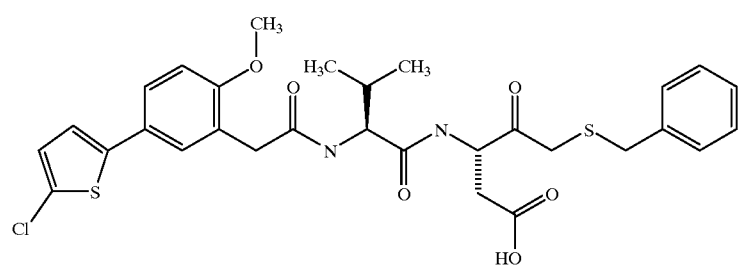 | Chiral |
| 117 | 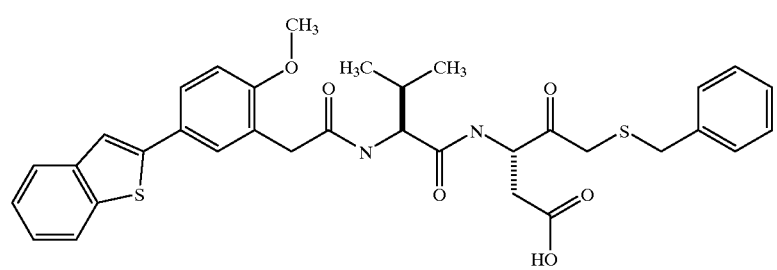 | Chiral |
| 118 | 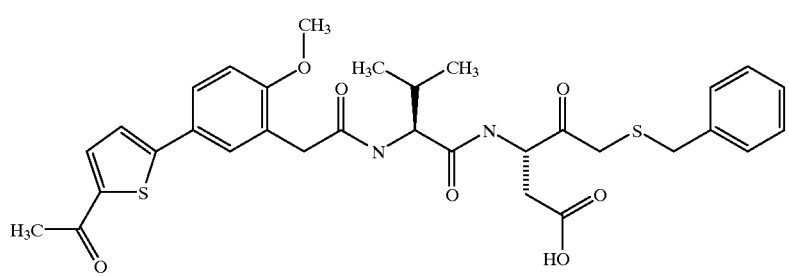 | Chiral |

TABLE I-continued
| 119 | 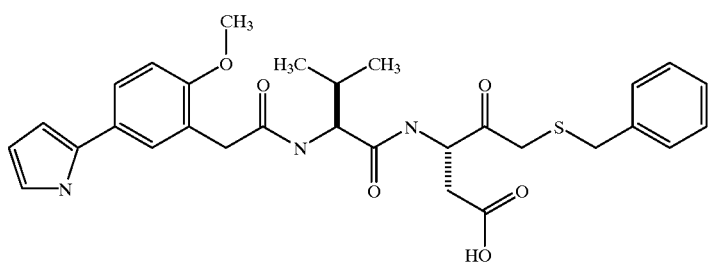 | Chiral |
| 120 | 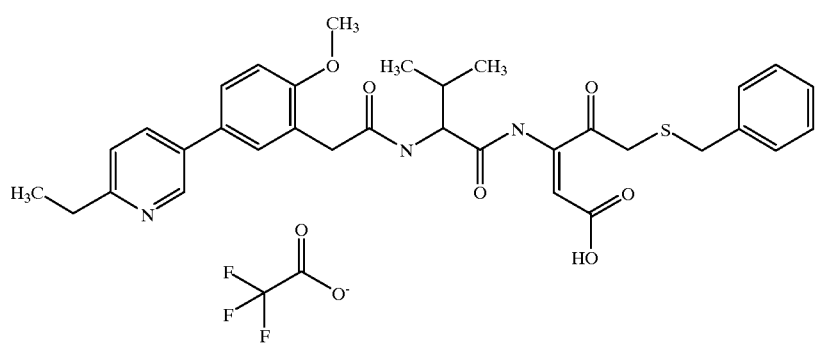 | Chiral |
| 121 | 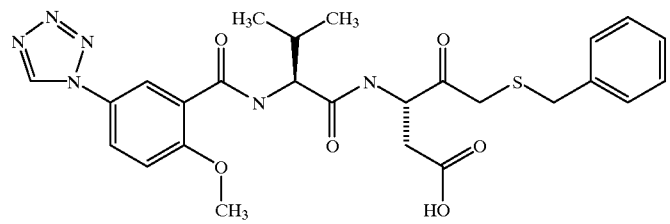 | |
| 122 | 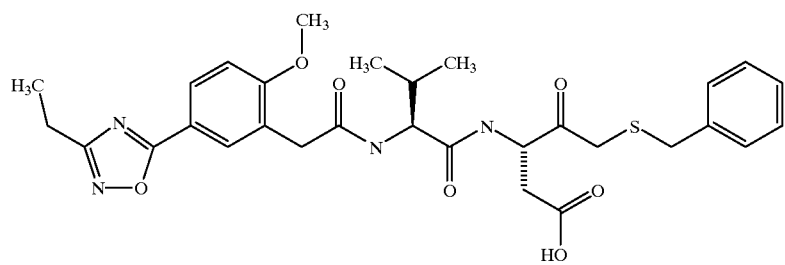 | |
| 123 | 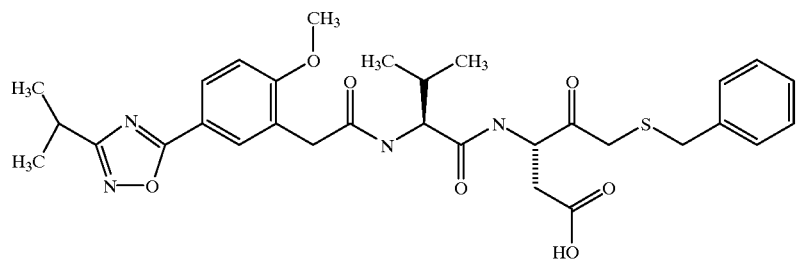 | |

TABLE I-continued
124
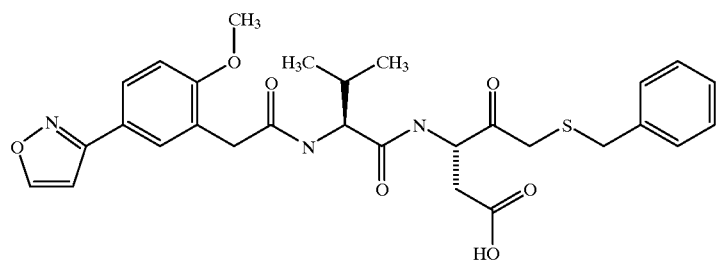
125 Chiral
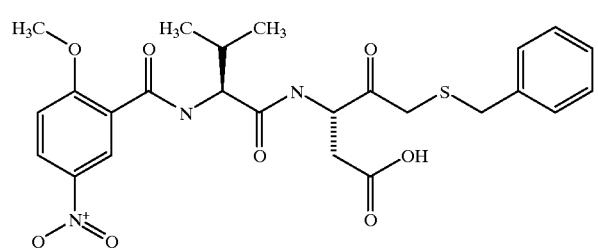
126 Chiral
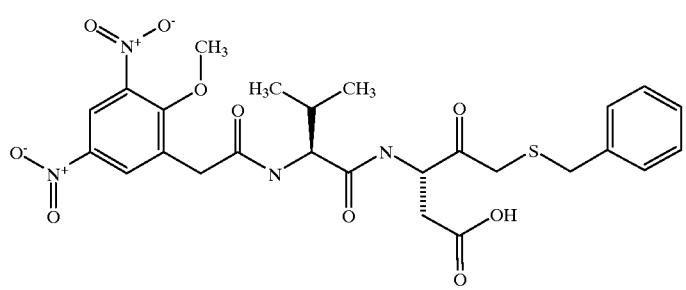
127 Chiral
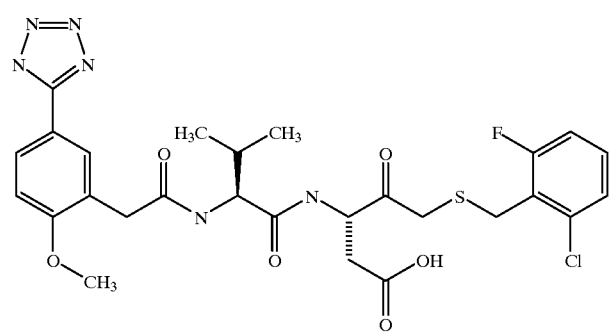
128 Chiral
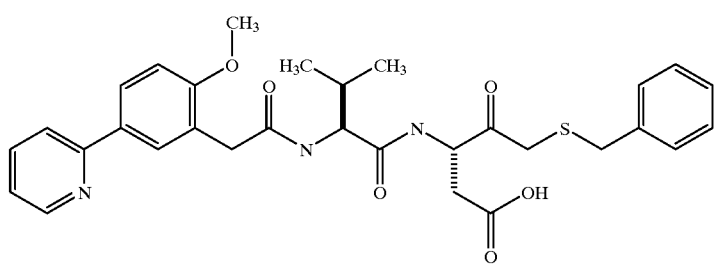

TABLE I-continued

| 129 | (structure) | Chiral |
| 130 | (structure) | Chiral |
| 131 | (structure) | Chiral |
| 132 | (structure) | Chiral |
| 133 | (structure) | Chiral |

TABLE I-continued
| 134 | 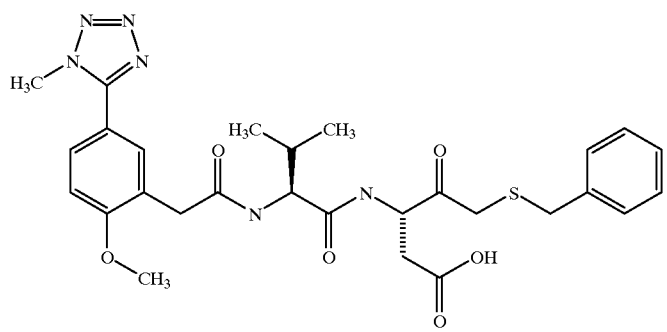 | Chiral |
|---|---|---|
| 135 | 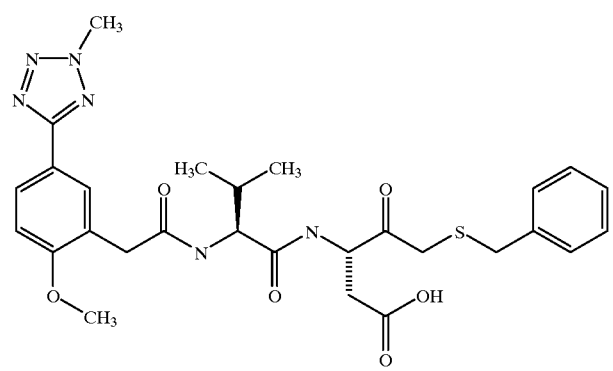 | Chiral |
| 136 | 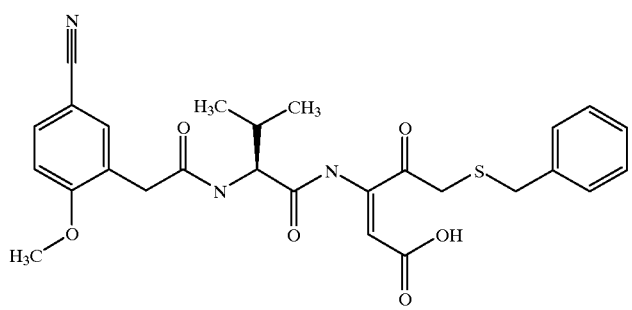 | Chiral |
| 137 | 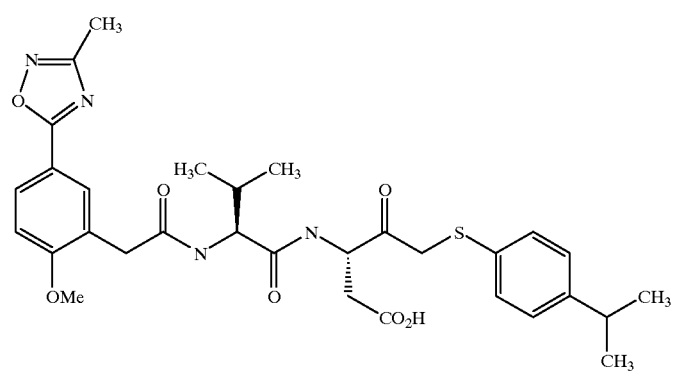 | |

TABLE I-continued
138 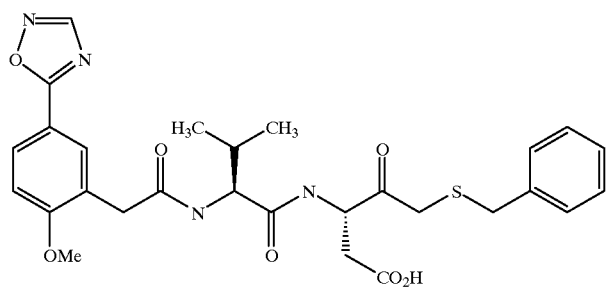
139 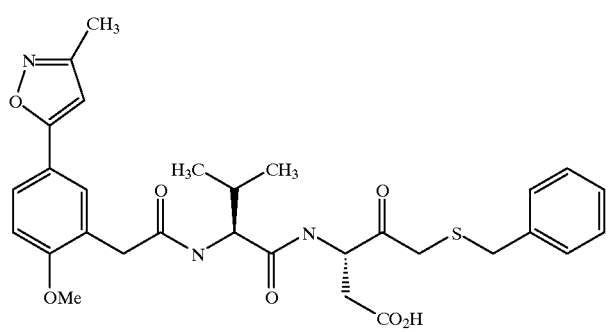
140 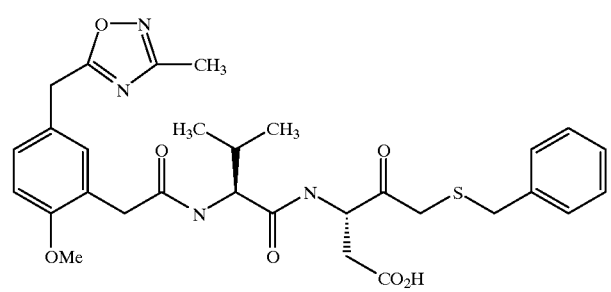
141 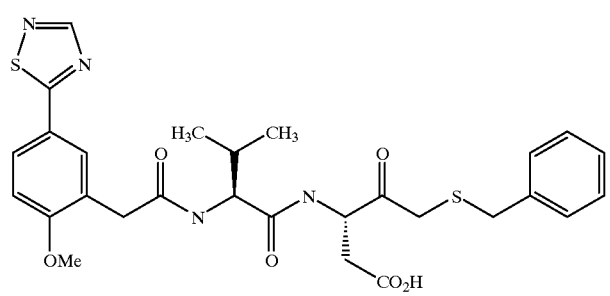
142 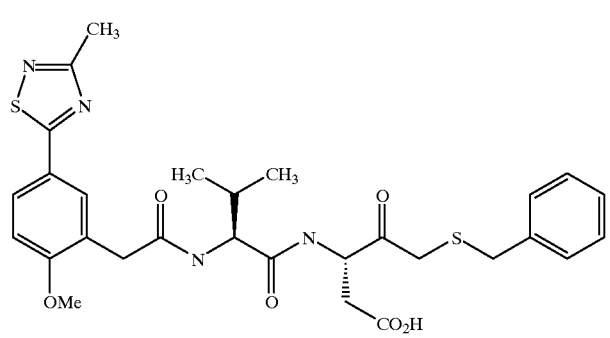

TABLE I-continued
143 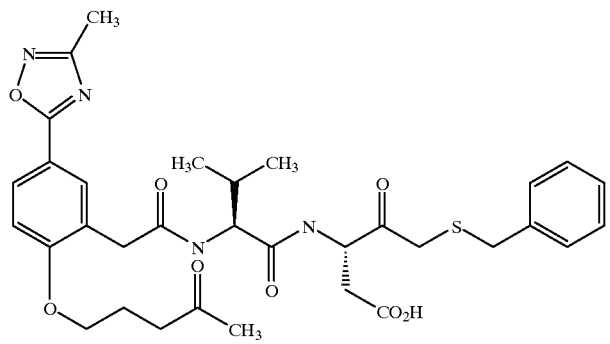
144 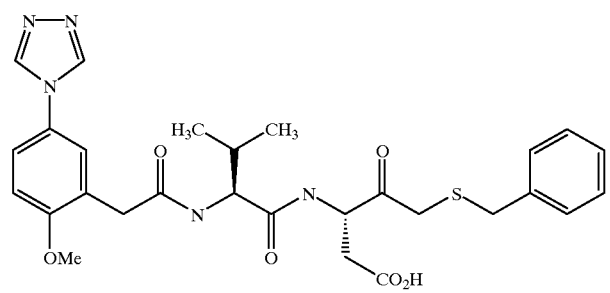
145 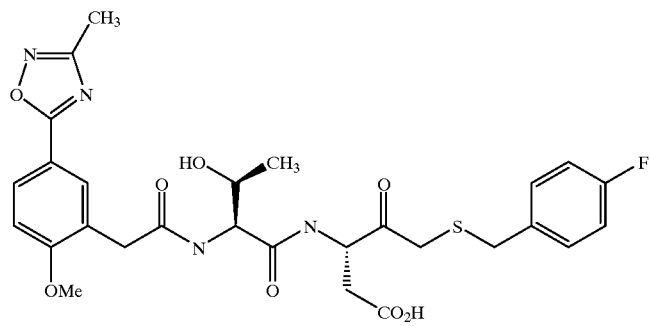
146 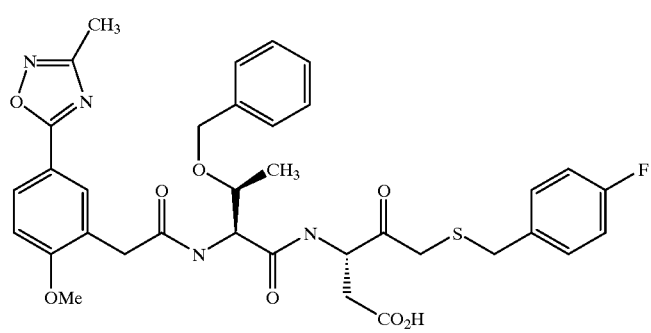

147 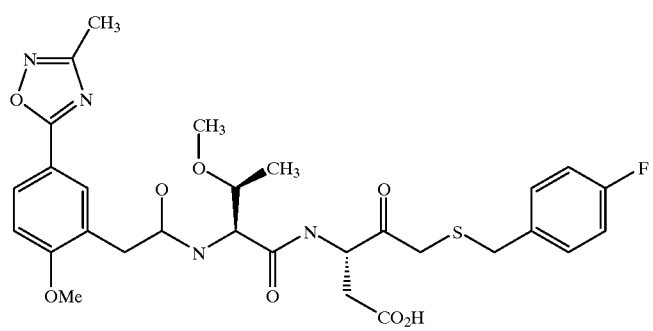
148 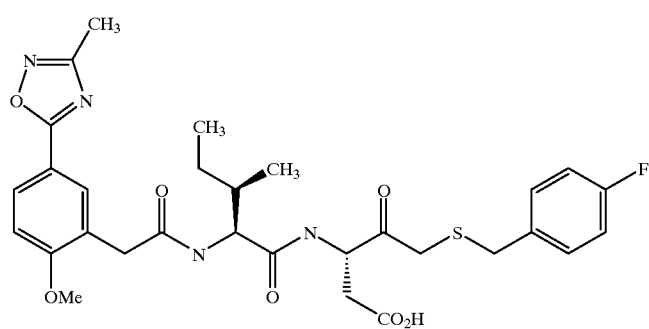
149 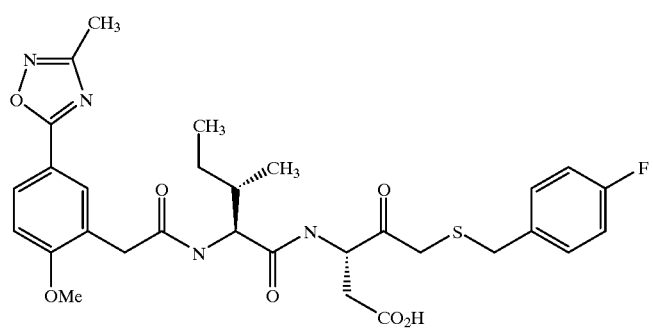
150 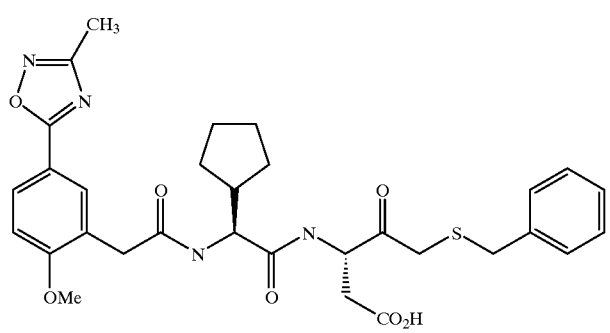

TABLE I-continued

151

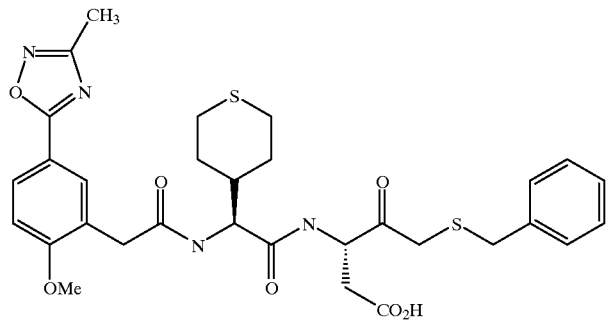

152

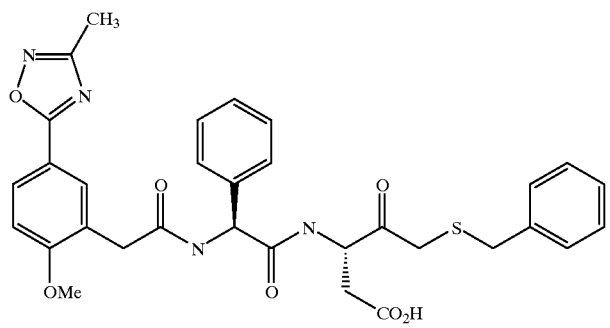

The compounds described herein, and in particular, in Table I, are intended to include salts, enantiomers, esters and hydrates, in pure form and as a mixture thereof. Also, when a nitrogen atom appears, it is understood sufficient hydrogen atoms are present to satisfy the valency of the nitrogen atom.

While chiral structures are shown below, by substituting into the synthesis schemes an enantiomer other than the one shown, or by substituting into the schemes a mixture of enantiomers, a different isomer or a racemic mixture can be achieved. Thus, all such isomers and mixtures are included in the present invention.

In another embodiment, the invention encompasses a method of treating a caspase-3 mediated disease in a mammalian patient in need of such treatment, comprising administering to said patient a compound of formula I in an amount effective to treat said caspase-3 mediated disease.

In another embodiment, the invention encompasses a method of treating cardiac and cerebral ischemia/ reperfusion injury (e.g. stroke), type I diabetes, immune deficiency syndrome (including AIDS), cerebral and spinal cord trauma injury, organ damage during transplantation, alopecia, aging, Parkinson's disease, Alzheimer's disease, Down's syndrome, spinal muscular atrophy, multiple sclerosis and neurodegenerative disorders, comprising administering to a mammalian patient in need of such treatment an effective amount of a compound of formula I.

In another embodiment, the invention encompasses a method of treating acute disorders, including cardiac and cerebral ischemia/ reperfusion injury (e.g. stroke), spinal cord injury and organ damage during transplantation, in a mammalian patient in need of such treatment, comprising administering to said patient a compound of formula I in an amount effective to treat said acute disorder.

In another embodiment, the invention encompasses a method of treating chronic disorders, including neurodegenerative diseases (e.g. Alzheimer's, polyglutamine-repeat disorders, Down's, spinal muscular atrophy, multiple sclerosis), immunodeficiency (e.g. HIV), diabetes, alopecia and aging, in a mammalian patient in need of such treatment, comprising administering to said patient a compound of formula I in an amount effective to treat said chronic disorder.

In another embodiment, the invention encompasses a method of treating a caspase-3 mediated disease in a mammalian patient in need of such treatment, comprising administering to said patient a compound of formula I in an amount effective to treat said caspase-3 mediated disease.

In particular, these compounds are preferably useful to treat, prevent or ameliorate in mammals and especially in humans, diseases including but not limited to:

cardiac and cerebral ischemia/reperfusion injury (e.g. stroke)

type I diabetes immune deficiency syndrome (including AIDS)

cerebral and spinal cord trauma injury organ damage during transplantation alopecia aging Parkinson's disease Alzheimer's disease Down's syndrome spinal muscular atrophy multiple sclerosis neurodegenerative disorders.

The compound is adminstered to a mammalian patient in need of such treatment or prevention an amount of a compound as described herein that is effective to treat or prevent the disease or condition.

The compounds described typically contain asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

The pharmaceutical compositions of the present invention comprise a compound of formula I as an active ingredient or a pharmaceutically acceptable salt thereof in combination with a pharmaceutically acceptable carrier, and optionally other therapeutic ingredients. The term "pharmaceutically acceptable salts" refers to salts prepared from pharmaceutically acceptable bases including inorganic bases and organic bases. Representative salts derived from inorganic bases include aluminum, ammonium, calcium, copper, ferric, ferrous, lithium, magnesium, manganic salts, manganous, ammonium, potassium, sodium, zinc and the like. Particularly preferred are the calcium, magnesium, potassium, and sodium salts. Representative salts derived from pharmaceutically acceptable organic bases include salts of primary, secondary and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Examples of such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric and tartaric acids.

In the discussion of methods of treatment which follows, reference to the compounds of formula I are meant to also include the pharmaceutically acceptable salts.

The ability of the compounds of formula I to inhibit caspase-3 make them useful research tools in the field of apoptosis.

The magnitude of therapeutic dose of a compound of formula I will, of course, vary with the nature of the severity of the condition to be treated and with the particular compound of formula I and its route of administration and vary upon the clinician's judgement. It will also vary according to the age, weight and response of the individual patient. An effective dosage amount of the active component can thus be determined by the clinician after a consideration of all the criteria and using is best judgement on the patient's behalf. A representative dose will range from 0.001 mpk/d to about 100 mpk/d.

An ophthalmic preparations for ocular administration comprising 0.001–1% by weight solutions or suspensions of the compounds of formula I in an acceptable ophthalmic formulation may be used.

Any suitable route of administration may be employed for providing an effective dosage of a compound of the present invention. For example, oral, parenteral and topical may be employed. Dosage forms include tablets, troches, dispersions, suspensions, solutions, capsules, creams, ointments, aerosols, and the like.

The compositions include compositions suitable for oral, parenteral and ocular (ophthalmic). They may be conveniently presented in unit dosage form and prepared by any of the methods well-known in the art of pharmacy.

In practical use, the compounds of formula I can be combined as the active ingredient in intimate admixture with a pharmaceutical carrier according to conventional pharmaceutical compounding techniques. The carrier may take a wide variety of forms depending on the form of preparation desired for administration. In preparing the compositions for oral dosage form, any of the usual pharmaceutical media may be employed, such as, for example, water, alcohols, oils, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case or oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil emulsion. Such compositions may be prepared by any of the methods of pharmacy but all methods include the step of bringing into active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. For example, each dosage unit may contain from about 0.01 mg to about 1.0 g of the active ingredient.

Method of Synthesis

Compounds of the present invention are conveniently prepared using the procedures described generally below and more explicitly described in the Example section thereafter.

Scheme 1
Preparation of Bromomethylketone 1

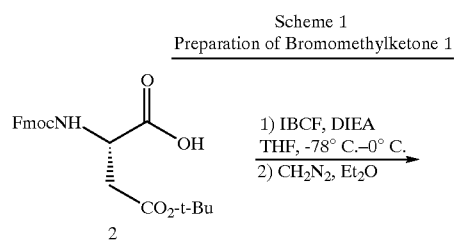

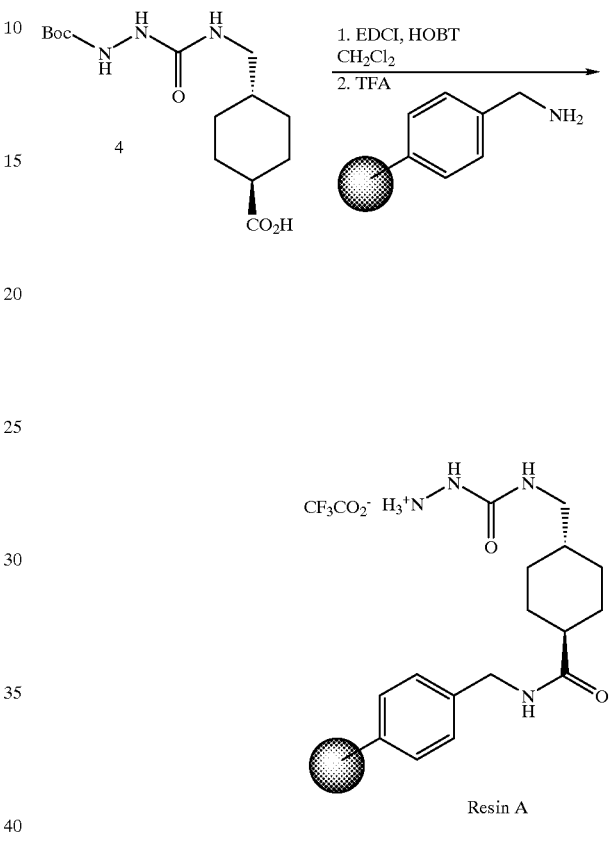

Bromomethylketone 1 is prepared as illustrated in Scheme 1. Reaction of N-fluorenylmethyloxycarbonyl-L-aspartic acid β-tert-butyl ester (Fmoc-L-Asp (OtBu)—OH) (2) (Novabiochem) with iso-butyl chloroformate (IBCF) followed by treating the reaction mixture with an excess of diazomethane yields the diazomethylketone intermediate 3. This intermediate is subjected in situ to a 1:1 mixture of AcOH and 45% aqueous hydrobromic acid (HBr) to give compound 2 as a white powder.

The semicarbazide Resin A is prepared according to Scheme 2. Treatment of compound 4 (Webb et al, J. Am. Chem. Soc. 114, 3156 (1992)) with a commercial amino-Merrifield resin in the presence of EDCI and HOBT in dichloromethane followed by removal of the Boc group with trifluoroacetic acid (TFA) in dichloromethane afforded Resin A.

The general procedure for the solid phase synthesis of dipeptide I incorporating either a sulfide P1' sulfur side chain is illustrated in Scheme 3. Bromomethyl ketone 1 is mixed with Resin A in THF in the presence of AcOH overnight to furnish Resin B. Nucleophilic displacement with an appropriate thiol in the presence of suitable bases give Resin C as shown. The Fmoc group on Resin C is cleaved with 20% (v) piperidine in DMF and the resultant resin reacted with FmocHNCR[1](R[2])COOH using O-(7-Azabenzotriazol-1-yl) N,N,N',N'-tetramethyluronium hexafluorophosphate (HATU) as the activating agent and diisopropylethylamine (DIEA) as the base, affording Resin D. Resin D is processed in a similar fashion to furnish Resin E. The final dipeptide I is released from solid support by treating Resin E with trifluoroacetic acid (TFA) in water (9/1, v/v).

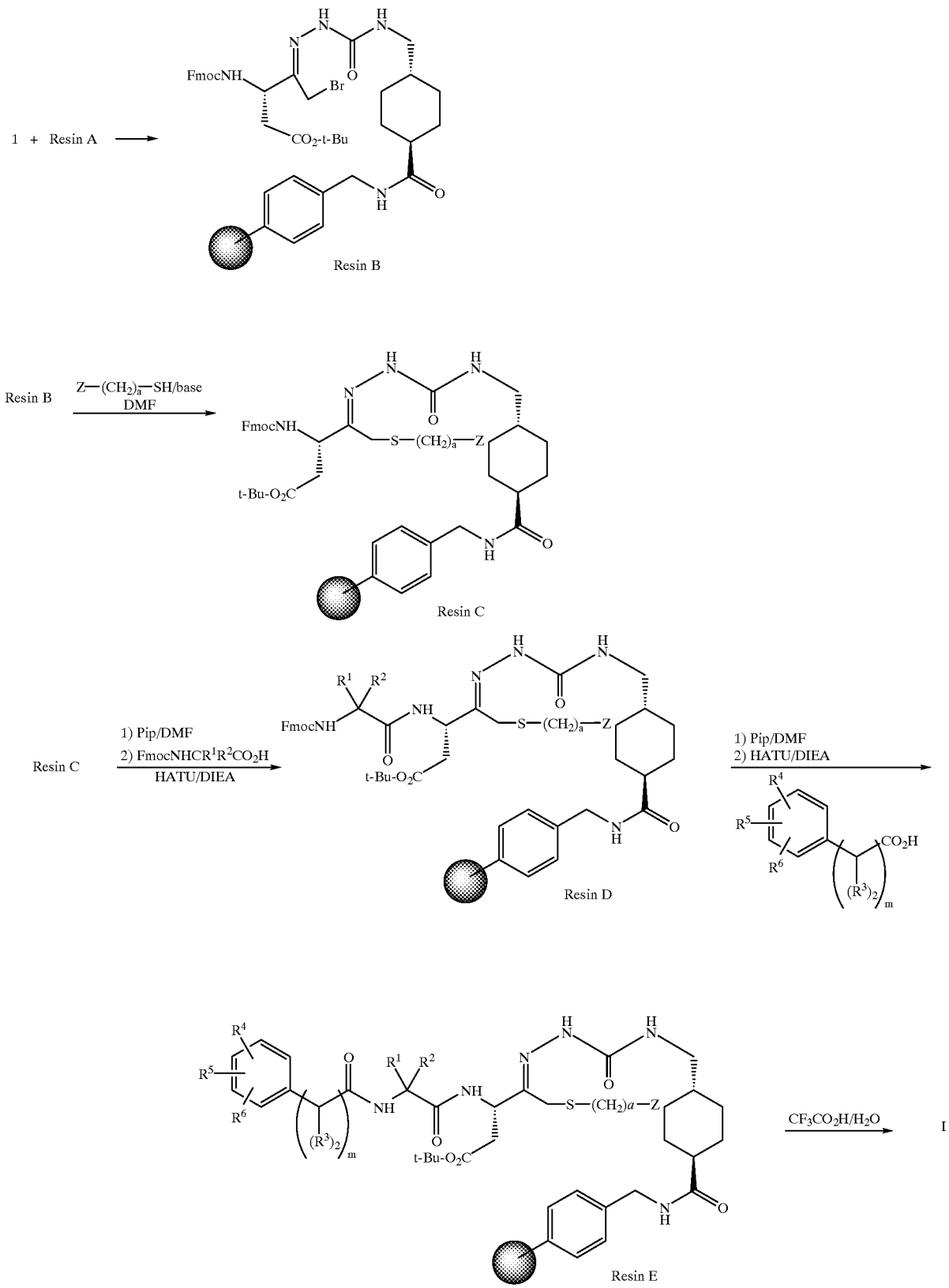
Scheme 3
General Scheme for preparing didpeptide of structure

The invention is further illustrated using the following non-limiting examples.

EXAMPLE 1

(3S)-5-(Benzylsulfanyl)-3-{[(2S)-2-(12-(2,5-Dimethoxyphenyl)Acetyl)Amino)-3-Methylbutanoyl]amino}-4-Oxopentanoic Acid

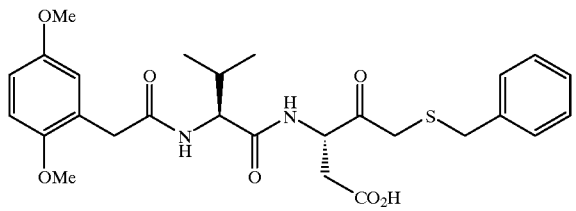

Step 1: t-Butyl (3S)-5-bromo-3-[(9H-9-fluorenylmethoxy)carbonyl]amino-4-oxo-pentanoate (1)

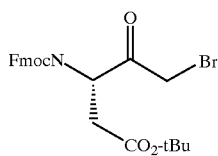

To a solution of N-Fmoc-L-aspartic acid β-tert-butyl ester (21.0 g, 51.0 mmol) in 300 mL of tetrahydrofuran (THF) at −78 °C. was added N-methylmorpholine (NMM, 7.9 mL, 71.4 mmol) followed by isobutyl chloroformate (IBCF, 8.6 mL, 66.3 mmol). After stirring for 30 minutes at −78° C, this mixture was warmed to −15° C. for 15 minutes. To the mixture was then added twice, in a 10 minutes interval, a solution of diazomethane in ether (1 M, 40 mL) with stirring. The mixture was allowed to warm to 0° C. and to it was added another 60 mL of the diazomethane solution. The solution was then warmed to room temperature and stirred for 10 minutes, recooled back to 0° C. and treated with a solution of HBr(48% aqueous)/AcOH (1/1, v/v, 100 mL) for 5 minutes, diluted with ethyl acetate and water. The organic phase was separated, washed with water and brine, dried over magnesium sulfate, filtered and concentrated. The crude product was purified by flash chromatography. Eluting with hexanes/ethyl acetate (3:1) afforded the desired product as a white powder (20 g, 81% yield).

$^1$H NMR (400 MHz, acetone-$d_6$): δ 7.85 (d, 2H), 7.69 (d, 2H), 7.41 (t, 2H), 7.32 (t, 2H), 7.02 (bd, 1H, NH), 4.70 (dd, 1H), 4.51–4.41 (m, 2H), 4.38–4.30 (2×d, 2H), 4.25 (t, 1H), 2.85 (dd, 1H), 2.70 (dd, 1H), 1.41 (s, 9H).

Step 2: Preparation of Resin A

A suspension of amino-Merrified resin (Novabiochem, 30 grams, 31.2 mmol), acid 4 (14.7 g, 46.8 mmol), EDCI (10.77 g, 56.12 mmol) and HOBT (8.6 g, 56.16 mmol) in DMF (240 mL) was shaken on a orbital shaker at 190 rpm overnight. The mixture was filtered and the residual resin washed sequentially with DMF, methanol, dichloromethane and methanol and dried under vacuum. The resin then was suspended in a solution of TFA/dichloromethane (1:2, 300 mL) and shaken for 2 h on a orbital shaker. The suspension was filtered, washed with dichloromethane (5×) and methanol (5×) and then dried under vacuum overnight to yield Resin A (40.5 g, 0.81 mmol/g).

Step 3: Loading of ketone 1 to Resin A

A suspension of ketone 1 (4.5 g, 9.22 mmol) and Resin A (8.8 g, 7.13 mmol) in THF (70 mL) in the presence of AcOH (0.2 mL, 3.4 mmol) was shaken on a orbital shaker at 200 rpm overnight. The suspension was filtered and residual resin was washed sequentially with THF, dichloromethane, ethyl acetate and diethyl ether. Drying under high vacuum afforded Resin B (11.7 g).

Step 4: preparation of Resins F and G

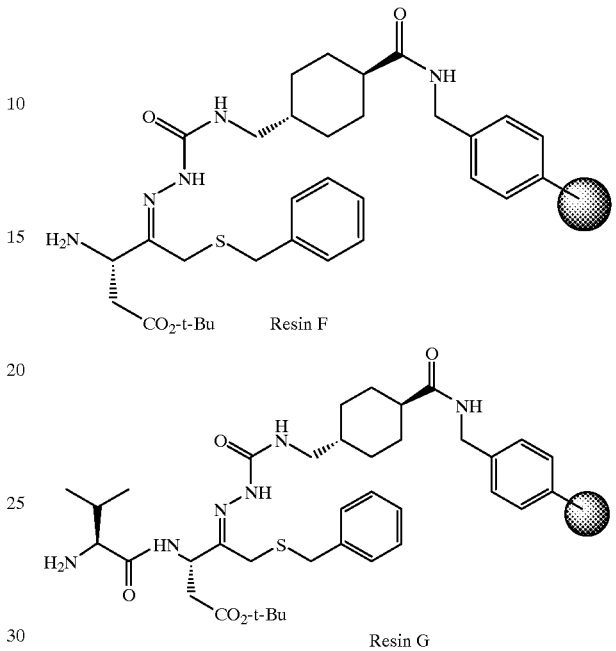

To a suspension of Resin B (1.6 g) in DMF (6 mL) in a fritted reservoir was added a solution of benzylmercaptan (5.5 mL, 1 M in DMF) and N,N-diisopropylethylamine (DIEA) and the mixture was rotated on a disc (Glas-Col™) for 3 h and filtered. The resin was washed with DMF and then subjected to a solution of 20% piperidine in DMF for 20 minutes and then washed sequentially with DMF, methanol, dichloromethane and methanol and dried under high vacuum to afford Resin F. 0.5 grams of this resin was reacted with Fmoc-Valine-OH (0.61 g) and HATU (0.68 g) and DIEA (0.31 mL) in DMF (4 mL) for 2 h and washed with DMF. The resulting resin was then treated with a solution of 20% (v) piperidine in DMF and washed again with DMF, methanol, dichloromethane and methanol and dried under vacuum to furnish Resin G.

A portion (0.5 g) of Resin G thus obtained was treated with 2,5-dimethoxyphenylacetic acid (0.294 g), HATU (0.37 g) and DIEA (0.26 mL) in DMF (4 mL) for 2 h and washed sequentially with DMF, methanol, dichloromethane, ethyl acetate and ether. A cocktail consisting of TFA and water (9:1, 10 mL) was then added and the mixture rotated for 1 h and filtered. The filtrate was collected and residual resin washed with dichloromethane and acetonitrile. The filtrate and washing solutions were combined, concentrated in vacuo and triturated with ether to afford the title compound as a white powder (136 mg).

$^1$H NMR (400 MHz, acetone-$d_6$): δ 7.85 (br d, 1H, NH), 7.34–7.23 (m, 5H), 7.02 (br d, 1H, NH), 6.88 (d, 1H), 6.84 (d, 1H), 6.77 (dd, 1H), 4.92 (dd, 1H), 4.28 (dd, 1H), 3.80 (s, 3H), 3.78 (s, 3H), 3.70 (dd, 2H), 3.54 (d, 1H), 3.47 (d, 1H), 3.43 (d, 1H), 3.28 (d, 1H), 2.90 (dd, 1H), 2.75 (dd, 1H), 2.07 (m, 1H), 0.88 (d, 3H), 0.84 (d, 3H); MS (−APCI) calculated for $C_{27}H_{34}N_2O_7S$: 530.2; found (M−1): 529.1.

EXAMPLE 2

(3S)-5-[(2-Chloro-6-Fluorobenzyl)Sulfanyl]-3-{
[(2S)-2-({2-[2-Ethoxy-5-(Methanesulfonyl)Phenyl]
Acetyl}Amino)-3-Methylbutanoyl]Amino}-4-
Oxopentanoic Acid

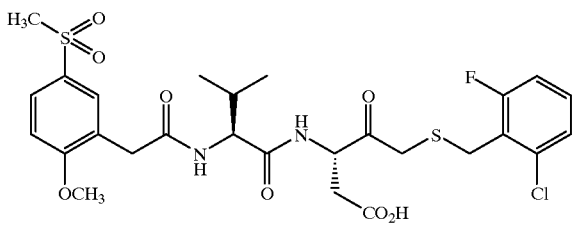

Step 1: Preparation of 5-methanesulfonyl-2-methoxybenzyl bromide (5)

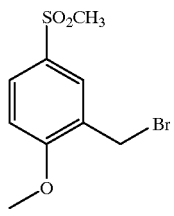

A mixture of 5-methanesulfonyl-2-methoxytoluene (for preparation, see: U.S. Pat. No. 2,803,580 and Monatsh. Chem. 91, 57 (1960)) (298 mg), NBS (265 mg) and benzoylperoxide (catalytic amount) in $CCl_4$ was irradiated with a sun lamp under reflux under a nitrogen atmosphere for 2 hours and cooled to room temperature. The solid was filtered off and the filtrate was concentrated and subjected to silica gel chromatogiraphy (hexanes/ethyl acetate 3:1) to give bromide 5 as a white solid.

$^1$H NMR (400 MHz, acetone-$d_6$): δ 7.98 (d, 1H), 7.90 (dd, 1H), 7.27 (d, 1H), 4.69 (s, 2H), 4.05 (s, 3H), 3.08 (s, 3H).

Step 2: preparation of 5-methanesulfonyl-2-methoxyphenylacetic acid (6)

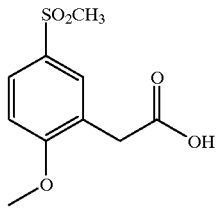

To a solution of bromide 5 (334 mg) in ethanol (10 mL) was added a solution of sodium cyanide (64 mg) in $H_2O$ (2 mL) and the resulting mixture was heated to reflux for 1 hour. After cooled to room temperature, the mixture was quenched with saturated ammonium chloride and extracted with ethyl acetate. The organic phase was washed with brine, dried over magnesium sulfate and filtered. The filtrate was concentrated in vacuo to give the desired compound as a yellow solid (250 mg). $^1$H NMR (400 MHz, acetone-$d_6$) δ 7.96–7.92 (m, 2H), 7.30 (d, 1H), 4.03 (s, 3H), 3.92 (s, 2H), 3.10 (s, 3H).

The nitrile from above was dissolved in a mixture of AcOH (8 mL), $H_2O$ (8 mL) and $H_2SO_4$ (8 mL) and the mixture was heated to reflux for 3.5 hours. After cooling to room temperature, the mixture was diluted with $H_2O$ and extracted with ethyl acetate. The organic phase was washed with $H_2O$, brine, dried over magnesium sulfate and concentrated. The crude product was subjected to silica gel chromatography. Eluting with methanol and dichloromethane (1:10) afforded the desired acid 6.

$^1$H NMR (400 MHz, acetone-$d_6$): δ 7.84 (dd, 1H), 7.81 (d, 1H), 7.21 (d, 1H), 3.94 (s, 3H), 3.70 (s, 2H), 3.05 (s, 3H).

Step 3: preparation of Resins H and I

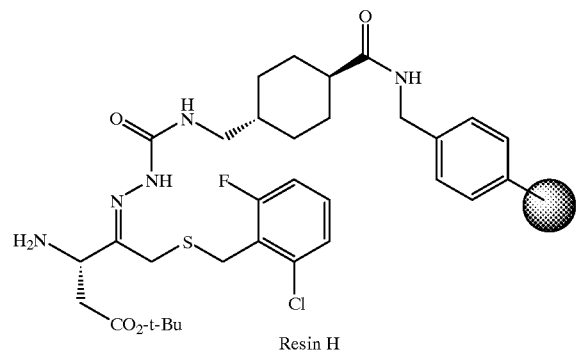

Resin H

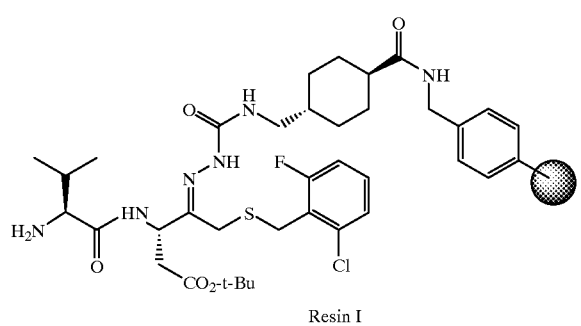

Resin I

Resins H and I were prepared in a similar manner as described for Resins F and G respectively.

Step 4: Title compound

Coupling of 5-methanesulfonyl-2-methoxyphenylacetic acid (6) to Resin I and subsequent cleavage were carried out as described for example 1 to give the title compound.

¹H NMR (400 MHz, acetone-d₆): δ 7.96 (bd, 1H, NH), 7.83–7.75 (m, 2H), 7.40–7.25 (m, 3H, containing one NH), 7.20 (7.10 (m, 2H), 4.90 (dd, 1H), 4.30 (dd, 1H), 3.95 (s, 3H), 3.89 (s, 2H), 3.70–3.55 (m, 4H), 2.92 (dd, 1H), 2.80 (dd, 1H), 2.13 (m, 1H), 0.93–0.85 (m, 6H); MS (–APCI): m/z 629.4 (M–1).

EXAMPLE 3

(3S)-5-(Benzylsulfanyl)-3-({(2S)-2-[(2-{2-Ethoxy-5-(2-Methoxy-2-Oxoethoxy)Phenyl}Acetyl)Amino]-3-Methylbutanoyl}Amino)-4-Oxopentanoic Acid

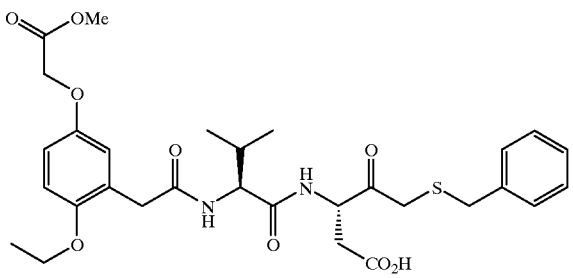

Step 1: 2,5-dihydroxyphenylacetic acid v-lactone t-butyldimethylsilyl ether (7)

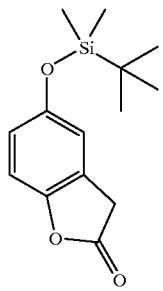

To a solution of 2,5-dihydroxyphenylacetic acid v-lactone (3.0 g) in DMF (20 mL) was added imidazole (1.77 g) and t-butyldimethylsilyl chloride (3.62 g) and the mixture stirred at room temperature for 3 hours. The solution was then diluted with H₂O (100 mL) and extracted with diethyl ether (3×100 mL). The organic layer was washed with brine, dried over magnesium sulfate and filtered. The filtrate was concentrated in vacuo and the residue was subjected to silica gel chromatography. Eluting with ethyl acetate in hexanes (1:5) gave compound 7 as a viscous oil.

¹H NMR (400 MHz, acetone-d₆): δ 6.97 (d, 1H), 6.89 (d, 1H), 6.79 (dd, 1H), 3.80 (s, 2H), 0.90 (s, 9H), 0.21 (s, 6H).

Step 2: preparation of Resin J

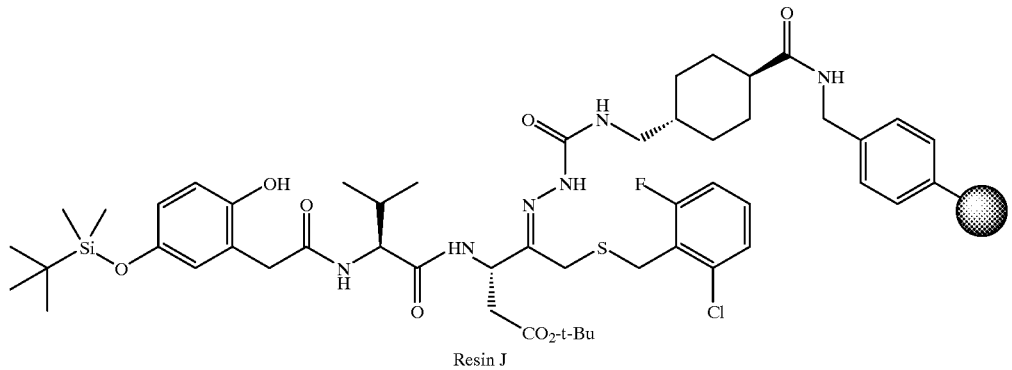

Resin J

A suspension of Resin G (16 g, 9.6 mmol) and lactone 7 (12.7 g, 48 mmol) in DMF (100 mL) in the presence of 4-N-dimethylaminopyridine (DMAP) (5.8 g, 48 mmol) was shaken on a orbital shaker at 45–50° C. overnight and filtered. The resin was washed sequentially with DMF, DMF/H₂O (1:1), H₂O, DMF/H₂O, DMF, THF, ethyl acetate and ether and then dried under vacuum to yield Resin J.

Step 3: preparation of Resin K

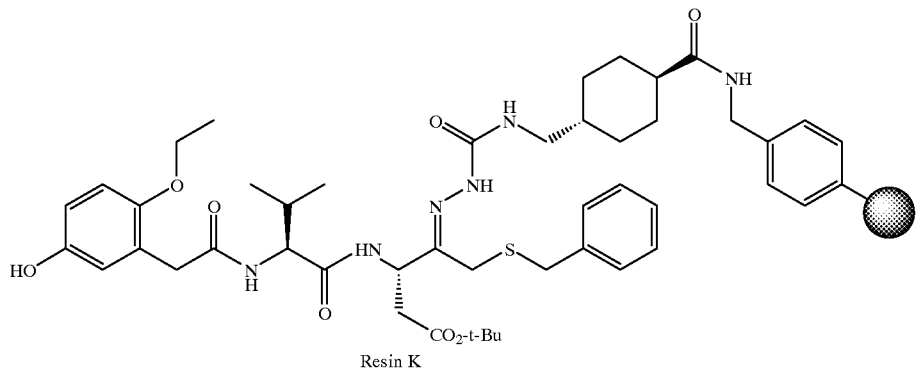

Resin K

Resin J (3 g, 1.8 mmol) was first suspended in a mixture of dichloromethane/toluene (1:1, 28 mL) in a fritted reservoir. To this suspension was then added ethanol (0.53 mL, 9 mmol) and reagent 8 (3.45 g, 9 mmol) (see: Castro, J. L. and Matassa, V. G., J. Org. Chem. 59, 2289 (1994)) and the reservoir was capped and rotated on a Glas-Col™ disc overnight. The mixture was then filtered, washed as described for Resin J. The resultant resin was treated with TBAF (18 mL, 1M solution in THF) in THF (12 mL) in the presence of AcOH (1.1 mL) for 1 hour at room temperature. The mixture was filtered and the resin was washed with DMF, DMF/$H_2O$, $H_2O$ (containing 20% AcOH), DMF, THF, ethyl acetate ether and dried under vacuum to afford Resin K.

dichloromethane yielded the title compound as a light yellow solid (from methanol/$H_2O$).

$^1$H NMR (500 MHz, acetone-$d_6$): δ 7.90 (br d, 1H, NH), 7.36–7.27 (m, 2H), 7.13 (t, 1H), 7.05 (bd, 1H, NH), 6.90–6.85 (m, 2H), 6.77 (dd, 1H), 4.90 (dd, 1H), 4.63 (s, 2H), 4.29 (dd, 1H), 4.02 (q, 2H), 3.89 (bs, 2H), 3.72 (s, 3H), 3.65 (d, 1H), 3.59–3.53 (m, 2H), 3.47 (d, 1H), 2.90 (dd, 1H), 2.78 (dd, 1H), 2.08 (m, 1H), 1.36 (t, 3H), 0.88–0.80 (2×d, 6H). MS (—APCI): m/z 653.6 (M−1).

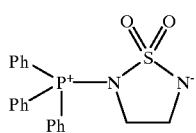

8

Step 4: title compound

In a fritted reservoir charged with Resin K (1.5 g) was added dichloromethane (8 mL) and toluene (8 mL). To this suspension was then added methyl glycolate (405 mg) and reagent 8 (1.72 g) and the suspension was rotated for 2 hours at room temperature. This procedure was repeated once and the resin was filtered, washed with DMF, DMF/$H_2O$, $H_2O$, DMF/$H_2O$, THF, ethyl acetate and ether. A portion of this resin (1 g) was treated with a solution of TFA/$H_2O$ (9:1, 8 mL) for 1 hour and filtered. The filtrate was collected and the residual resin was washed with dichloromethane and acetonitrile. The filtrate and washing solutions were combined and concentrated. The crude product was purified by silica gel chromatography. Eluting with methanol (5–10%) in

EXAMPLE 4

(3S)-5-[(2-Chloro-6-Fluorobenzyl)Sulfanyl]-3-({(2S)-2-[(2-{2-Ethoxy-5-(2-Isopropoxy-2-Oxoethoxy)Phenyl}Acetyl)Amino]-3-Methylbutanoyl}Amino)-4-Oxopentanoic Acid

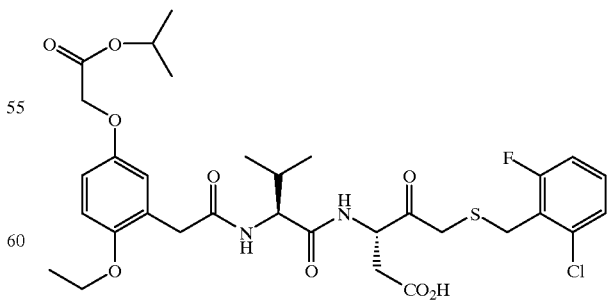

Step 1: preparation of Resin L

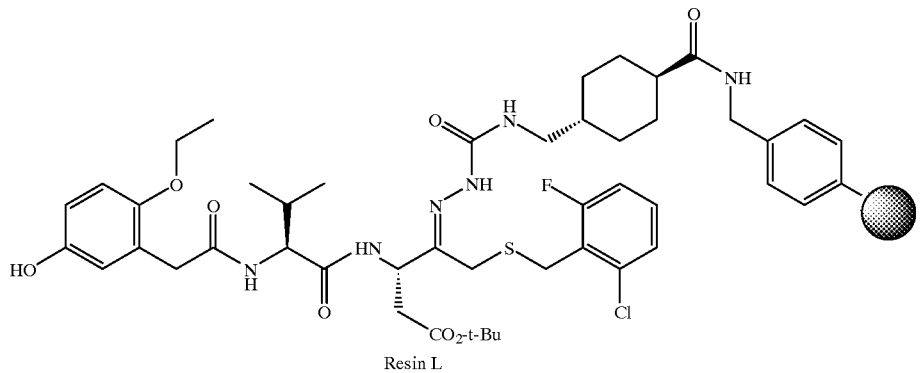

Resin L

Resin L was prepared similarly as described for Resin K.
Step 2: title compound

In a fritted reservoir charged with Resin L (200 mg) in THF was added a solution of TMSOK (0.36 mL, 1 M solution in THF) and the suspension was mixed for 1 minute. To the mixture was then added iso-propyl bromoacetate (0.078 mL) via a syringe and the mixture was rotated overnight. After filtration, the resin was washed with THF,. THF/H$_2$O/AcOH (4:1:1), H$_2$O, THF, ethyl acetate and ether. Cleaving the washed resin with a cocktail of TFA/IH$_2$O (9:1, 2 mL) as described followed by subjecting the crude product to silica gel chromatography (5% methanol in dichloromethane) afforded the title compound (22 mg).

$^1$H NMR (500 MHz, acetone-d$_6$/CD$_3$OD): δ 7.50 (br s, 1H, NH), 7.31–7.22 (m, 2H), 7.08 (t, 1H), 6.85–6.83 (m, 2H), 6.74 (dd, 1H), 5.00 (m, 1H), 4.92 (m, 1H), 4.56 (s, 2H), 4.25 (m, 1H), 4.00 (m, 2H), 3.88 (s, 2H), 3.70–3.55 (m, 3H), 3.48 (d, 1H), 2.80–2.62 (m, 2H), 2.08 (m, 1H), 1.34 (t, 3H), 1.20 (d, 6H), 0.89–0.82 (2×d, 6H). MS (–APCI): m/z 681.9 (M–1).

EXAMPLE 5

(3S)-5-[(2-Chloro-6-Fluorobenzyl)Sulfanyl]-3-
({2S)-2-[(2-{2-Ethoxy-5-(2-Hydroxy-2-Oxoethoxy)
Phenyl}Acetyl)Amino]-3-Methylbutanoyl}Amino)-
4-Oxopentanoic Acid

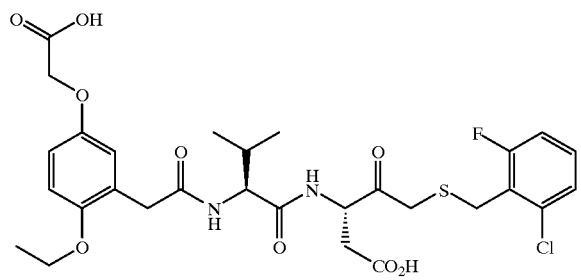

To a suspension of Resin L (110 mg) in DMF (1 mL) in a fritted reservoir was added TMSOK (0.33 mL) and the mixture was mixed for 2 minutes. To the suspension was added t-butyl bromoacetate (0.058 mL) and the mixture was rotated overnight and filtered. The resin was washed as stated previously and cleaved with THF/H$_2$O. The crude product was crystallized from dichloromethane/ ether to give a light yellow solid.

$^1$H NMR (400 MHz, acetone-d$_6$): δ 7.92 (br d, 1H, NH), 7.39–7.29 (m, 2H), 7.15 (t, 1H), 6.90 (m, 1H), 6.82–6.64 (m, 2H), 4.90 (m, 1H), 4.61 (s, 2H), 4.33 (m, 1H), 4.02 (m, 2H), 3.88 (s, 2H), 3.68–3.40 (m, 4H), 2.90 (dd, 1H), 2.79 (dd, 1H), 2.08 (m, 1H), 1.38 (m, 3H), 0.88–0.80 (m, 6H). MS (–APCI): 639.5 (M–1).

EXAMPLE 6

(3S)-5-[(2-Chloro-6-Fluorobenzyl)Sulfanyl]-3-{
[(2S)-2-({2-[2-Ethoxy-5-{Pyrimidyloxy-2-
Yl}Phenyl]Acetyl}Amino)-3-Methylbutanoyl]
Amino}-4-Oxopentanoic Acid

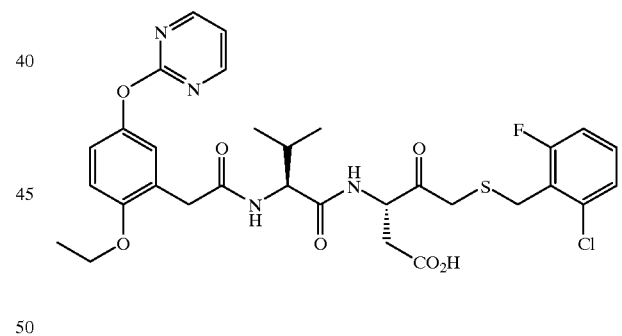

To a suspension of Resin L (120 mg) in DMF (1.5 mL) in a fritted reservoir was added TMSOK (0.37 mL, 1 M solution in THF) and the mixture was mixed for 2 minutes. To the suspension was then added 2-chloropyrimidine (57 mg) and the reservoir was rotated overnight and then filtered. The resin was washed and treated with a cocktail of TFA/H$_2$O as described previously to furnish the title compound.

$^1$H NMR (400 MHz, acetone-d$_6$): δ 8.55 (d, 2H), 7.90 (br d, 1H, NH), 7.35–7.27 (m, 2H), 7.20–7.00 (m, 6H), 4.89 (m, 1H), 4.30 (m, 1H), 4.08 (m, 2H), 3.88 (s, 2H), 3.68–3.52 (m, 4H), 2.88 (dd, 1H), 2.78 (dd, 1H), 2.08 (m, 1H), 1.39 (t, 3H), 0.90–0.81 (2×d, 6H). MS (–APCI): m/z 659.6 (M–1).

EXAMPLE 7

(3S)-5-[(2-Chloro-6-Fluorobenzyl)Sulfanyl) ]-3-({(2S)-2-[(2-{5-[(E)-3-Hydroxy-3-Oxo-1-Propenyl]-2-Methoxyphenyl}Acetyl)Amino]-3-Methylbutanoyl}Amino)-4-Oxopentanoic Acid

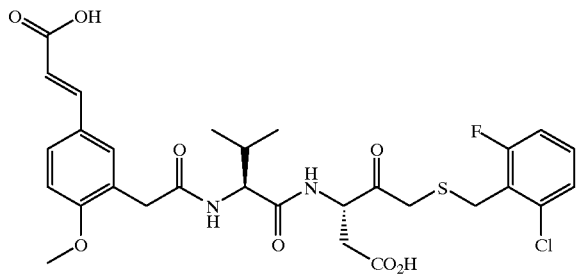

Step 1: (E)-5-(3-t-butoxy-3-oxo-1-propenyl)-2-methoxyphenylacetic

9

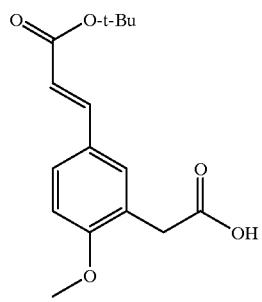

A mixture of methyl 5-bromo-2-methoxyphenylacetate (0.6 g, for its preparation, see: Paty et al, Bull. Soc. Chim. Fr. 5, 1676 (1938)), t-butyl acrylate (3.4 mg) and Pd(OAc)3 (0.052 g) in DNW (2 mL) and triethylamine (TEA, 2 mL) was degased under high vacuum at −196° C. (liquid nitrogen) twice and then sealed under vacuum. The tube was heated to 110° C. (caution: use safety shield!) for 20 hours and cooled to −78° C. The seal tube was opened to atmospheric pressure and the content was diluted with $H_2O$ (100 mL) and extracted with ether (3×100 mL). The organic extracts were combined, washed with water and brine, and dried over magnesium sulfate. After filtration and concentration, the crude product was purified by silica gel chromatography. Eluting with ethyl acetate (5–15%)/hexanes yield the desired compound (0.49 g). $^1$HNMR (400 MHz, acetone-dr,): δ 7.50–7.48 (m, 3H), 7.00 (d, 1H), 6.28 (d, 1H), 3.87 (s, 3H), 3.65 (s, 3H), 3.64 (s, 2H), 1.50 (s, 9H). A mixture of the ester from above (100 mg), LiOH monohydrate (27 mg) in ethanol/$H_2O$ (3:1, 4 mL) was stirred at room temperature for 5 hours. The ethanol was evaporated in vacuo and the residue acidified with 1 N HCl to pH~1 and extracted with ethyl acetate. The organic phase was washed with brine, dried over magnesium sulfate and concentrated to give acid 9 (85 mg).

$^1$H NMR (500 MHz, acetone-$d_6$): δ 7.57–7.50 (m, 3H), 7.00 (d, 1H), 6.80 (d, 1H), 3.84 (s, 3H), 3.63 (s, 2H).

Step 3: title compound

Acid 9 from above (85 mg) was coupled to Resin I (100 mg) as discussed previously and the coupled resin was treated with TFA/$H_2O$ to afford the title compound (28 mg).

$^1$H NMR (500 MHz, acetone-$d_6$): δ 7.90 (br d, 1H, NH), 7.62–7.50 (m, 3H), 7.357.25 (m, 2H), 7.18 (d, 1H, NH), 7.12 (t, 1H), 7.02 (d, 1H), 6.48 (d, 1H), 4.90 (m, 1H), 4.30 (m, 1H), 3.88 (s, 5H), 3.65–3.52 (m, 4H), 2.90 (dd, 1H), 2.76 (dd, 1H), 2.10 (m, 1H), 0.90–0.82 (2×d, 6H). MS (−APCI): m/z 621.7 (M−1).

EXAMPLE 8

(3S)-5-[(2-Chloro-6-Fluorobenzyl)Sulfanyl)]-3-({(2S)-2-[(2-{5-[3-Hydroxy-3-Oxo-1-Propyl]-2-Methoxyphenyl}Acetyl)Amino]-3-Methylbutanoyl}Amino)-4-Oxopentanoic Acid

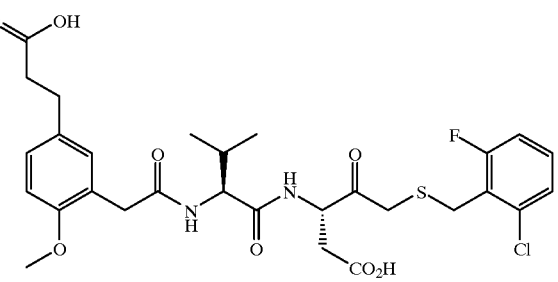

Step 1: 5-(3-t-butoxy-3-oxo-1-propyl)-2-methoxyphenylacetic acid (10)

10

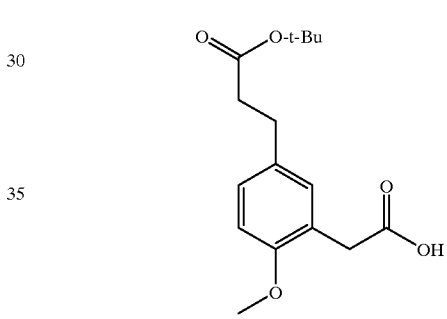

Methyl (Z)-5-t-butoxycarbonylvinyl-2-methoxyphenylacetate (250 mg, from above) in ethyl acetate (5 mL) in the presence of Pd/C (10% Pd content, 44 mg) was subjected to a Parr apparatus under 50 PSI of hydrogen gas for 1 hour. The mixture was filtered through celite and the filter cake washed with ethyl acetate. The filtrate and washing solution were combined and concentrated to give the desired product. 1H NMR (400 MHz, acetone-$d_6$): δ 7.10 (d, 1H), 7.04 (s, 1H), 6.88 (d, 1H), 3.76 (s, 3H), 3.57 (s, 3H), 3.55 (s, 2H), 2.78 (t, 2H), 2.48 (t, 2H), 1.40 (s, 9H). This compound (100 mg) was then treated with LiOH monohydrate (27 mg) in ethanol/$H_2O$ (3:1, 4 mL) for 5 hours. The ethanol was evaporated on vacuo and the residual acidified to pH-1 and extracted with ethyl acetate. The organic layer was washed with brine, dried over magnesium sulfate and filtered. Concentration in vacuo afforded acid 10 (80 mg) as a white solid.

$^1$H NMR (500 MHz, acetone-$d_6$): δ 7.08 (d, 1H), 7.07 (s, 1H), 6.85 (d, 1H), 3.76 (s, 3H), 3.55 (s, 2H), 2.77 (t, 2H), 2.47 (t, 2H), 1.39 (s, 9H).

Step 2: title compound

Acid 10 from above (80 mg) was coupled to Resin I (100 mg) as discussed previously and the coupled resin was treated with TFA/$H_2O$ to afford the title compound (23 mg).

EXAMPLE 9

(3S)-5-[(2-Chloro-6-Fluorobenzyl)Sulfanyl)]-3-({(2S)-2-[(2-{2-Ethoxy-5-[(E)-3-Methoxy-3-OXO-1-Propenyl]Phenyl}Acetyl)Amino]-3-Methylbutanoyl}Amino)-4-Oxopentanoic Acid

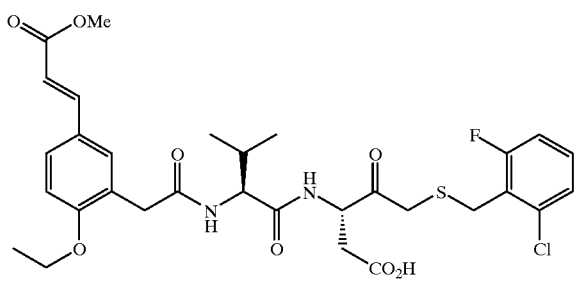

Step 1: 5-[(E)-(3-methoxy-3-oxo-1-propenyl)]-2-ethoxytoluene (11)

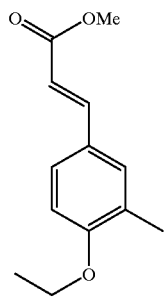

In a 250 mL RBF was charged 2-ethoxy-5-iodotoluene (5 g, 19.1 mmol, prepared from 2-hydroxy-5-iodotoluene by reacting with ethyl iodide in acetone in the presence of K₂CO₃), methyl acrylate (17 mL), P(o-tolyl)3 (1.16 g), DMF (25 mL) and TEA (25 mL). The mixture was degased under nitrogen. To the solution was added Pd(OAc)2 (0.43 g) and the mixture was heated to reflux under nitrogen for 20 hours. After cooling to room temperature, the reaction mixture was diluted with water (200 mL) and extracted with ether (2×250 mL). The ether extracts were washed with water and brine, dried over magnesium sulfate, filtered and concentrated. The crude product was purified by silica gel chromatography. Eluting with 5–20% ethyl acetate in hexanes afforded the desired product 11 (3.3 g).

¹H NMR (300 MHz, acetone-d₆): δ 7.60 (d, 1H), 7.48–7.40 (m, 2H), 6.92 (d, 1H), 4.10 (q, 2H), 3.73 (s, 3H), 2.20 (s, 3H), 1.40 (t, 3H).

Step 2: 5-[(E)-(3-methoxy-3-oxo-1-propenyl)]-2-ethoxybenzyl bromide (12)

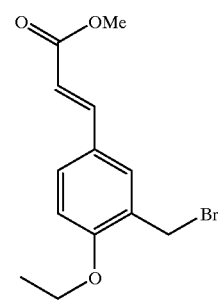

The product from above (3.3 g) was dissolved in CCl₄ (100 mL) and to the solution was added NBS (2.67 g) and a catalytic amount of benzoyl peroxide. The mixture was irradiated with a sum lamp under reflux overnight and cooled to room temperature. The solid was filtered off and the filtrate was concentrated to yield the crude product which was purified by column chromatography. Eluting with ethyl acetate/hexanes (1:9) afforded product 12 (2.59 g) as a white solid.

¹H NMR (500 MHz, acetone-d₆): δ 7.78 (s, 1H), 7.63–7.58 (m, 2H), 7.07 (d, 1H), 6.44 (d, 1H), 4.62 (s, 2H), 4.20 (q, 2H), 3.73 (s, 3H), 1.46 (t, 3H).

Step 3: 5-[(E)-(3-methxoy-3-oxo-1-prpenyl) ]-2-ethoxyphenylacetic acid (13)

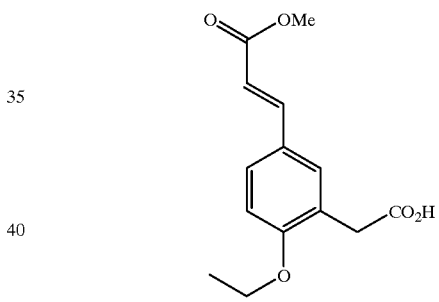

The carbonylation reaction was executed according to a modified literature procedure described by Alper, H. et al (J. Chem. Soc., Chem Commun. 167 (1986)). Thus, a mixture of bromide 12 (300 mg), [Rh(1,5-COD)Cl]₂ (50 mg) and KI (10 mg) in t-butyl formate (2 mL) was heated to 60° C. under 1 atm of CO overnight and cooled to room temperature.

The mixture was diluted with ether and filtered through celite. The filtrate was washed with saturated ammonium chloride (aqueous), brine, dried and concentrated. The crude product was purified by silica gel chromatography. First eluting with ethyl acetate/hexanes (1:10) gave the t-butyl ester of 13 (100 mg).

¹H NMR (500 MHz, acetone-d₆): δ 7.60 (d, 1H), 7.50 (m, 2H), 6.97 (d, 1H), 6.35 (d, 1H), 4.08 (t, 2H), 3.68 (s, 3H), 3.53 (s, 2H), 1.40 (s, 9H), 1.35 (t, 3H).

Further elution with methanol/dichloromethane (1:9) afforded desried acid 13 (100 mg).

¹H NMR (500 MHz, acetone-d₆): δ 7.60 (d, 1H), 7.55 (d, 1H), 7.52 (dd, 1H), 6.98 (d, 1H), 6.38 (d, 1H), 4.10 (q, 2H), 3.70 (s, 3H), 3.63 (s, 2H), 1.35 (t, 3H). Treating the t-butyl ester with TFA/dichloromethane (1:1) at room temperature for 1 hour afforded the same acid.

¹H NMR (500 MHz, acetone-d₆): δ 7.93 (br d, 1H, NH), 7.35–7.25 (m, 2H), 7.15–7.05 (m, 4H, containing one NH), 6.89 (d, 1H), 4.90 (m, 1H), 4.30 (dd, 1H), 3.88 (s, 2H), 3.79 (s, 3H), 3.67–3.49 (m, 4H), 2.90 (dd, 1H), 2.80 (t, 2H), 2.79 (dd, 1H), 2.57 (t, 2H), 2.08 (m, 1H), 0.90–0.82 (2×d, 6H). MS (–APCI): m/z 623.7 (M–1).

Step 4: title compound

Coupling of acid 13 (86 mg) to resin I (100 mg) was carried out as described and the coupled resin was treated with TFA/H$_2$O to furnish the title compound (23 mg).

$^1$H NMR (500 MHz, acetone-d$_6$): δ 7.92 (br d, 1H, NH), 7.58 (d, 1H),, 7.56 (d, 1H), 7.52 (dd, 1H), 7.36–7.10 (m, 4H, containing one NH), 7.00 (d, 1H), 6.40 (d, 1H), 4.90 (m, 1H), 4.31 (dd, 1H), 4.13 (q, 2H), 3.88 (s, 2H), 3.72 (s, 3H), 3.69–3.52 (m, 4H), 2.90 (dd, 1H), 2.78 (dd, 1H), 2.09 (m, 1H), 1.40 (t, 3H), 0.90–0.82 (2×d, 6H). MS (–APCI): m/z 649.6 (M–1).

EXAMPLE 10

(3S)-5-[(2-Chloro-5-Fluorobenzyl)Sulfanyl]-3-{[(2S)-2-({2-[2-(Difluoromethoxy)-5-Methoxyphenyl]Acetyl}Amino)-3-Methylbutanoyl]Amino}4-Oxopentanoic Acid

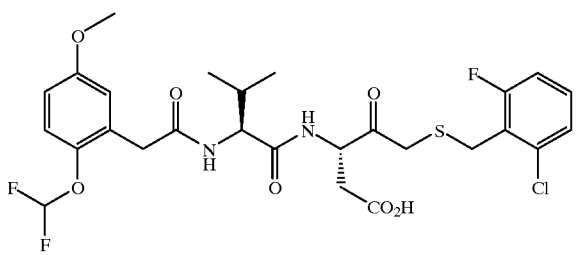

Step 1: Preparation of 5-difluoromethoxy-2-methoxyphenylacetic acid (14)

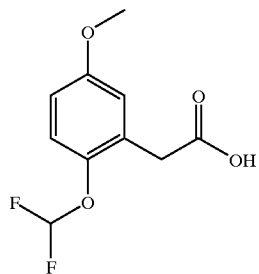

14

To a suspension of 5-methoxy-salicyladehyde (2.8 g), K$_2$CO$_3$ (3.1 g) in DMF (30 mL) at 90° C. under a nitrogen atmosphere was added methyl chlorodifluoroacetate (2.2 mL) dropwise in 10 minutes with vigorous stirring and the mixture was heated for four additional hours. The suspension was cooled to room temperature, diluted with water and ether. The organic phase was separated, washed with water and brine, dried over magnesium sulfate and filtered. Concentration in vacuo gave the crude product which was purified by silica gel chromatography. Eluting with ethyl acetate/hexanes (1:6) afforded 5-difluoromethoxy-2-methoxybenzaldehyde (0.99 g) as a colorless oil.

$^1$H NMR (400 MHz, acetone-d$_6$): δ 10.31 (s, 1H), 7.34 (d, 1H), 7.33 (d, 1H), 7.27 (dd, 1H), 7.04 (t, J=75 Hz, CHF2), 3.88 (s, 3H).

To a solution of the aldehyde (0.99 g) in ethanol at 0° C. was added NaBH$_4$ (1.85 g) and the mixture was stirred at 0° C. for 2 hours. 1 N HCl was then added carefully until pH~1 and the mixture extracted with ethyl acetate. The extract was processed as usual and the crude product was purified by silica gel chromatography. Eluting with ethyl acetate/hexanes (3:1) afforded 2-difluoromethoxy-5-methoxybenzyl alcohol (0.83 g) as a colorless oil.

$^1$H NMR (400 MHz, acetone-d$_6$): δ 7.13 (d, 1H), 7.10 (d, 1H), 6.83 (dd, 1H), 6.81 (t, 1H, J=75 Hz), 4.67 (d, 2H), 4.32 (t, 1H, OH) and 3.78 (s, 3H).

To a solution of the alcohol (354 mg) in dichloromethane at 0° C. as added dibromotriphenylphophorane (880 mg) and the solution was stirred at 0° C. for 1 hour. Workup as usual followed by purifying the crude with silica gel chromatography (ethyl acetate/hexanes 1:6) yielded 2-difluoromethoxy-5-methoxybenzyl bromide (460 mg) as a colorless oil.

$^1$H NMR (400 MHz, acetone-d$_6$): δ 7.18 (d, 1H), 7.12 (d, 1H), 6.96 (dd, 1H), 6.91 (t, J=75 Hz, 1H), 4.61 (s, 2H), 3.81 (s, 3H).

The carbonylation of this bromide was carried out similarly as described. The crude product was treated with 20% TFA in dichloromethane and then purified by silica gel chromatography to afford 5-difluoromethoxy-2-methoxyphenylacetic acid (14) (460 mg).

$^1$H NMR (400 MHz, acetone-d$_6$): δ 7.12 (d, 1H), 6.98 (d, 1H), 6.89 (dd, 1H), 6.72 (t, J=75 Hz, 1H), 3.79 (s, 3H), 3.69 (s, 2H).

Step 2: title compound

Acid 14 (204 mg) was coupled to Resin I as previously described and the coupled resin was treated with TFA/H$_2$O (9:1) to furnish the title compound.

$^1$H NMR (400 MHz, acetone-d$_6$): δ 7.96 (br d, 1H, NH), 7.41 (br d, 1H, NH), 7.36–7.27 (m, 2H), 7.15–7.08 (m, 2H), 6.97 (d, 1H), 6.83 (dd, 1H), 6.79 (t, J=75 Hz, 1H), 4.90 (m, 1H), 4.32 (dd, 1H), 3.88 (br s, 2H), 3.76 (s, 3H), 3.71–3.55 (m, 4H), 2.92 (dd, 1H), 2.79 (dd, 1H), 2.12 (m, 1H), 0.95–0.91 (2×d, 6H). MS (–APCI): m/z 617.3 (M–1).

EXAMPLE 11

(3S)-5-[(2-Chloro-6-Fluorobenzyl)]-3-{[(2S)-2-({2-[2-(Difluoromethoxy)-5-(Methylsulfonyl)Phenyl]Acetyl}Amino)-3-Methylbutanoyl}Amino-4-Oxopentanoic Acid

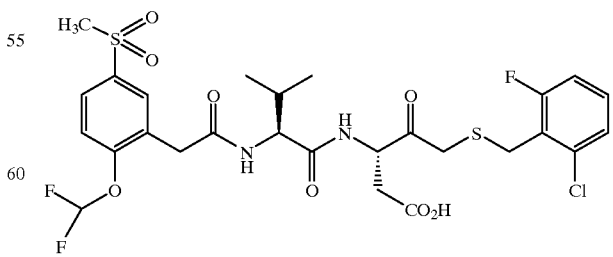

Step 1: preparation of 2-difluoromethoxy-5-methanesulfonyltoluene (15)

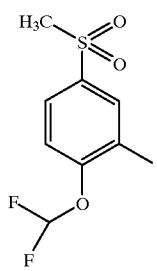

15

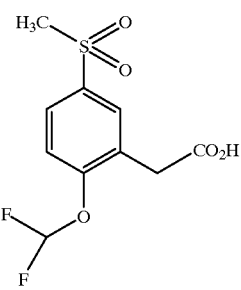

16

To a suspension of 4-methylthio-o-cresol (3.7 g) and K₂CO₃ (4.3 g) in DMF (50 mL) at 90° C. was added methyl chlorodifluoroacetate (4.2 g) dropwise and the mixture was heated with vigorous stirring for 4 hours. The solid was filtered off and the filtrate diluted with water and ether. The organic layer was separated, washed with water and brine, dried over magnesium sulfate and filtered. The filtrate was concentrated and the crude was purified by silica gel chromatography to afford 2-difluoromethxoy-5-methylthiotoluene (1.5 g).

¹H NMR (400 MHz, acetone-d₆): δ 7.20 (d, 1H), 7.15–7.10 (m, 2H), 6.89 (t, J=75 Hz, 1H), 2.48 (s, 3H), 2.24 (s, 3H).

The product was dissolved in methanol (100 mL) and to the solution was added Oxone™ (13.6 g) and the suspension was stirred overnight. The solid was filtered off and the filtrate was concentrated and redissolved in ethyl acetate. The solution was handled as usual and the crude product was purified by silica gel chromatography. Eluting with 40% ethyl acetate in hexanes yielded compound 15.

¹H NMR (400 MHz, acetone-d₆): δ 7.88 (d, 1H), 7.83 (dd, 1H), 7.40 (d, 1H), 7.18 (t, J=75Hz, 1H), 3.10 (s, 3H), 2.38 (s, 3H).

To a solution of sulfone 15 from above (0.92 g) dissolved in CCl₄ (20 mL) was added NBS (0.83 g) and a catalytic amount of benzoyl peroxide and the resulting mixture was irradiated with a sum lamp under reflux for 4 hours. After cooling to room temperature, the solid was filtered off and the filtrate was concentrated. The crude product was purified by silica gel chromatography. Eluting with ethyl acetate/hexanes (1:5) furnished 2-difluoromethoxy-5-methanesulfonylbenzyl bromide.

¹H NMR (400 MHz, acetone-d₆): δ 8.15 (d, 1H), 8.00 (dd, 1H), 7.50 (d, 1H), 7.29 (t, J=75Hz, 1H), 4.75 (s, 2H), 3.18 (s, 3H).

Step 2: preparation of 2-difluoromethoxy-5-methanesulfonylphenylacetic acid (16)

The carbonylation reaction of this benzyl bromide was performed as discussed. Thus, a mixture of the bromide (640 mg), [Rh(1,5-COD)Cl]₂ (150 mg), KI (20 mg) in t-butyl formate (4 mL) was heated to 60° C. under one atmosphere of CO (balloon) overnight. The mixture was cooled to room temperature, diluted with water and extracted with ethyl acetate (3×). The extracts were combined, washed with 5% Na₂S₂SO₃ (2×), water and brine, and dried. Concentration in vacuo gave the crude product which was purified by silica gel chromatography. Eluting first with ethyl acetate/hexanes (1:1.5) resulted in t-butyl 2-difluoromethoxy-5-methanesulfonylphenylacetate (212 mg). Further elution with methanol/dichloromethane (1:5) yielded acid 16 (260 mg).

¹H NMR (400 MHz, acetone-d₆): δ 8.00 (d, 1H), 7.95 (dd, 1H), 7.46 (d, 1H), 7.12 (t, J=75Hz, 1H), 3.85 (s, 2H), 3.14 (s, 3H). This acid was then processed as described to furnish the title compound.

¹H NMR (400 MHz, acetone-d₆/CD₃OD (2:1)): δ 7.93 (d, 1H), 7.90 (br d, 1H, NH), 7.85 (dd, 1H), 7.36 (d, 1H), 7.30–7.21 (m, 2H), 7.08 (t, 1H), 7.02 (t, J=75 Hz, 1H), 4.84 (dd, 1H), 4.22 (dd, 1H), 3.84 (br s, 2H), 3.82 (d, 1H), 3.73 (d, 1H), 3.61 (d, 1H), 3,50 (d, 1H), 3.09 (s, 3H), 2.85 (dd, 1H), 2.72 (dd, 1H), 2.07 (m, 1H), 0.93–0.91 (2×d, 6H). MS (–APCI): in/z 665.5 (M–1).

EXAMPLE 12

(3S )-5-[(2-Chloro-6-Fluorobenzyl)Sulfanyl]-3-{ [(2S)-2-({2-[5-(Benzenesulfonyl)-2-Ethoxyphenyl] Acetyl}amino)-3-Methylbutanoyl}Amino-4-Oxopentanoic Acid

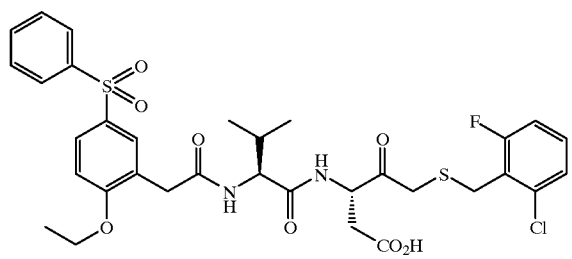

Step 1: 5-bezenethio-2-ethoxytoluene

The following experiment was carried out according to a modified literature procedure by Ortar, G. et al (Tetrahedron Lett., 36, 4133 (1995)). To a solution of 2-ethoxy-5-iodotoluene (970 mg) in N-methylmorpholine (10 mL) was added Pd₂dba₃ (271 mg) and dppf (657 mg) and the solution was stirred under nitrogen at room temperature for 5 minutes at which time thiophenol (0.76 mL) was introduced and the mixture was heated to 60° C. for 2 hours. The mixture was cooled to room temperature, diluted with brine and ethyl acetate. The organic layer was separated and washed with brine, dried, filtered and concentrated. The crude product was purified by silica gel chromatography (2% ethyl acetate in hexanes) to afford the desired product (860 mg) as a white solid.

$^1$H NMR (300 MHz, acetone-d$_6$): δ 7.30–7.22 (m, 4H), 7.17–7.10 (m, 3H), 6.94 (d, 1H), 4.08 (q, 2H), 2.18 (s, 3H), 1.39 (t, 3H).

Step 2: 5-benzenesulfonyl-2-ethoxytoluene

To a solution of the above sulfide (940 mg) in methanol was added Oxone™ (7.1 g) and the suspension was stirred at room temperature for 3 hours and then partitioned between water and ethyl acetate. The organic layer was processed as usual and the crude compound was purified by silica gel chromatography (ethyl acetate/hexanes 1:4). The desired product was obtained as a white solid (860 mg).

$^1$H NMR (400 MHz, acetone-d$_6$): 67 7.95 (dd, 2H), 7.79 (dd, 1H), 7.73 (d, 1H), 7.65–7.55 (m, 3H), 7.05 (d, 1H), 4.12 (q, 2H), 2.22 (s, 3H), 1.39 (t, 3H).

Step 3: 5-benzenesulfonyl-2-ethoxybenzyl bromide

A mixture of the sulfone (450 mg), NBS (290 mg) and a catalytic amount of bezoyl peroxide in CCl$_4$ was irradiated with a sum lamp under reflux for 4 hours. The mixture was cooled to room temperature and filtered, and the filtrate was concentrated. The residue was subjected to silica gel chromatography. Eluting with ethyl acetate/hexanes (1:4) afforded the desired product (480 mg) as a colorless oil.

$^1$H NMR (400 MHz, acetone-d$_6$): δ 8.05 (d, 1H), 8.00–7.91 (m, 3H), 7.63–7.53 (m, 3H), 7.16 (d, 1H), 4.64 (s, 2H), 4.19 (q, 2H), 1.40 (t, 3H).

Step 4: 5-benzenesulfonyl-2-ethoxyphenylacetic acid (17)

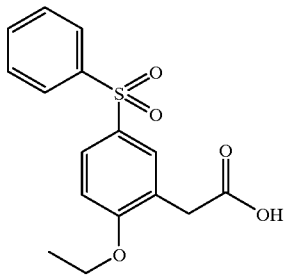

17

The carbonylation of 5-benzenesulfonyl-2-ethoxybenzyl bromide was done as described to yield acid 17 (150 mg) as a white solid.

$^1$H NMR (400 MHz, aceotn-d$_6$): δ 7.95 (dd, 2H0, 7.88 (m, 2H), 7.66–7.55 (m, 3H), 7.13 (d, 1H), 4.14 (q, 2H), 3.69 (s, 2H), 1.37 (t, 3H).

Step 5: title compound

Acid 17 was processed as usual to give the title compound.

$^1$H NMR (400 MHz, acetone-d$_6$): δ 7.97–7.92 (m, 3H, containing one NH), 7.86–7.82 (m, 2H), 7.63–7.54 (m, 3H), 7.37–7.27 (m, 3H, containing one NH), 7.15–7.10 (m, 2H), 4.91 (m, 1H), 4.34 (dd, 1H), 4.15 (q, 2H), 3.89 (s, 2H), 3.72–3.59 (m, 4H), 2.92 (dd, 1H), 2.80 (dd, 1H), 2.08 (m, 1H), 1.38 (t, 3H), 0.90–0.82 (2×d, 6H). MS (-APCI): m/z 705.6 (M−1).

EXAMPLE 13

(3S)-5-(Benzylsulfanyl)-3-{[(2S)-2-({2-Methoxy-5-(3-Methyl-1,2,4-Oxadiazol-5-Yl)-Phenyl]Acetyl}Amino)-3-Methylbutanoyl]Amino}-4-Oxopentanoic Acid

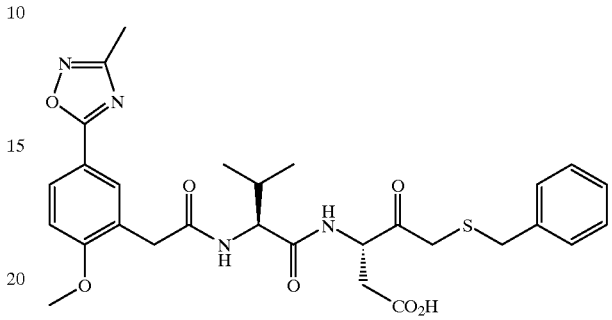

Step 1: methyl 5-iodo-2-methoxyphenylacetate (18)

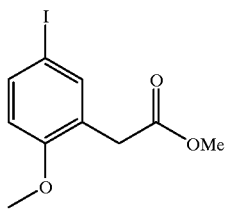

18

To a solution of 2-methoxyphenylacetic acid (14 g, 84 mmol) in dioxane (100 mL) at 0° C. was added ICl (14 g, 86 mmol) in dioxane (50 mL) over a period of 15 min. The mixture was stirred at 0° C. for an additional 15 min and poured to a mixture of water (2 L) and 5% Na$_2$S$_2$O$_3$ (50 mL). After the solution became clear, the solid was collected by vacuum filtration and washed with water. Drying under vacuum afforded 10 g of 5-iodo-2-methoxyphenylaceitc acid.

$^1$H NMR (400 MHz, acetone-d$_6$): δ 7.55 (d, 1H), 7.54 (s, 1H), 6.80 (d, 1H), 3.80 (s, 3H), 3.58 (s, 2H).

The acid obtained above was added to a solution of acetyl chloride (50 mL) in methanol (500 mL) and the mixture was stirred overnight and then heated to reflux for 2 h. After cooling to room temperature, the mixture was concentrated and the crude product was purified by flash column chromatography. Eluting with EtOAc/Hexanes (1/9) furnished desired product 18 (9 g).

$^1$H NMR (400 MHz, acetone-d$_6$): δ 7.58 (d, 1H), 7.55 (s, 1H), 6.82 (d, 1H), 3.80 (s, 3H), 3.60 (s, 3H), 3.58 (s, 2H).

Step 2: compound 19

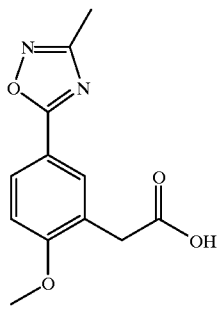

19

The following reaction was carried out according to the literature procedure (see: Young, J. R. and DeVita R. J., Tetrahedron Lett. 39, 3931 (1998)).

The dried resin was treated with TFA/$H_2O$ (9/1, 2 mL) for 30 min and filtered. The filtrate was collected and concentrated. The residue was triturated with ether to yield the title compound as a white solid.

$^1$H NMR (400 MHz, DMSO-$d_6$): δ 8.64 (d, 1H), 8.03 (d, 1H), 7.95 (d, 1H), 7.91 (s, 1H), 7.35–7.18 (m, 5H), 7.21 (d, 1H), 4.75–4.65 (m, 1H), 4.18–4.10 (m, 1H), 3.81 (s, 3H), 3.75–3.25 (m, 6H), 2.78 (m, 1H), 2.76 (dd, 1H), 2.55–2.45 (m, 2H), 2.36 (s, 3H), 2.02–1.90 (m, 1H), 0.84 (d, 6H).

Assays for Determining Biological Activity (a) Measurement of caspase activity by cleavage of a fluorogenic substrate (b) A fluorogenic derivative of the tetrapeptide recognized by caspase-3 and corresponding to the $P_1$ to $P_4$ amino acids of the PARP cleavage site, Ac-DEVD-AMC (AMC, amino-4-methylcoumarin) was prepared as follows: i) synthesis of N-Ac-Asp(OBn)-Glu(OBn)-Val-$CO_2$H, ii) coupling with Asp(OBn)-7-amino-4-methylcoumarin, iii) removal of benzyl groups.

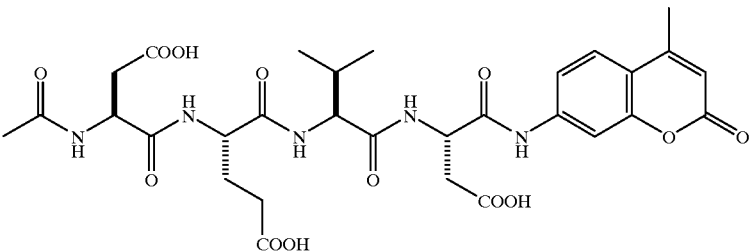

A mixture containing iodide 18 (700 mg, 2.3 mmol), $(PPh_3)_2PdCl_2$ (322 mg, 0.46 mmol), methylamidoxime (518 mg, 6.9 mmol) and triethylamine (644 ml,, 4.6 mmol) in toluene (10 mL) was carefully purged with CO and then heated to 90° C. for 10 h and cooled to room temperature. Concentration of the volatiles gave the crude product which was purified by column chromatography. Eluting with EtOAc/hexanes (1:4) give the desired product as a white solid.

$^1$H NMR (400 MHz, acetone-$d_6$): δ 8.05 (d, 1H), 8.01 (s, 1H), 7.20 (d, 1H), 3.92 (s, 3H), 3.75 (s, 2H), 3.65 (s, 3H), 2.37 (s, 3H).

The ester (900 mg) was dissolved in THF (10 mL), methanol (10 mL) and water (10 mL) and to the solution was added LiOH (5 mL, 1M in water). After stirring at room temperature for 4 h, the mixture was acidified with 1N HCl and extracted with ethyl acetate (3×). The extracts were combined, washed with water and brine, dried over $MgSO_4$ and concentrated to afford the desired acid as a white powder.

1H NMR (300 MHz, acetone-$d_6$): δ 8.05 (d, 1H), 8.01 (s, 1H), 7.18 (d, 1H), 3.94 (s, 3H), 3.71 (s, 2H), 2.37 (s, 3H).

Step 3: title compound

To a suspension of Resin G (100 mg, 0.7 mmol/ g, 0.07 mmol) in DMF (2 mL) was added acid 19 (100 mg, 0.4 mmol), HOBt (68 mg, 0.5 mmol) and 1-(3-dimethylaminopropyl)-3-ethylcarbodiimide methiodide (150 mg, 0.5 mmol) and the mixture was agitated for 3 h and filtered (the couping can be also carried out using HATU and DIEA in DMF). The residual resin was washed with DMF, THF, $CH_2Cl_2$, AcOH, $CH_2Cl_2$ and then dried under vacuum.

Standard reaction mixtures (300 μL final volume), contained Ac-DEVD-AMC and purified or crude caspase-3 enzyme in 50 mM Hepes/KOH (pH 7.0), 10% (v/v) glycerol, 0.1% (w/v) CHAPS, 2 mM EDTA, 5 mM dithiothreitol, and were incubated at 25° C. Reactions were monitored continuously in a spectrofluorometer at an excitation wavelength of 380 nm and an emission wavelength of 460 nm.

(c) Cell Death Detection ELISA (Whole Cell Assay)

Photometric immunoassay for the qualitative and quantitative in vitro determination of cytoplasmic histone-associated-DNA-fragments (mono- and oligonucleosomes) after induced cell death. This assay was performed using the commercially available kit from Boehringer Mannheim, cat. No. 1 920 685.

(d) In Vivo Myocardial Ischemia and Reperfusion Injury in Rats

Male Sprague-Dawley rats (300–400 g) were fasted overnight, and then anesthetized with intraperitoneal administration of sodium pentobarbital (65 mg/kg). To monitor heart rate and aortic pressure the left carotid artery was isolated and a cannula placed in the vessel. The aortic cannula was interfaced with a pressure transducer which was connected to a physiologic recorder. The left jugular vein was isolated and cannulated for administration of a caspase inhibitor compound or vehicle (2% dimethylsulfoxide in 0.9% NaCl). A left thoracotomy was performed in the region overlying the heart and the pericardium opened, exposing the heart. The origin of the left coronary artery was visualized and a 4.0 suture passed under the artery approximately 2–3 mm from its origin. The ends of the suture were passed through a short length of 2 mm id tubing and coronary artery occlusion effected by placing tension on the suture such that the tube compressed the artery. After initial placement of the suture/occluder, the thoracotomy was closed with a small clamp and opened only to effect occlusion and reperfusion of the artery. A Lead II electrocardiograph (ECG) signal was obtained by placing subdermal platinum leads and continuously monitored. After a baseline period of 20–30 minutes the left coronary artery was occluded for 45 minutes. The period of reperfusion was 3 hours. The caspase inhibitor or vehicle was administered as a first bolus 5 minutes before the onset of ischemia and a second bolus was administered again at the onset of reperfusion. Additionally, an infusion was initiated immediately after the first bolus dose. Control animals received the vehicle alone in equal volumes to the caspase inhibitor treated animals. At the end of reperfusion the animals were euthanized and infarct size determined using a dual staining technique (1.5% w/v triphenyltetrazolium chloride to demarcate infarct tissue and 0.25% w/v Evan's blue to demarcate the area at risk of infarct. The heart was subsequently cut transversely into 4 slices of equal thickness, and infarct size and area at risk quantified using planimetry.

Using the above procedure, it is demonstrated that administration of a caspase inhibitor reduces infarct size in the rat subjected to 45 minutes of regional ischemia and 3 hours of reperfusion.

What is claimed is:

1. A compound represented by formula I:

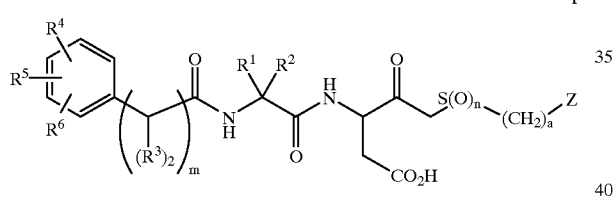

or a pharmaceutically acceptable salt, ester or hydrate thereof, wherein:

a is 0 or 1:

m is 1:

n is 0, 1 or 2;

Z is selected from the group consisting of:
1) $C_{1-18}$alkyl,
2) $C_{3-11}$cycloalkyl, said alkyl and cycloalkyl groups being optionally substituted with 1–4 halo groups,
3) phenyl or naphthyl, optionally substituted by one or two groups selected from the group consisting of: halo, nitro, $C_{1-4}$alkyl and $C_{1-4}$alkoxy, said alkyl and alkoxy groups being optionally substituted with 1–3 halo groups, and
4) $HET^1$ wherein $HET^1$ represents a 5 or 6 membered aromatic or non-aromatic ring, and the benzofused analogs thereof, containing from 1–3 heteroatoms selected from O, S and N, and optionally substituted with 1–2 groups selected from halo, $C_{1-4}$alkyl and $C_{1-4}$acyl:

$R^1$ represents a member selected from the group consisting of: H, aryl, $C_{1-6}$alkyl optionally substituted by $OR^7$, and $C_{5-7}$cycloalkyl optionally containing one heteroatom selected from O, S and $NR^8$, and $R^2$ represents H, or in the alternative, $R^1$ and $R^2$ are taken in combination and represent a ring of 4–7 members, said ring optionally containing one heteroatom selected from O, S and $NR^8$;

$R^7$ is selected from the group consisting of: H, $C_{1-5}$alkyl and benzyl optionally substituted with 1–2 groups selected from halo, $C_{1-4}$alkyl and $C_{1-4}$alkoxy; and $R^8$ is H or $C_{1-4}$alkyl;

each $R^3$ is independently selected from the group consisting of: H, $C_{1-6}$alkyl optionally containing 1–2 oxo groups, $C_{1-4}$alkoxy and halo;

$R^4$, $R^5$ and $R^6$ are independently selected from the group consisting of:
1) H,
2) halo,
3) $C_{1-4}$alkoxy optionally substituted with 1–3 halo atoms,
4) $NO_2S$
5) OH,
6) benzyloxy, the benzyl portion of which is optionally substituted with 1–2 members selected from the group consisting of: halo, CN, $C_{1-4}$alkyl and $C_{1-4}$alkoxy, said alkyl and alkoxy being optionally substituted with 1–3 halo groups,
7) NH—$C_{1-4}$acyl,
8) $C_{1-4}$acyl,
9) O—$C_{1-4}$alkyl-$CO_2$H, optionally esterified with a $C_{1-6}$ alkyl or $C_{5-7}$ cycloalkyl group,
10) CH=CH—$CO_2$H,
11) $C_{0-5}$alkyl$CO_2$H,
12) $C_{0-5}$alkylC(O)$NH_2$, optionally substituted on the nitrogen atom by 1–2 $C_{1-4}$alkyl groups;
13) $C_{0-2}$ alkylS(O)$_{0-2}$$C_{1-4}$alkyl
14) S(O)$_{0-2}$-$C_{1-6}$ alkyl or S(O)$_{0-2}$-phenyl, said alkyl and phenyl portions thereof being optionally substituted with 1–3 members selected from the group consisting of: halo, CN, $C_{1-4}$alkyl and $C_{1-4}$alkoxy, said alkyl and alkoxy being optionally substituted by 1–3 halo groups,
15) benzoyl optionally substituted by 1–2 members selected from the group consisting of: halo, CN, $C_{1-4}$alkyl and $C_{1-4}$alkoxy, said alkyl and alkoxy groups being optionally substituted by 1–3 halo groups,
16) phenyl or naphthyl, optionally substituted with 1–2 members selected from the group consisting of: halo, CN, $C_{1-4}$alkyl and C 1–4alkoxy, said alkyl and alkoxy being optionally substituted with 1–3 halo groups,
17) CN,
18) —$C_{1-4}$alkyl-$HET^2$, wherein $HET^2$ represents a 5–7 membered aromatic or non-aromatic ring containing 1–4 heteroatoms selected from O, S and $NR^8$ and optionally containing 1–2 oxo groups, and optionally substituted with 1–3 $C_{1-4}$ alkyl, OH, halo or $C_{1-4}$acyl groups;
19) —$OC_{0-4}$alkyl-$HET^3$, wherein $HET^3$ is a 5 or 6 membered aromatic or non-aromatic ring containing from 1 to 3 heteroatoms selected from O, S and N, and optionally substituted with one or two groups selected from halo and $C_{1-4}$alkyl, and optionally containing 1–2 oxo groups, and
20) $HET^4$, wherein $HET^4$ is a 5 or 6 membered aromatic or non-aromatic ring, and the benzofused analogs thereof, containing from 1 to 4 heteroatoms selected from O, S and N, and is optionally substituted by one or two groups selected from halo, $C_{1-4}$alkyl and $C_{1-4}$acyl, or $R^4$ and $R^5$ are taken in combination and represent a fused heteroaryl ring as shown below:

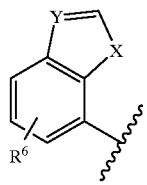

wherein Y is selected from the group consisting of CH and N, and X is selected from O, S and NH, and $R^6$ is as defined above.

2. A compound represented by formula I:

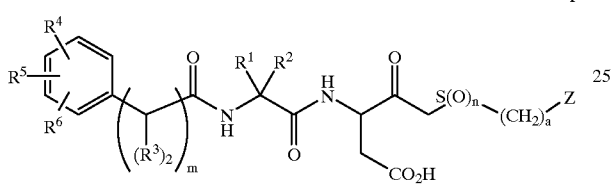

or a pharmaceutically acceptable salt, ester or hydrate thereof, wherein:

a is 0 or 1:

m and n are 0, 1 or 2;

Z is phenyl optionally substituted by one or two groups selected from halo, nitro, $C_{1-4}$alkoxy optionally substituted by up to 3 halogen atoms, or $C_{1-4}$alkyl optionally substituted by up to 3 halogen atoms;

$R^1$ represents a member selected from the group consisting of: H, aryl, $C_{1-6}$alkyl optionally substituted by $OR^7$, and $C_{5-7}$cycloalkyl optionally containing one heteroatom selected from O, S and $NR^8$, and $R^2$ represents H, or in the alternative, $R^1$ and $R^2$ are taken in combination and represent a ring: of 4–7 members, said ring optionally containing one heteroatom selected from O, S and $NR^8$;

$R^7$ is selected from the group consisting of: H, $C_{1-5}$alkyl and benzyl optionally substituted with 1–2 groups selected from halo, $C_{1-4}$alkyl and $C_{1-4}$alkoxy; and $R^8$ is H or $C_{1-4}$alkyl;

each $R^3$ is independently selected from the group consisting of: H, $C_{1-6}$alkyl optionally containing 1–2 oxo groups, $C_{1-4}$alkoxy and halo;

$R^4$, $R^5$ and $R^6$ are independently selected from the group consisting of:
1) H,
2) halo,
3) $C_{1-4}$alkoxy optionally substituted with 1–3 halo atoms,
4) $NO_2$,
5) OH,
6) benzyloxy, the benzyl portion of which is optionally substituted with 1–2 members selected from the group consisting of: halo, CN, $C_{1-4}$alkyl and $C_{1-4}$alkoxy, said alkyl and alkoxy being optionally substituted with 1–3 halo groups,
7) NH—$C_{1-4}$acyl,
8) $C_{1-4}$acyl,
9) O—$C_{1-4}$alkyl-$CO_2$H, optionally esterified with a $C_{1-6}$ alkyl or $C_{5-7}$cycloalkyl group,
10) CH=CH—$CO_2$H,
11) $C_{0-5}$alkyl$CO_2$H,
12) $C_{0-5}$alkylC(O)$NH_2$, optionally substituted on the nitrogen atom by 1–2 Cl 4alkyl groups;
13) $C_{0-2}$alkylS(O)$_{0-2}C_{1-4}$alkyl;
14) $S(O)_{0-2}-C_{1-6}$ alkyl or $S(O)_{0-2}$-phenyl, said alkyl and phenyl portions thereof being optionally substituted with 1–3 members selected from the group consisting of: halo, CN, $C_{1-4}$alkyl and $C_{1-4}$alkoxy, said alkyl and alkoxy being optionally substituted by 1–3 halo groups,
15) benzoyl optionally substituted by 1–2 members selected from the group consisting of: halo, CN, $C_{1-4}$alkyl and $C_{1-4}$alkoxy, said alkyl and alkoxy groups being optionally substituted by 1–3 halo groups,
16) phenyl or naphthyl, optionally substituted with 1–2 members selected from the group consisting of: halo, CN, $C_{1-4}$alkyl and C 1–4alkoxy, said alkyl and alkoxy being optionally substituted with 1–3 halo groups,
17) CN,
18) —$C_{1-4}$alkyl-$HET^2$, wherein $HET^2$ represents a 5–7 membered aromatic or non-aromatic rind containing 1–4 heteroatoms selected from O, S and $NR^8$ and optionally containing 1–2 oxo groups, and optionally substituted with 1–3 $C_{1-4}$ alkyl, OH, halo or $C_{1-4}$acyl groups;
19) —$OC_{0-4}$alkyl-$HET^3$, wherein $HET^3$ is a 5 or 6 membered aromatic or non-aromatic ring containing from 1 to 3 heteroatoms selected from O, S and N, and optionally substituted with one or two groups selected from halo and $C_{1-4}$alkyl, and optionally containing 1–2 oxo groups, and
20) $HET^4$, wherein $HET^4$ is a 5 or 6 membered aromatic or non-aromatic ring, and the benzofused analogs thereof, containing from 1 to 4 heteroatoms selected from O, S and N, and is optionally substituted by one or two groups selected from halo, $C_{1-4}$alkyl and $C_{1-4}$acyl, or $R^4$ and $R^5$ are taken in combination and represent a fused heteroaryl ring as shown below:

wherein Y is selected from the group consisting of CH and N, and X is selected from O, S and NH, and $R^6$ is as defined above.

3. A compound represented by formula I:

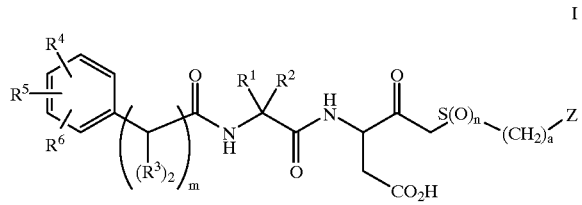

or a pharmaceutically acceptable salt, ester or hydrate thereof, wherein:

a is 1;

m is 1;

n is 0;

Z is selected from the group consisting of:
1) phenyl, optionally substituted by one or two groups selected from halo, nitro, $C_{1-4}$alkoxy optionally substituted by up to 3 halogen atoms, and $C_{1-4}$ alkyl optionally substituted by up to 3 halogen atoms, and
2) $HET^1$, wherein $HET^1$ represents pyridine, pyrimidine, pyridazine, furan, thiophene, thiazole or oxazole, optionally substituted with 1–2 groups selected from halo, $C_{1-4}$alkyl and $C_{1-4}$acyl;

$R^1$ represents a member selected from the group consisting of: H, $C_{1-4}$alkyl optionally substituted by $OR^7$, and $C_{5-7}$cycloalkyl optionally containing one heteroatom selected from O, S and $NR^8$;

$R^2$ is hyrdogen;

$R^3$ is hydrogen;

$R^7$ is selected from the group consisting of: H, $C_{1-5}$alkyl and benzyl optionally substituted with 1–2 groups selected from halo, $C_{1-4}$alkyl and $C_{1-4}$alkoxy;

$R^8$ is H or $C_{1-4}$alkyl;

$R^4$, $R^5$ and $R^6$ are independently selected from the group consisting of:
1) H,
2) halo,
3) $C_{1-4}$alkoxy optionally substituted with 1–3 halo atoms,
4) $NO_2$,
5) OH,
6) benzyloxy, the benzyl portion of which is optionally substituted with 1–2 members selected from the group consisting of: halo, CN, $C_{1-4}$alkyl and $C_{1-4}$alkoxy, said alkyl and alkoxy being optionally substituted with 1–3 halo groups,
7) NH—$C_{1-4}$acyl,
8) $C_{1-4}$acyl,
9) O—$C_{1-4}$alkyl-$CO_2$H, optionally esterified with a $C_{1-6}$ alkyl or $C_{5-7}$cycloalkyl group,
10) CH=CH—$CO_2$H,
11) $C_{0-5}$alkyl$CO_2$H,
12) $C_{0-5}$alkylC(O)$NH_2$, optionally substituted on the nitrogen atom by 1–2 $C_{1-4}$alkyl groups;
13) $C_{0-2}$ alkylS(O)$_{0-2}$$C_{1-4}$alkyl;
14) S(O)$_{0-2}$-$C_{1-6}$ alkyl or S(O)$_{02}$-phenyl, said alkyl and phenyl portions thereof being optionally substituted with 1–3 members selected from the group consisting of: halo, CN, $C_{1-4}$alkyl and $C_{1-4}$alkoxy, said alkyl and alkoxy being optionally substituted by 1–3 halo groups,
15) benzoyl optionally substituted by 1–2 members selected from the group consisting of: halo, CN, $C_{1-4}$alkyl and $C_{1-4}$alkoxy, said alkyl and alkoxy groups being optionally substituted by 1–3 halo groups,
16) phenyl or naphthyl, optionally substituted with 1–2 members selected from the group consisting of: halo, CN, $C_{1-4}$alkyl and Cl-4alkoxy, said alkyl and alkoxy being optionally substituted with 1–3 halo groups,
17) CN,
18) —$C_{1-4}$alkyl-$HET^2$, wherein $HET^2$ is selected from the group consisting of: butyrolactone, tetrahydrofuran, tetrahydropyran and 2-pyrrolidinone;
19) —$OCO_{0-4}$alkyl-$HET^3$, wherein $HET^3$ is selected from the group consisting of: butyrolactone, tetrahydrofuran, tetrahydropyran, 2-pyrrolidinone, pyridine and pyrimidine, and
20) $HET^4$, wherein $HET^4$ is selected from the group consisting of: 1,2,3-oxadiazole, 1,2,4-oxadiazole, 1,3,4-oxadiazole, 1,2,3-thiadiazole, 1,2,4-thiadiazole, 1,3,4-thiadiazole, thiophene, pyrrole, pyridine, tetrazole, oxazole, thiazole, 1,2,3-triazole, 1,2,4-triazole and 1,3,4-triazole, or $R^4$ and R5 are taken in combination and represent a fused heteroaryl ring as shown below:

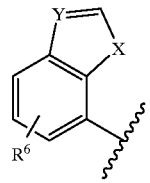

wherein Y is selected from the group consisting of CH and N, and X is selected from O, S and NH, and $R^6$ is as defined above.

4. A compound in accordance with table I below:

TABLE I

1 Chiral

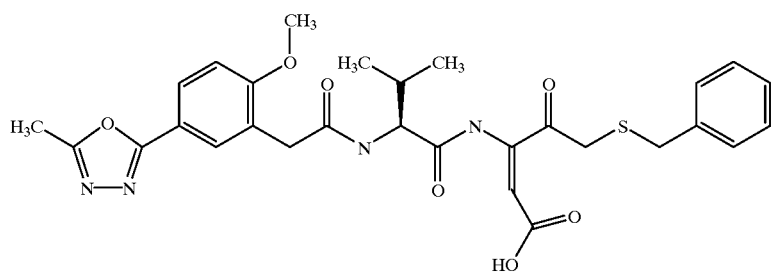

TABLE I-continued
2 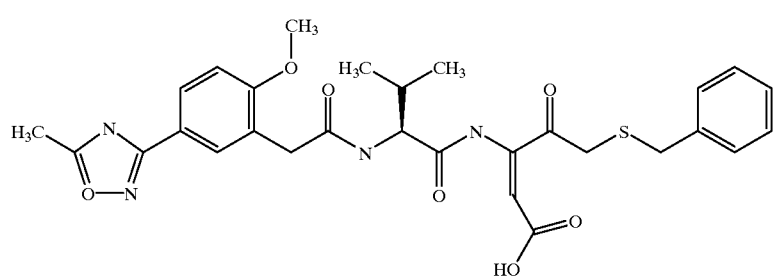
3 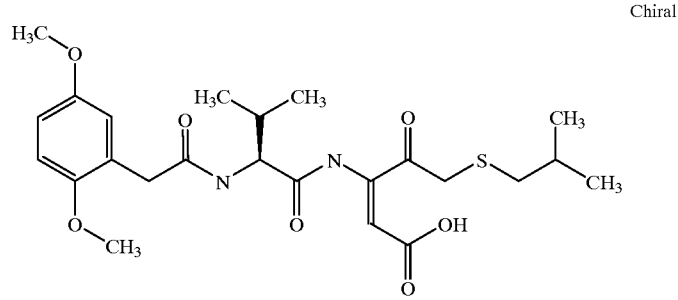
Chiral
4 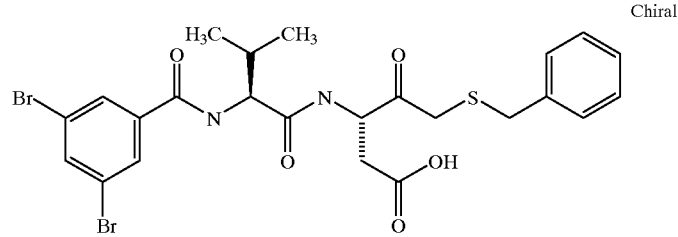
Chiral
5 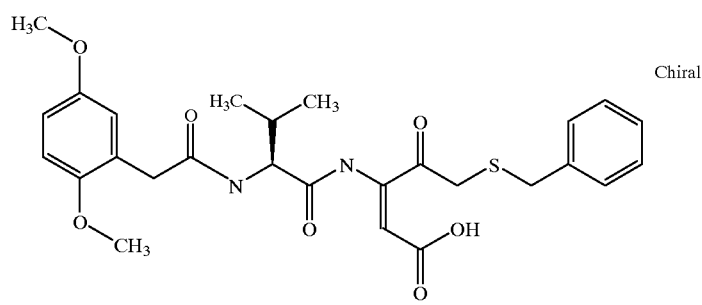
Chiral
6 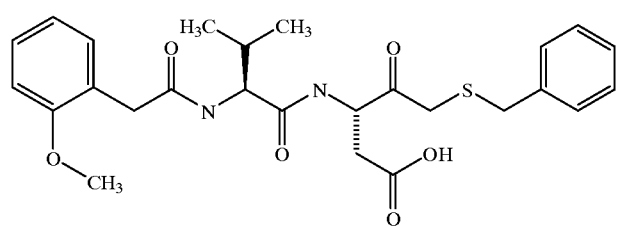
Chiral TABLE I-continued
7 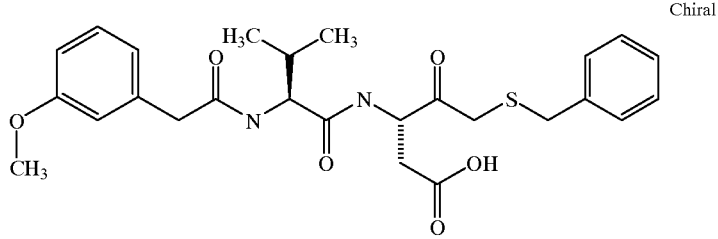 Chiral
8 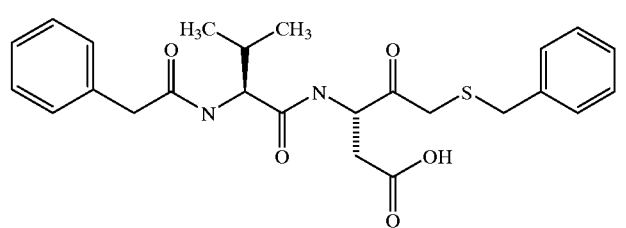 Chiral
9 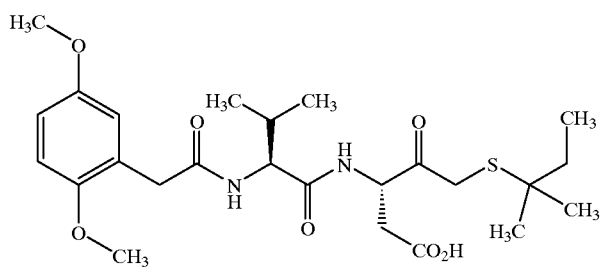 Chiral
10 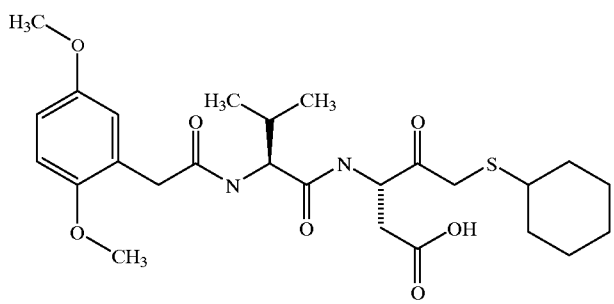 Chiral
11 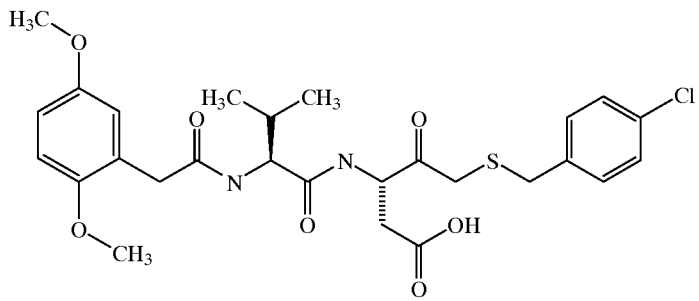 Chiral TABLE I-continued
12 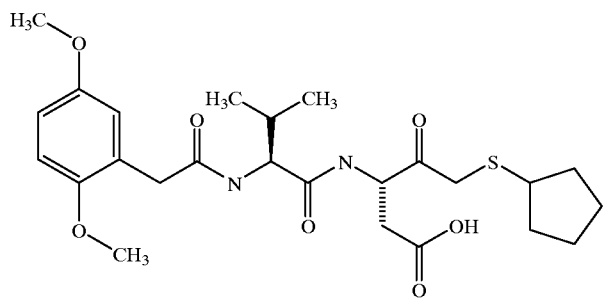 Chiral
13 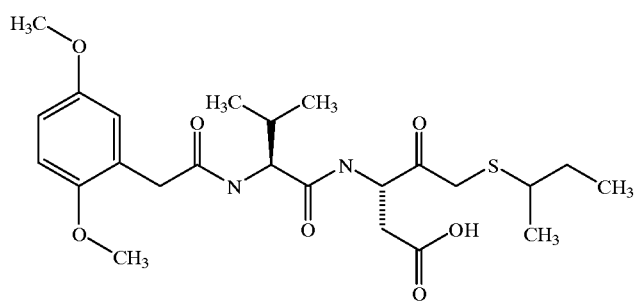 Chiral
14 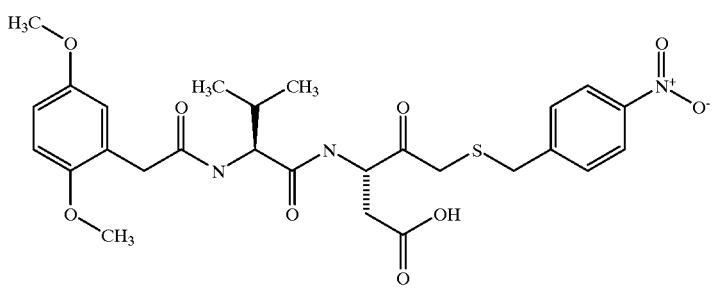 Chiral
15 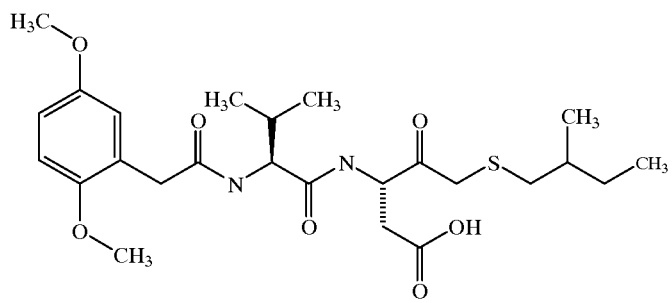 Chiral TABLE I-continued
| | | |
|---|---|---|
| 16 | 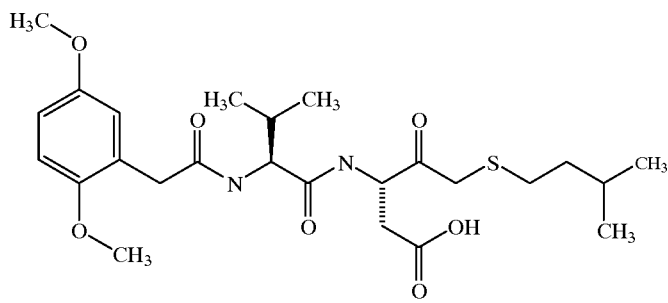 | Chiral |
| 17 | 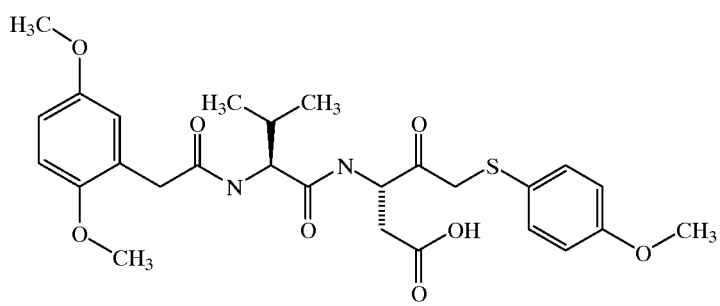 | Chiral |
| 18 | 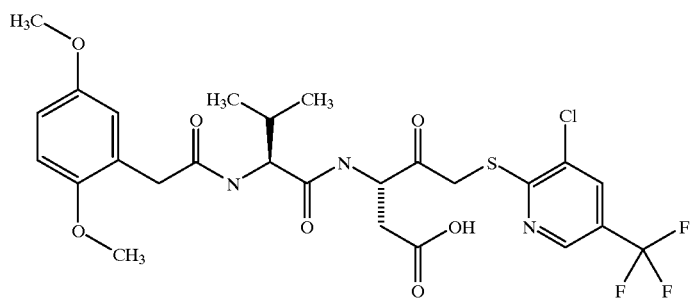 | Chiral |
| 19 | 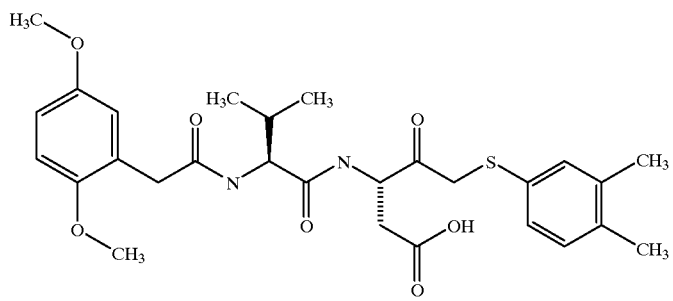 | Chiral |

TABLE I-continued

| # | Structure | |
|---|---|---|
| 20 | (2,5-dimethoxyphenylacetyl)-Val-Asp(CH2-S-butyl) ketone | Chiral |
| 21 | (2,5-dimethoxyphenylacetyl)-Val-Asp(CH2-S-(4-isopropylphenyl)) ketone | Chiral |
| 22 | (2,5-dimethoxyphenylacetyl)-Val-Asp(CH2-S-(3-methoxyphenyl)) ketone | Chiral |
| 23 | (2,5-dimethoxyphenylacetyl)-Val-Asp(CH2-S-CH2-(2-furyl)) ketone | Chiral |
| 24 | (2,5-dimethoxyphenylacetyl)-Val-Asp(CH2-S-CH2CF3) ketone | Chiral |

TABLE I-continued
25 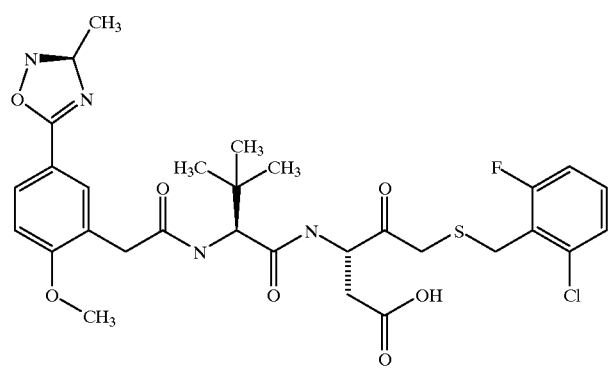 Chiral
26 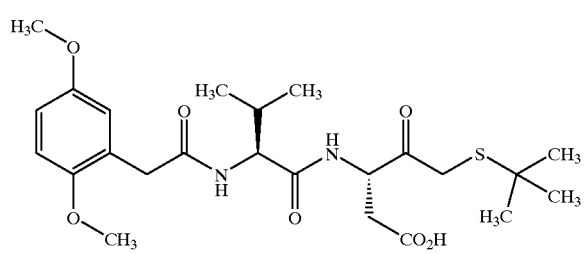 Chiral
27 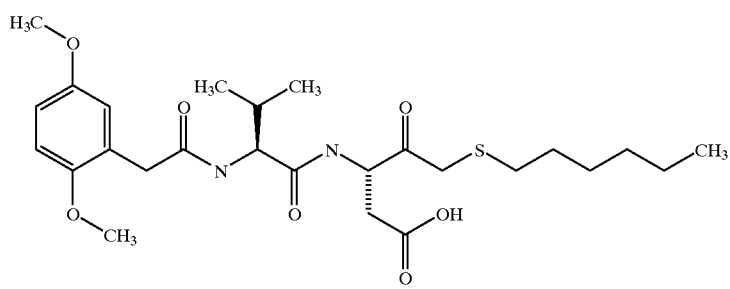 Chiral
28 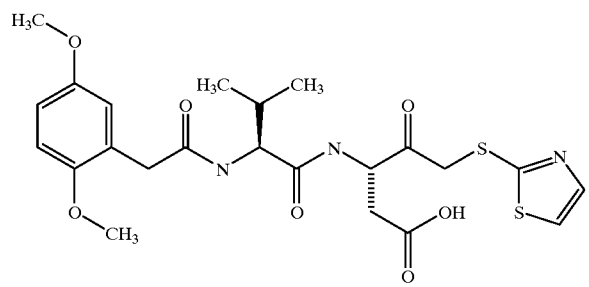 Chiral TABLE I-continued
29 Chiral
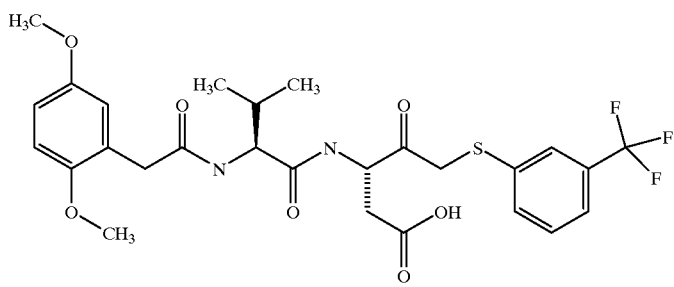
30 Chiral
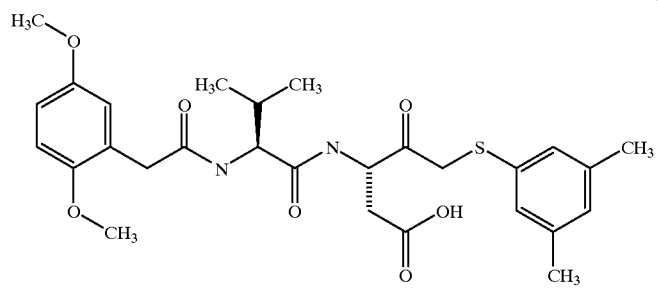
31 Chiral
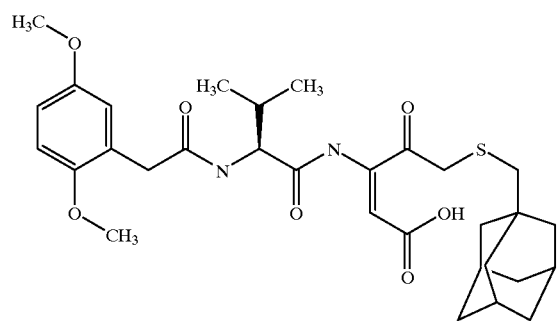
32 Chiral
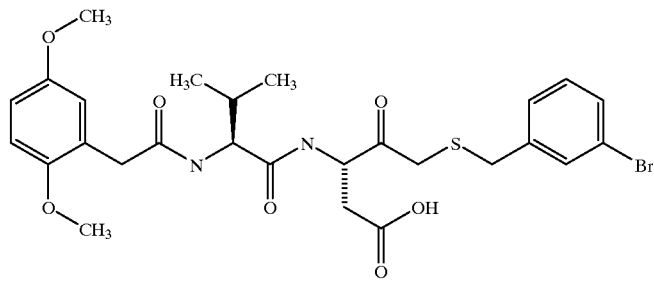

TABLE I-continued
33 Chiral
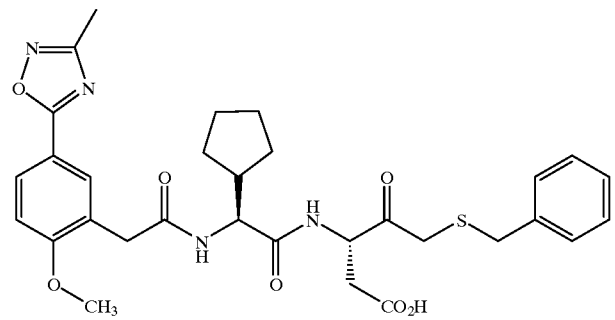
34 Chiral
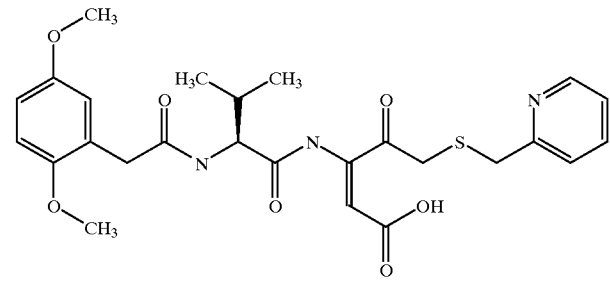
35 Chiral
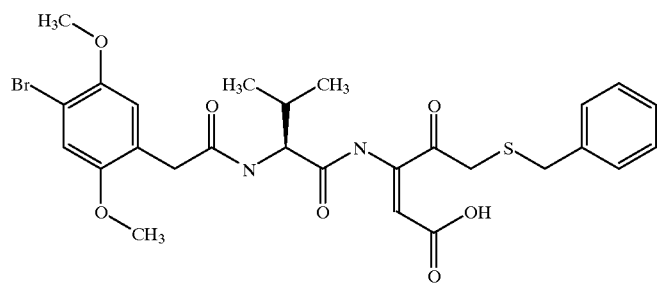
36 Chiral
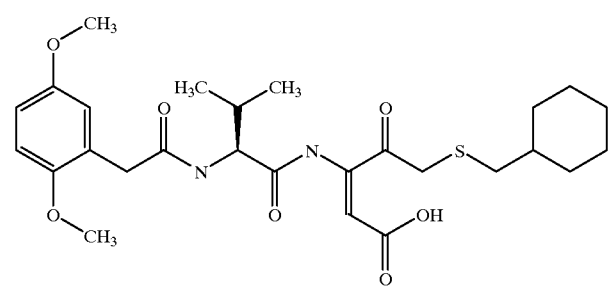
37 Chiral
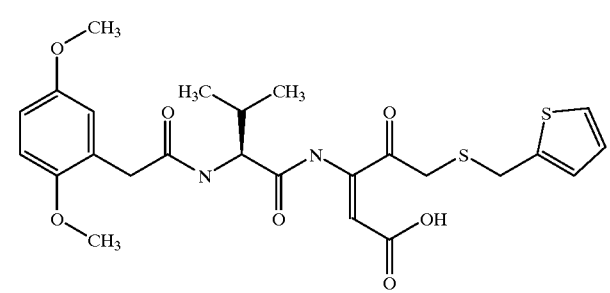

TABLE I-continued
38 Chiral
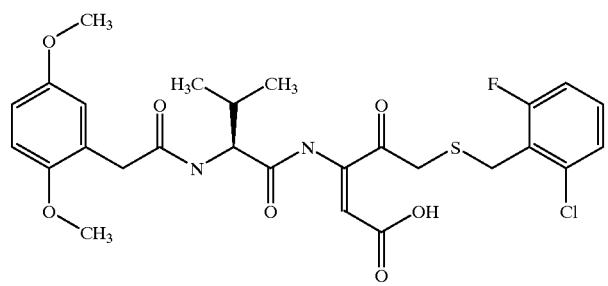
39 Chiral
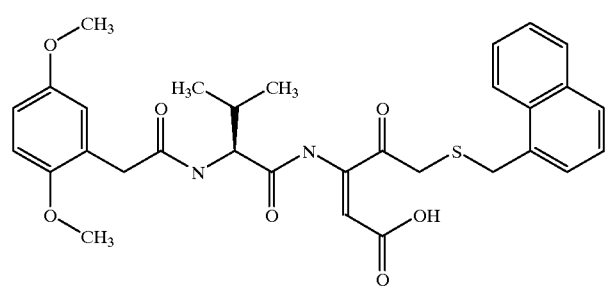
40 Chiral
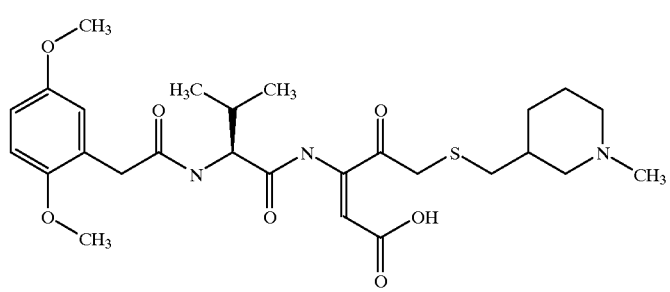
41 Chiral
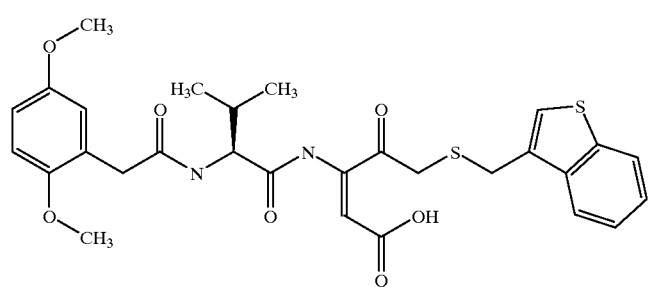
42 Chiral
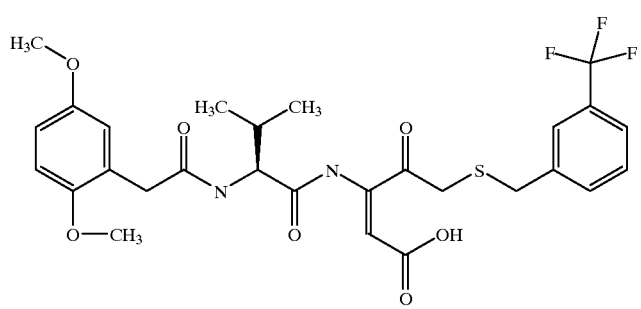

TABLE I-continued
| | | |
|---|---|---|
| 43 | 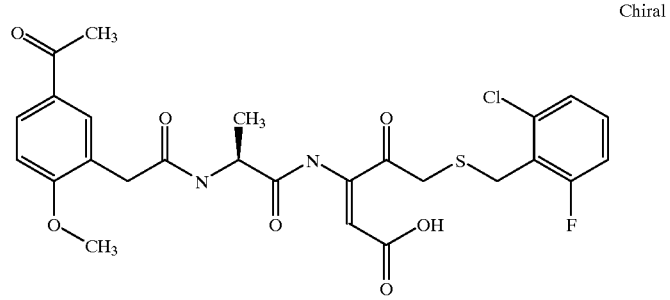 | Chiral |
| 44 | 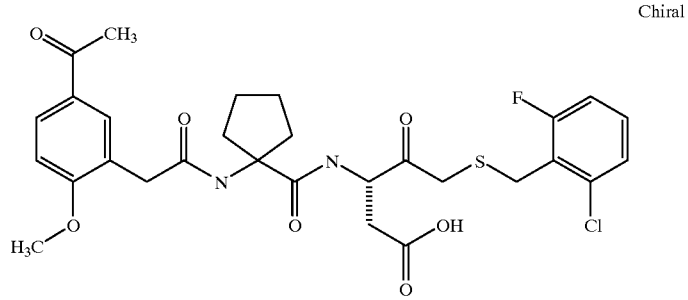 | Chiral |
| 45 | 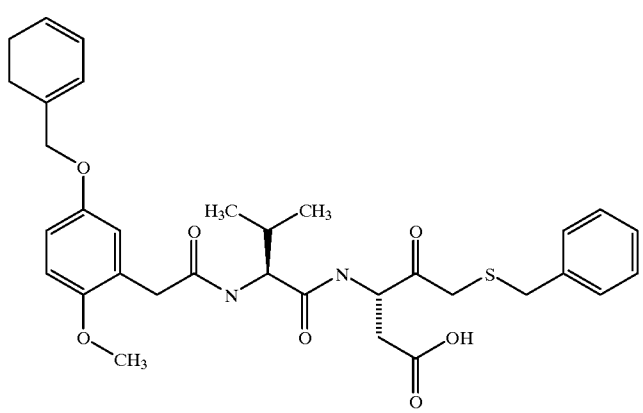 | Chiral |
| 46 | 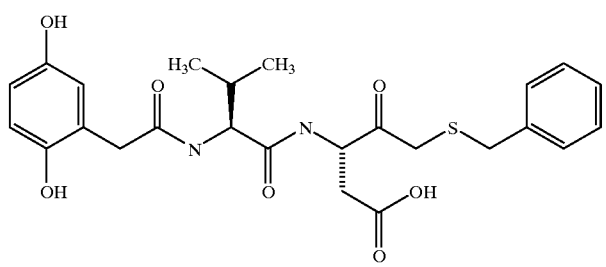 | Chiral |

TABLE I-continued
47 Chiral
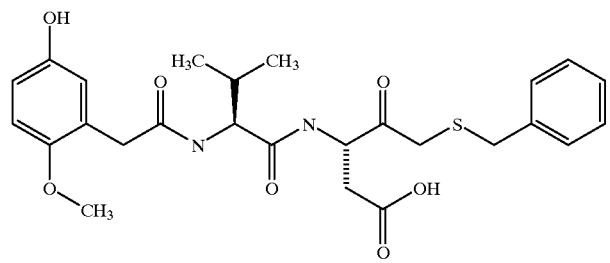
48 Chiral
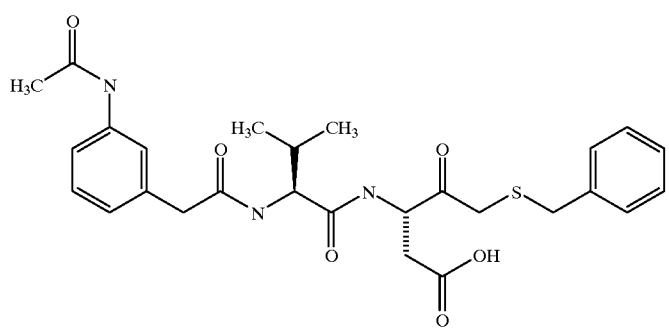
49 Chiral
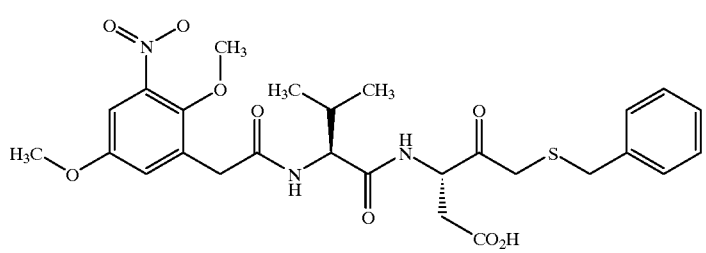
50 Chiral
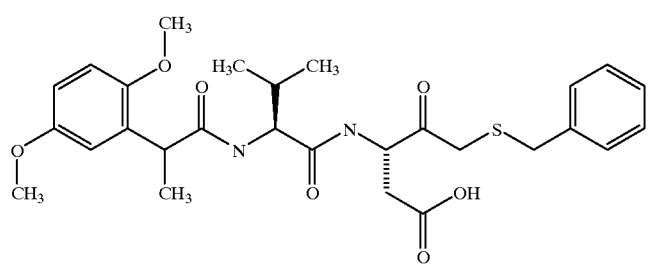
51 Chiral
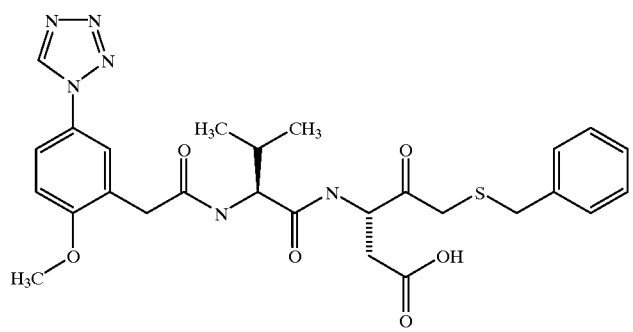

TABLE I-continued
52 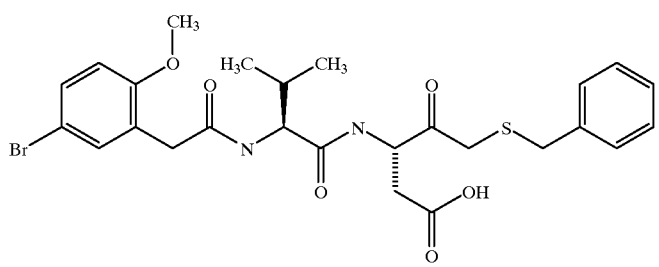 Chiral
53 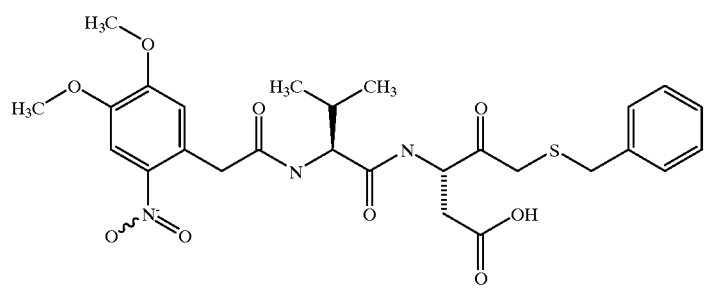 Chiral
54 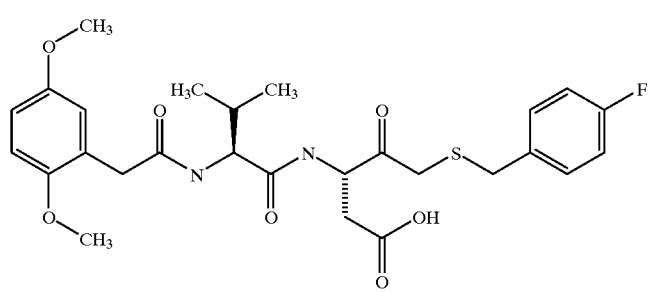 Chiral
55 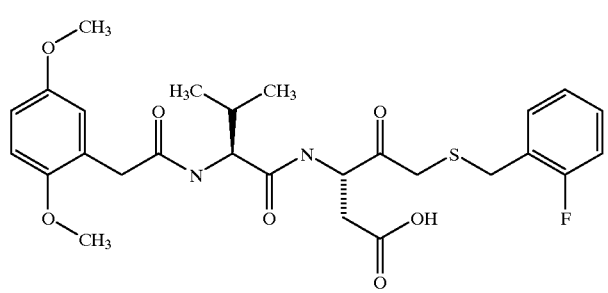 Chiral
56 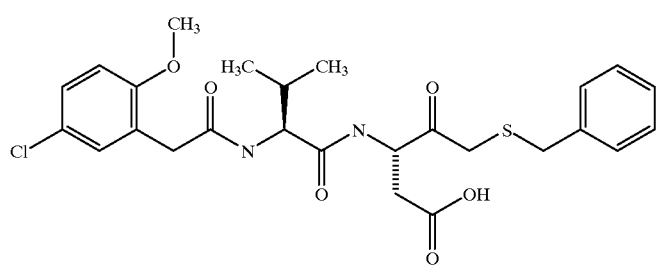 Chiral TABLE I-continued
57 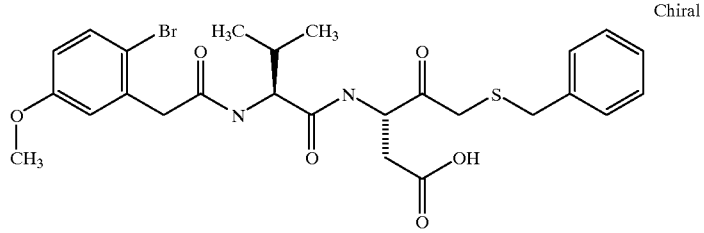 Chiral
58 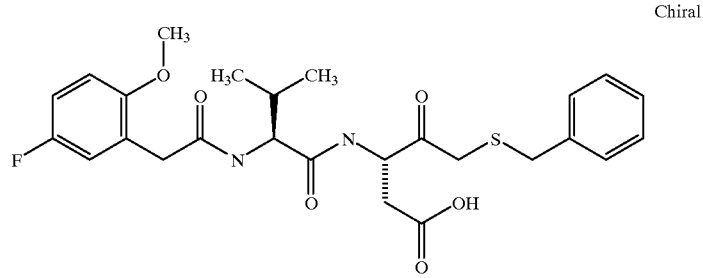 Chiral
59 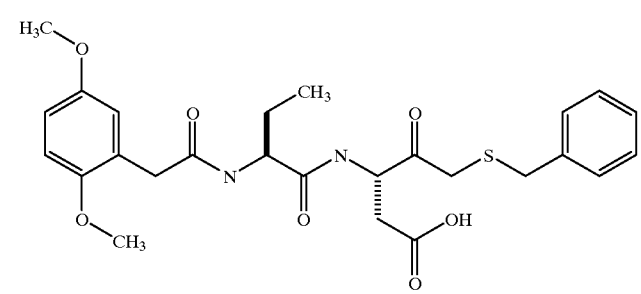 Chiral
60 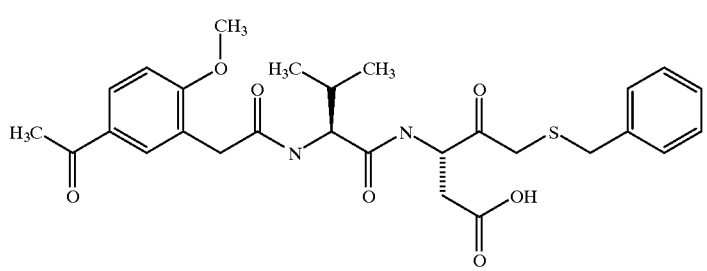 Chiral
61 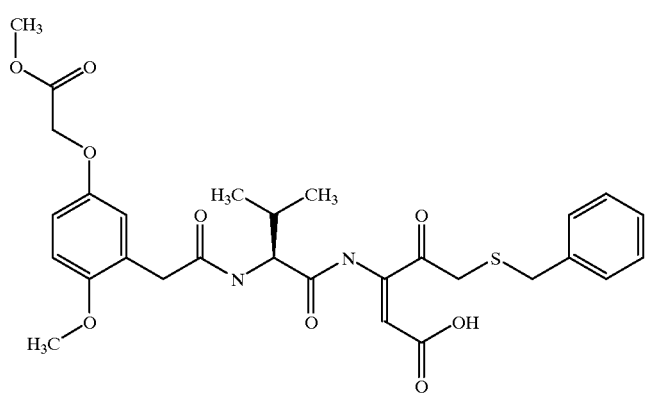 Chiral TABLE I-continued
| 62 | 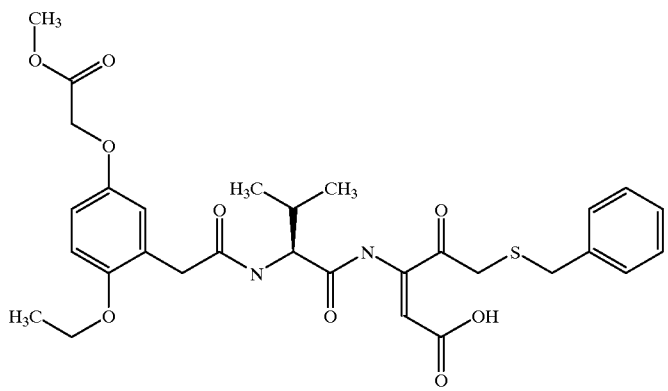 | Chiral |
| 63 | 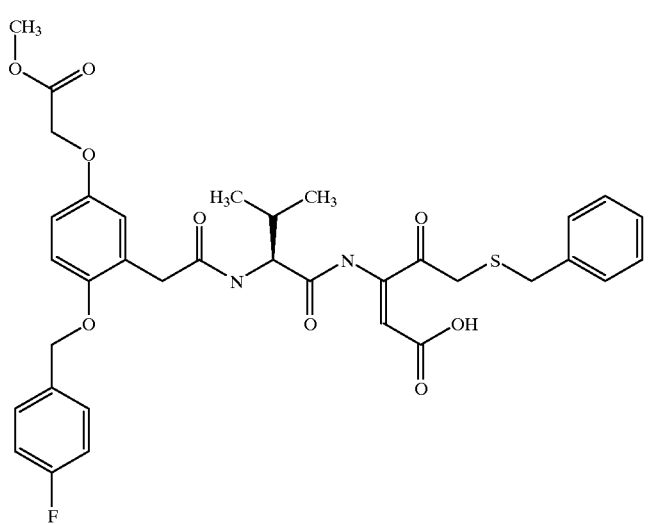 | Chiral |
| 64 | 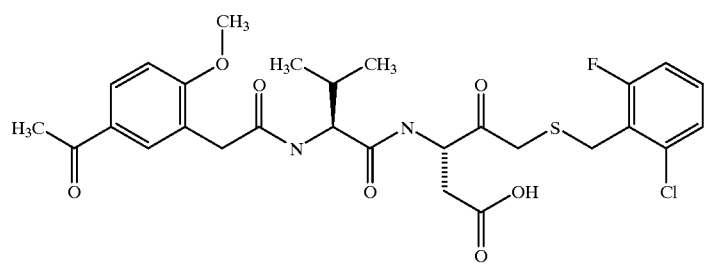 | Chiral |
| 65 | 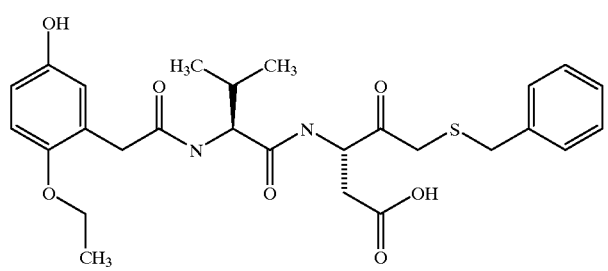 | Chiral |

TABLE I-continued
| 66 | 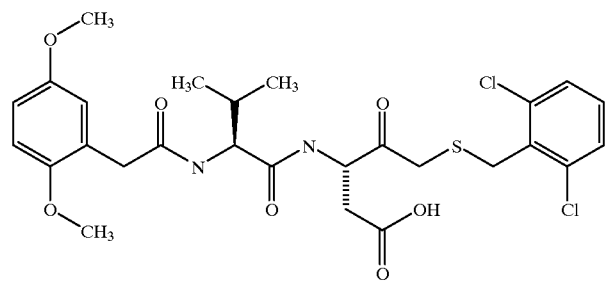 | Chiral |
| --- | --- | --- |
| 67 | 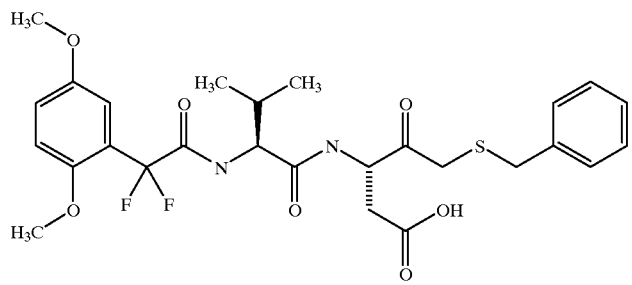 | Chiral |
| 68 | 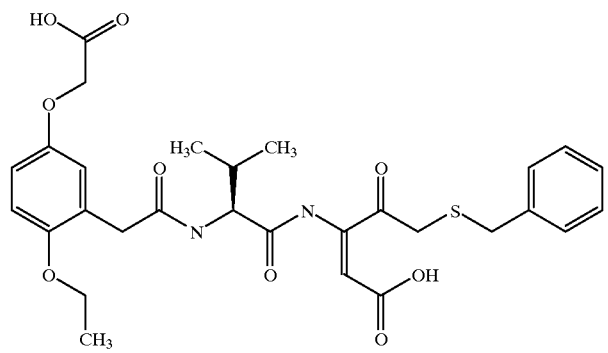 | Chiral |
| 69 | 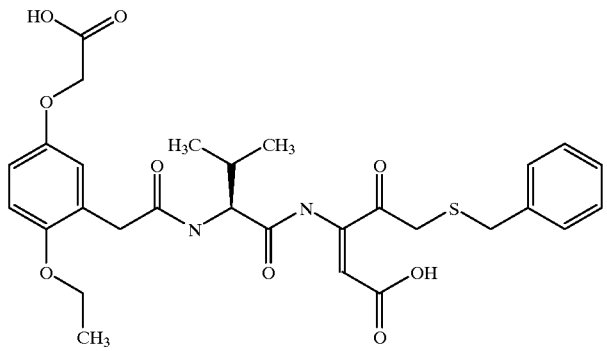 | Chiral |

TABLE I-continued

| 70 | (chemical structure) | Chiral |
| 71 | (chemical structure) | Chiral |
| 72 | (chemical structure) | Chiral |
| 73 | (chemical structure) | Chiral |

TABLE I-continued
| | | |
|---|---|---|
| 74 | 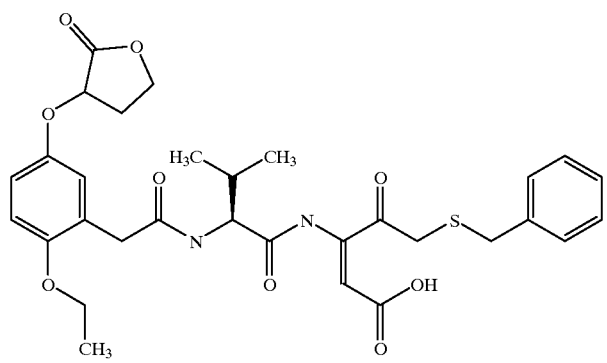 | Chiral |
| 75 | 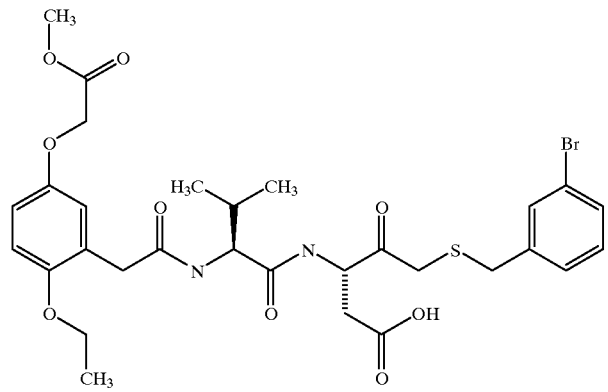 | Chiral |
| 76 | 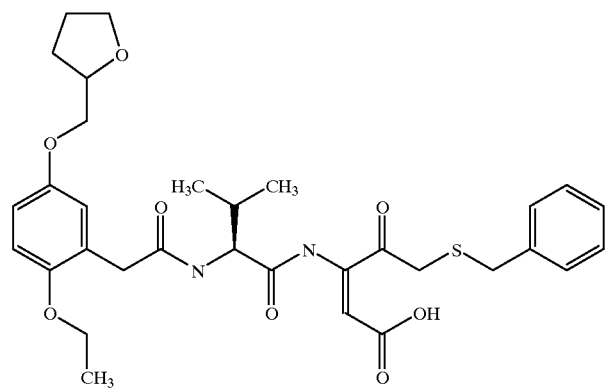 | Chiral |

TABLE I-continued
77 Chiral
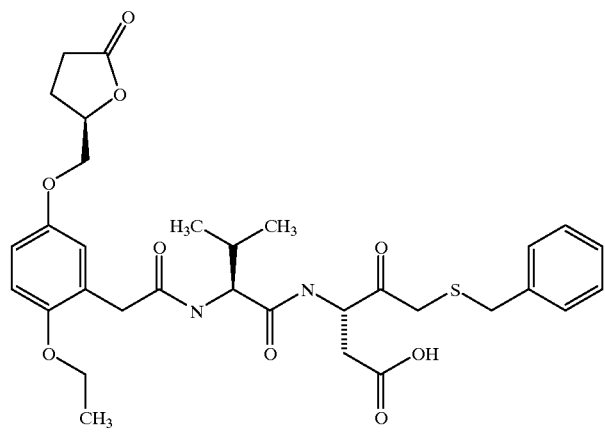
78 Chiral
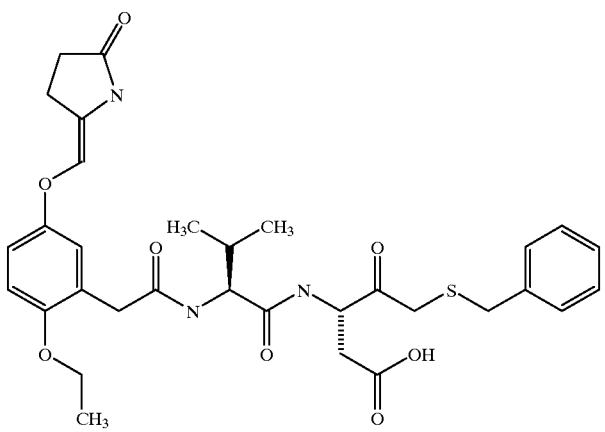
79 Chiral
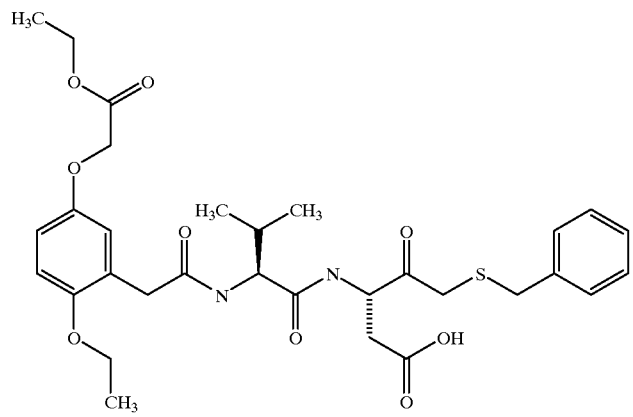

TABLE I-continued
80 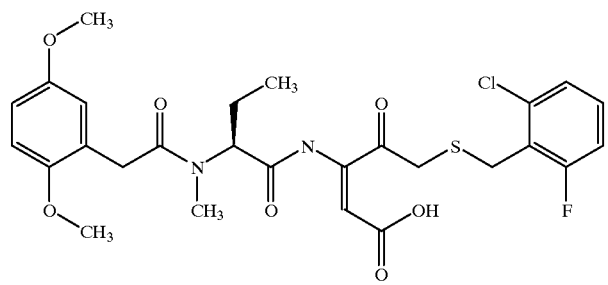 Chiral
81 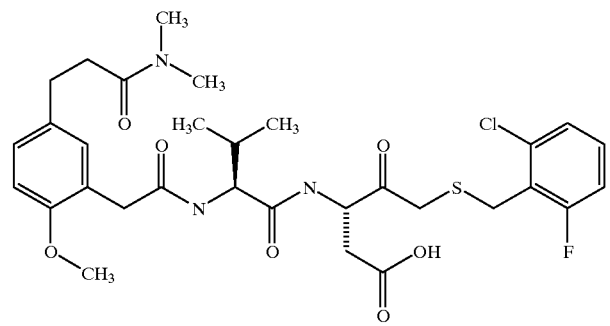 Chiral
82 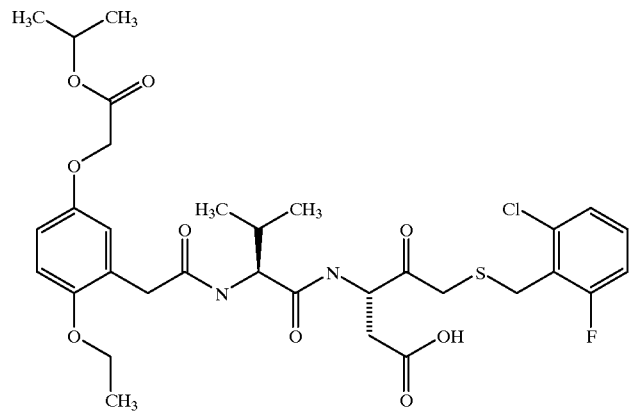 Chiral
83 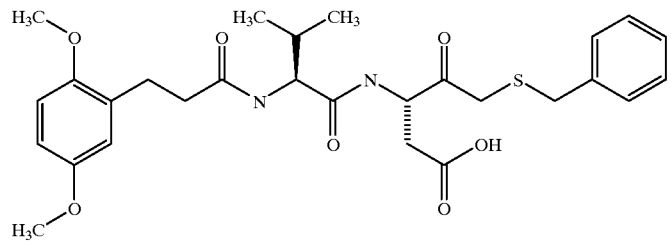 Chiral TABLE I-continued
84 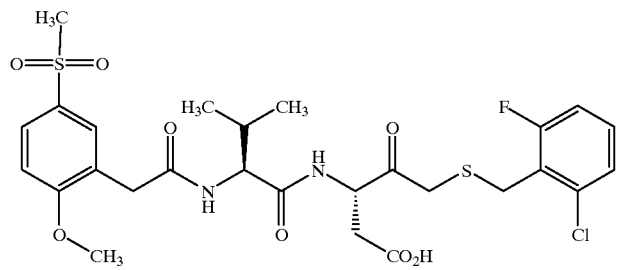 Chiral
85 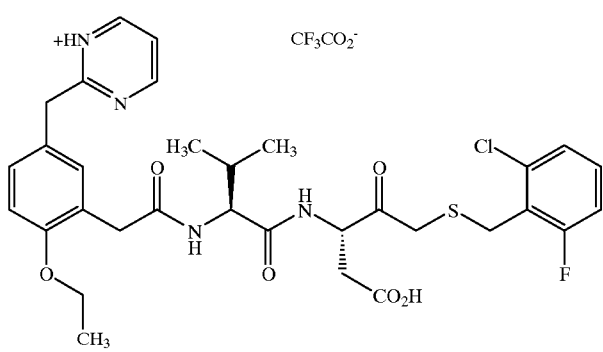 CF₃CO₂⁻ Chiral
86 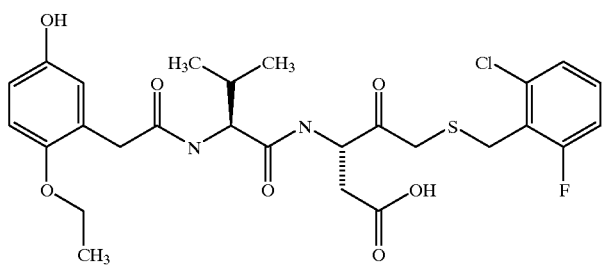 Chiral
87 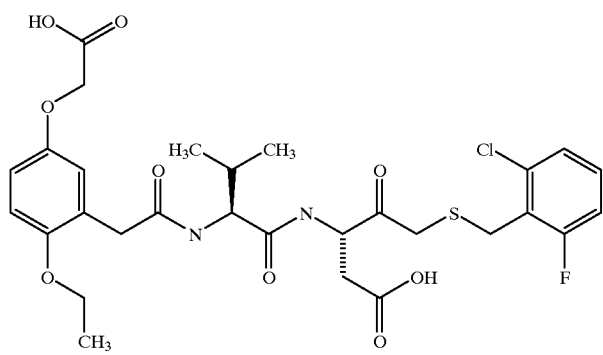 Chiral TABLE I-continued
88 Chiral
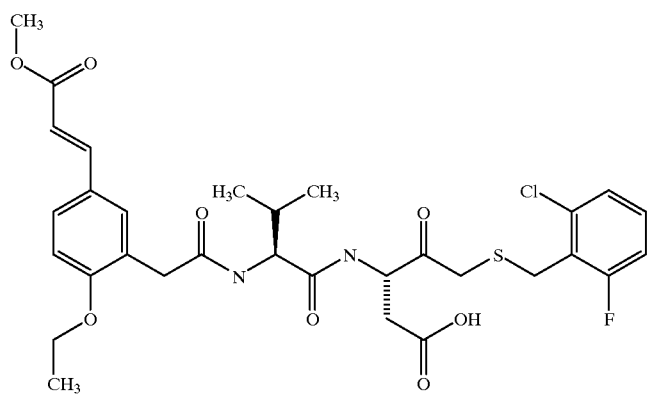
89 Chiral
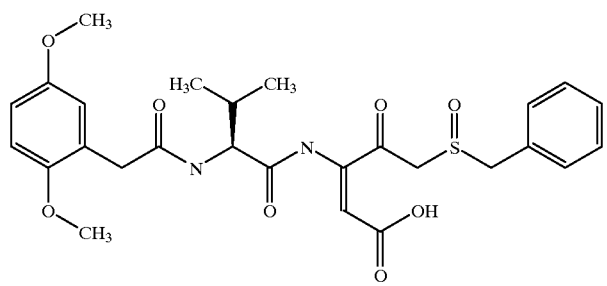
90 Chiral
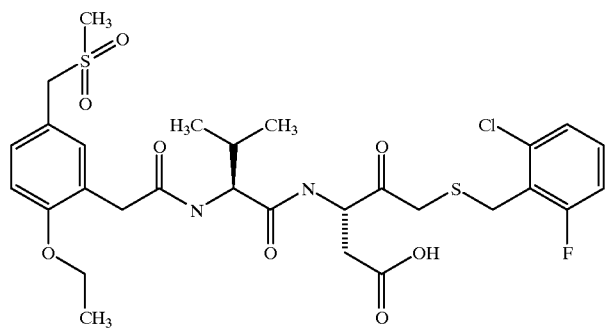
91 Chiral
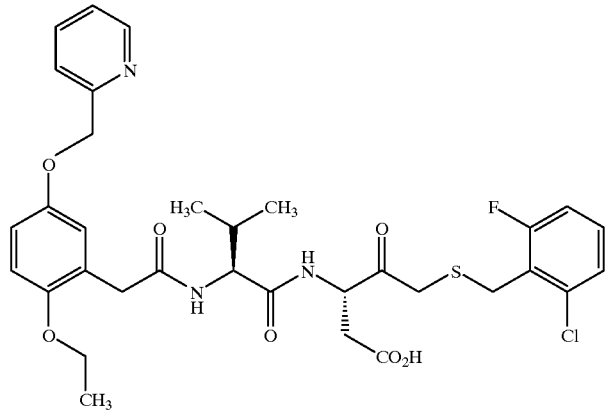

TABLE I-continued
| | | |
|---|---|---|
| 92 | 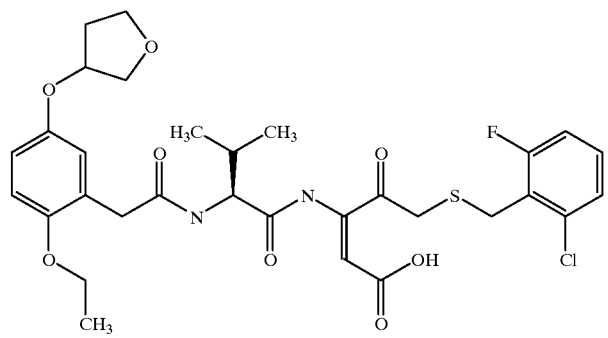 | Chiral |
| 93 | 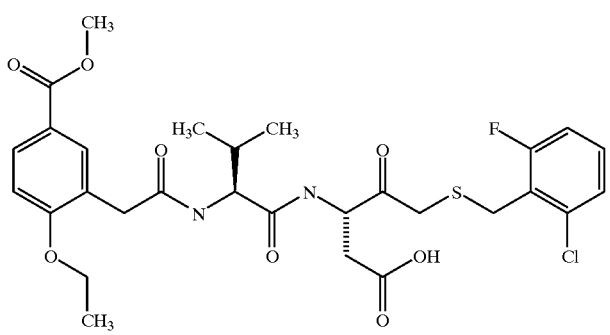 | Chiral |
| 94 | 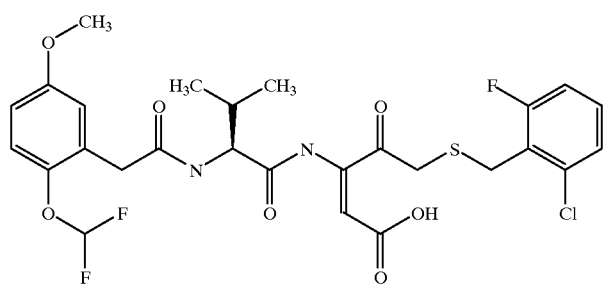 | Chiral |
| 95 | 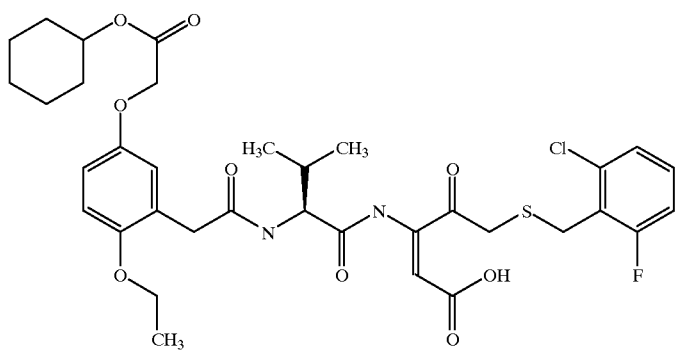 | Chiral |

TABLE I-continued
96 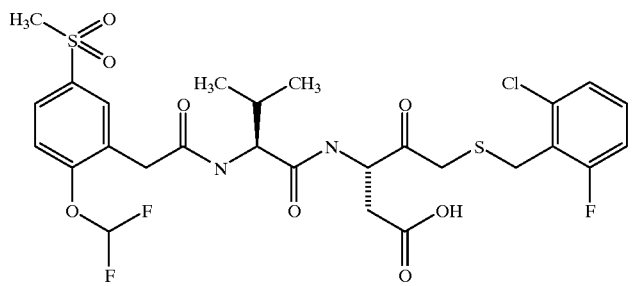 Chiral
97 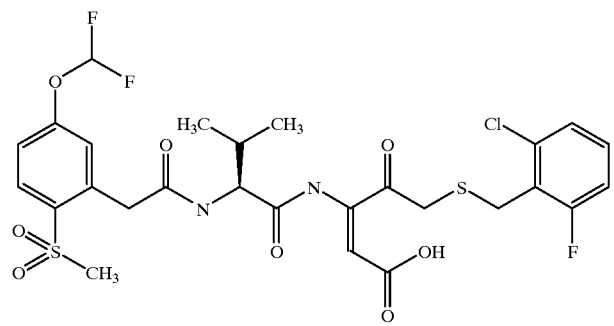 Chiral
98 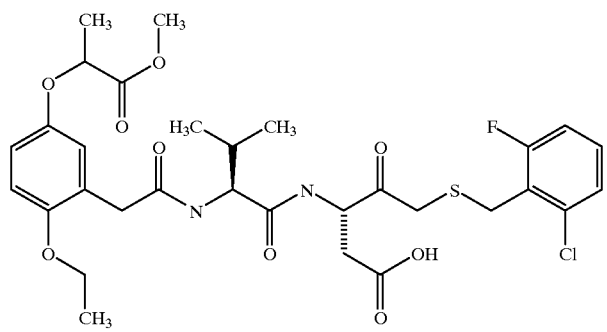 Chiral
99 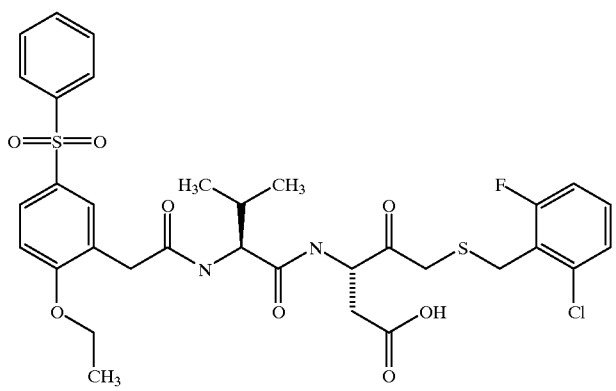 Chiral TABLE I-continued
100 Chiral
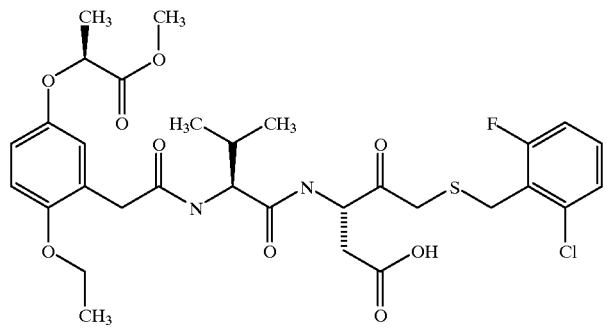
101 Chiral
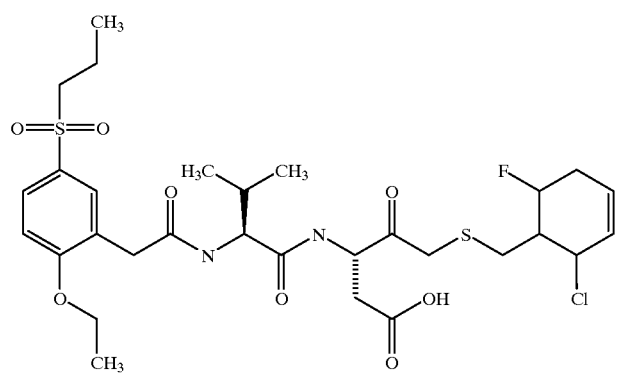
102 Chiral
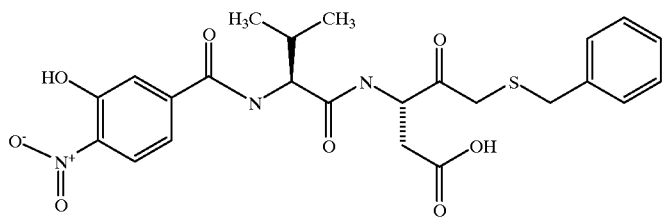
103 Chiral
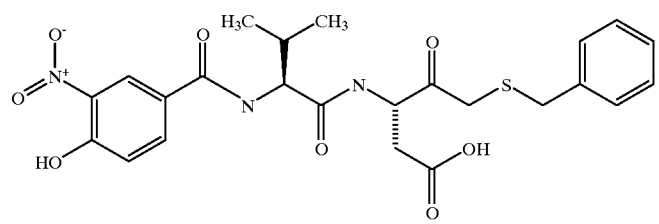

TABLE I-continued
104 Chiral
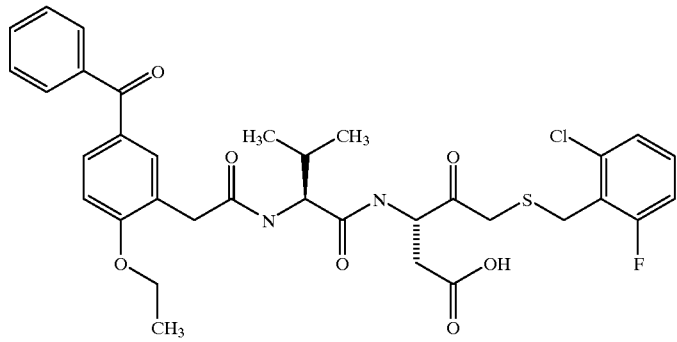
105 Chiral
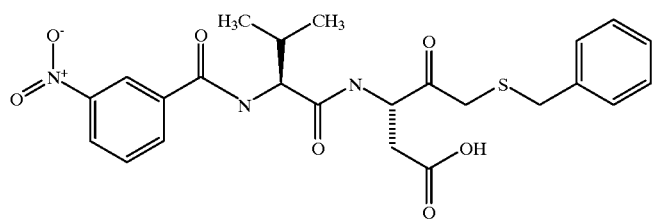
106 Chiral
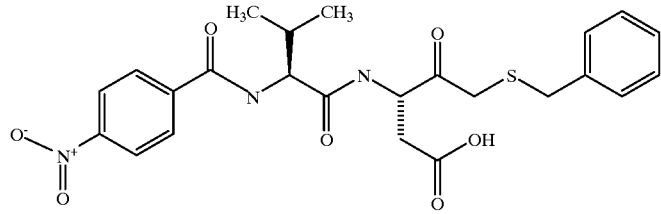
107 Chiral
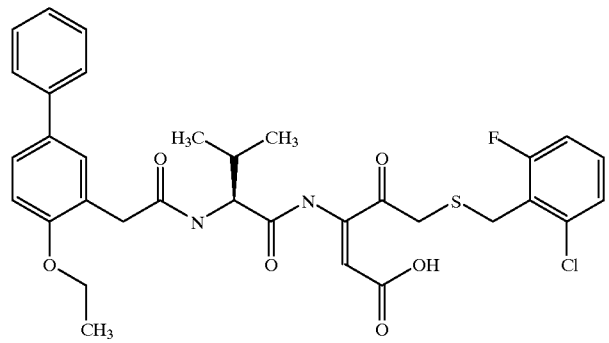
108 Chiral
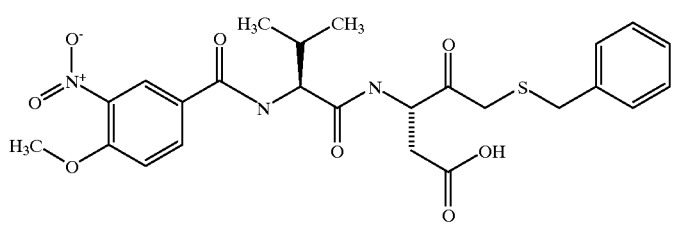

TABLE I-continued
109 Chiral
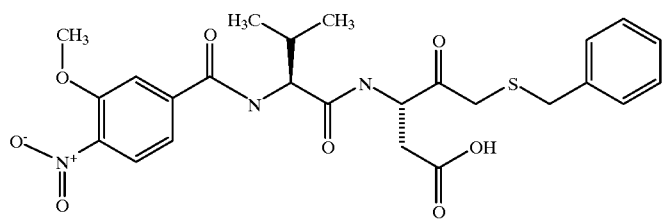
110 Chiral
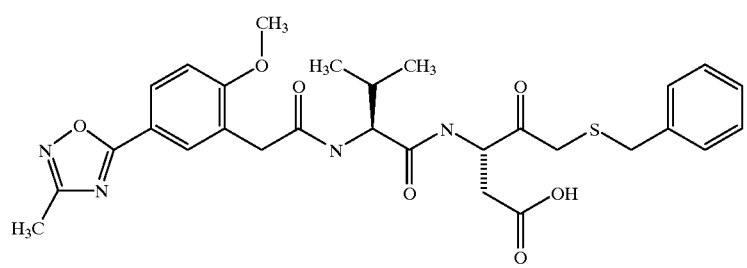
111 Chiral
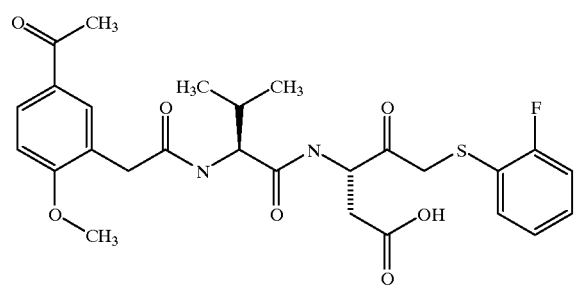
112 Chiral
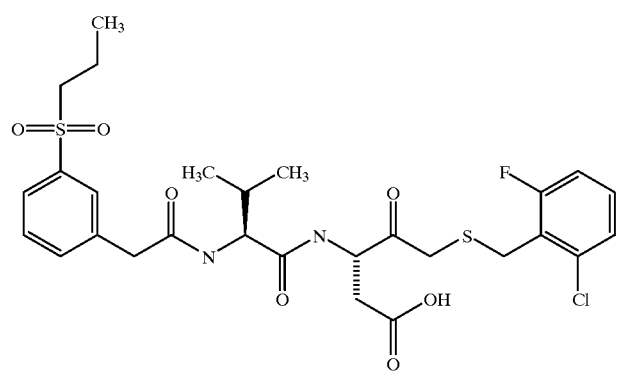
113 Chiral
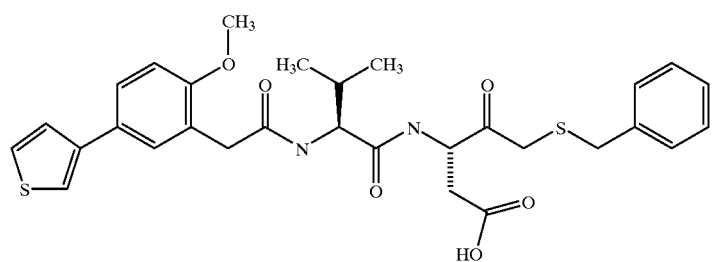

TABLE I-continued
114 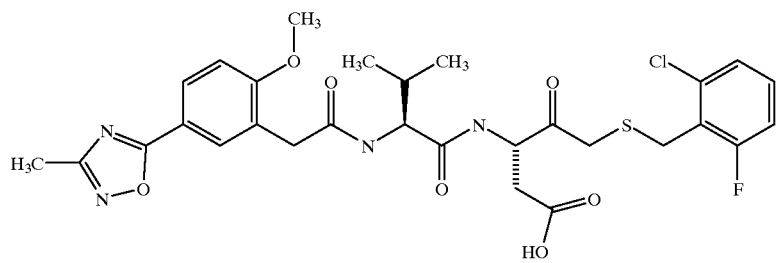 Chiral
115 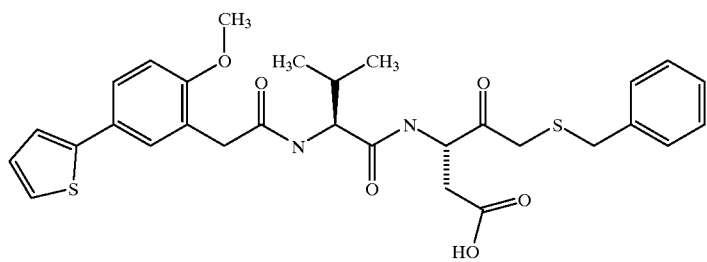 Chiral
116 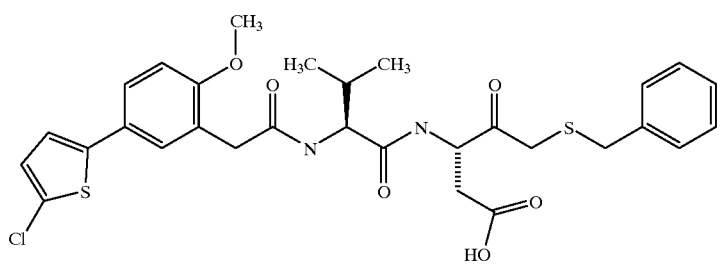
117 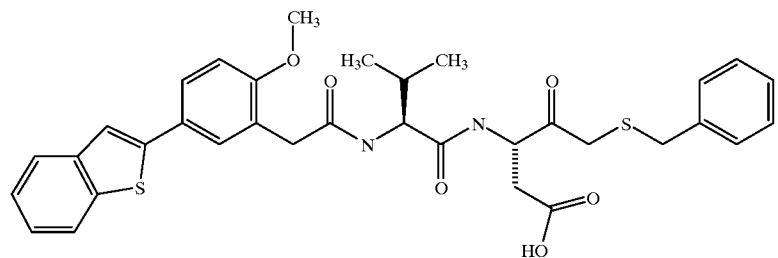 Chiral
118 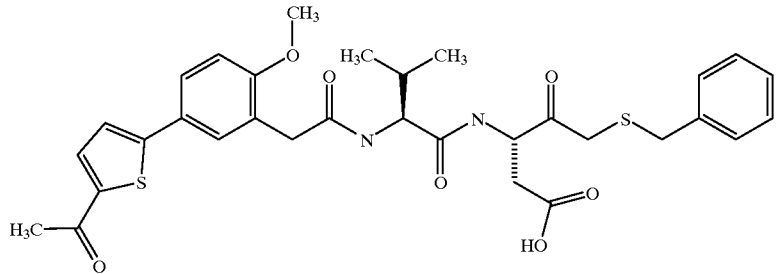 Chiral 174
TABLE I-continued
119 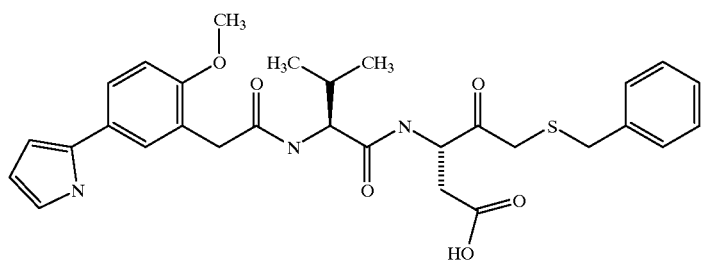 Chiral
120 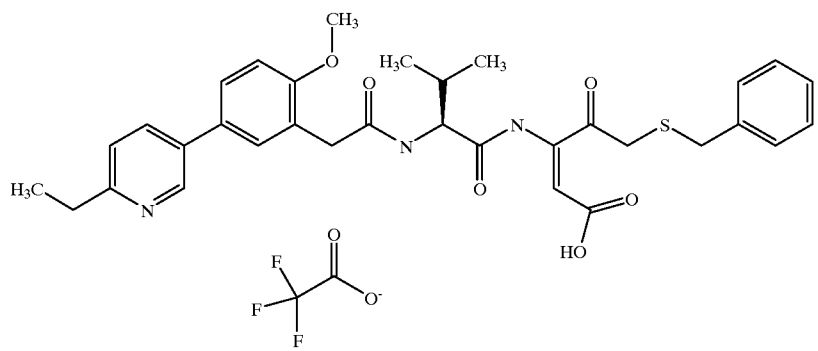 Chiral
121 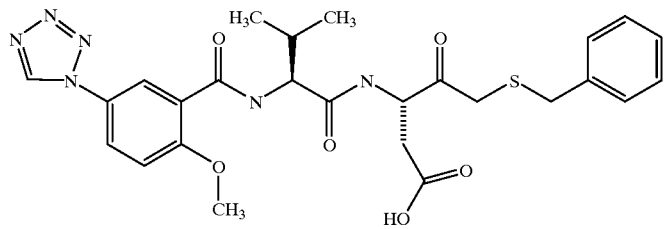 Chiral
122 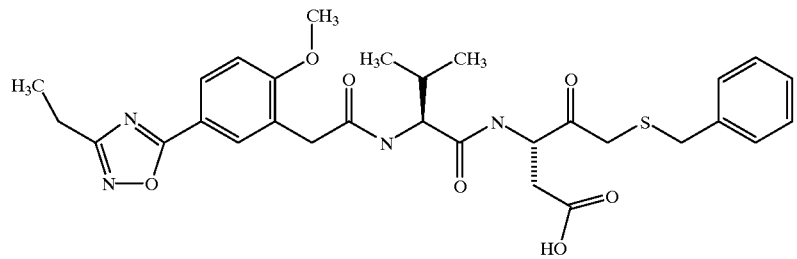 Chiral
123 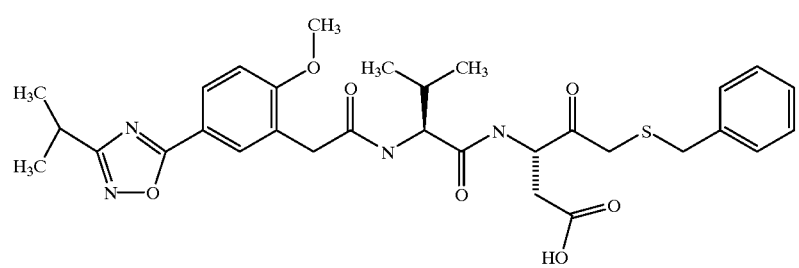

TABLE I-continued
124
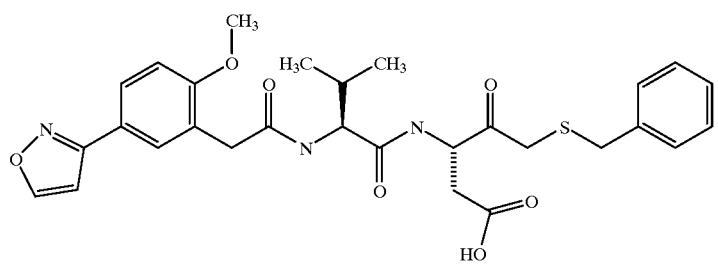
125
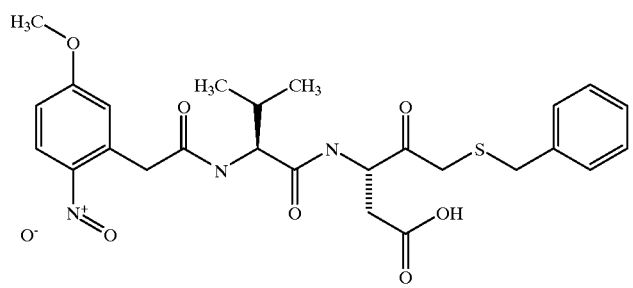
126 Chiral
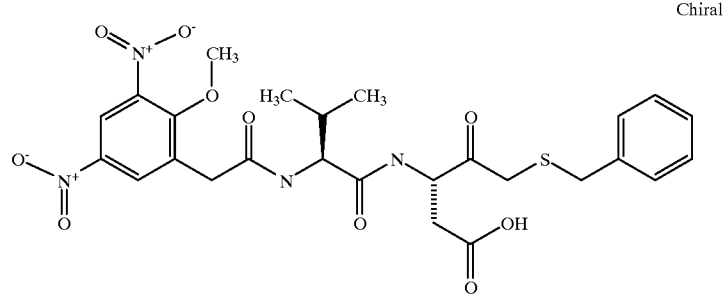
127 Chiral
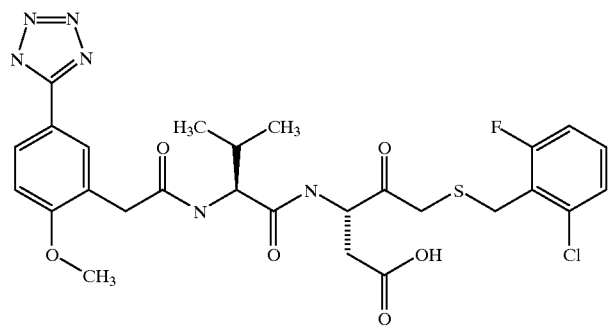
128 Chiral
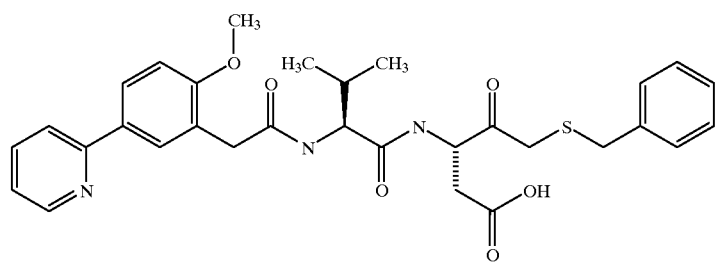

TABLE I-continued

| 129 | (structure) | Chiral |
| 130 | (structure) | Chiral |
| 131 | (structure) | Chiral |
| 132 | (structure) | Chiral |
| 133 | (structure) | Chiral |

TABLE I-continued
| 134 | 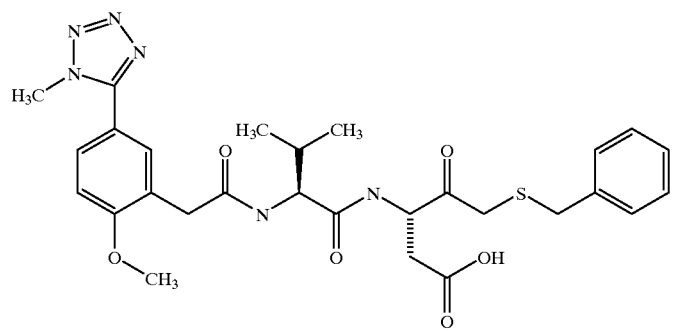 | Chiral |
| 135 | 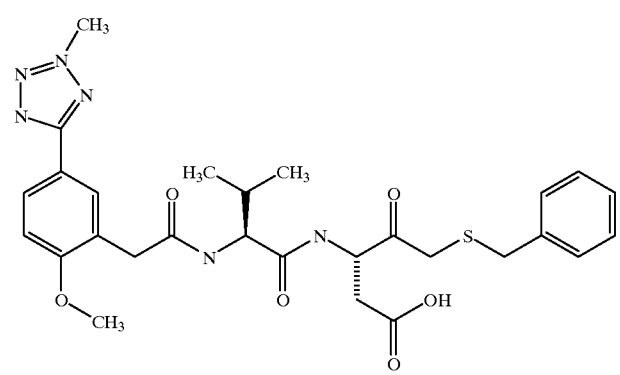 | Chiral |
| 136 | 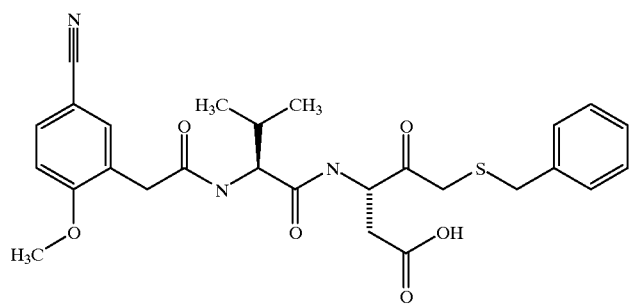 | Chiral |
| 137 | 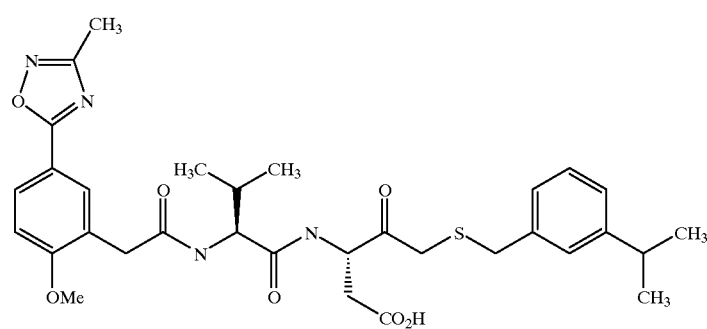 | |

TABLE I-continued
| | |
|---|---|
| 138 | 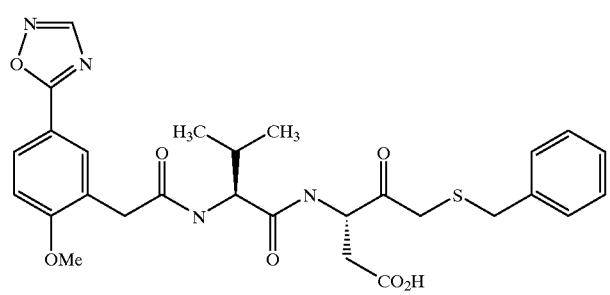 |
| 139 | 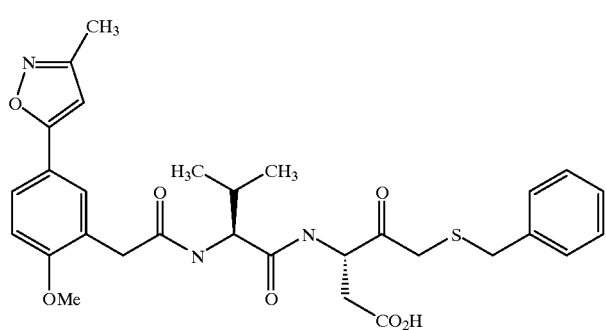 |
| 140 | 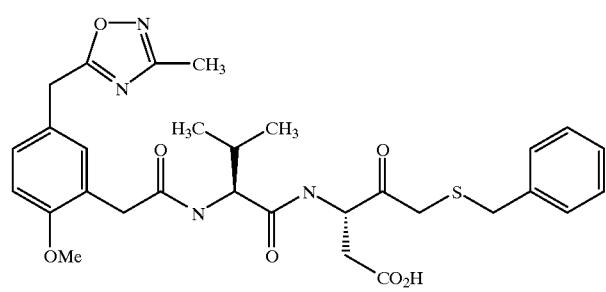 |
| 141 | 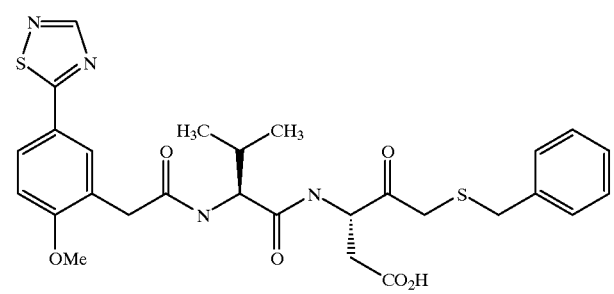 |
| 142 | 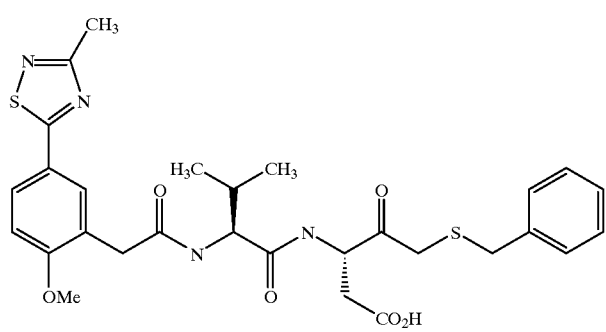 |

TABLE I-continued
143 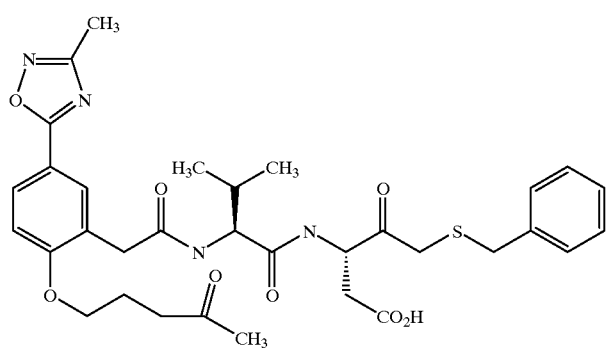
144 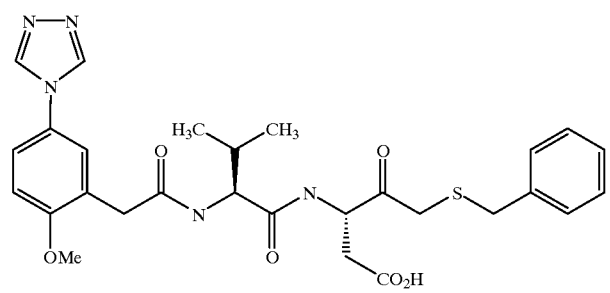
145 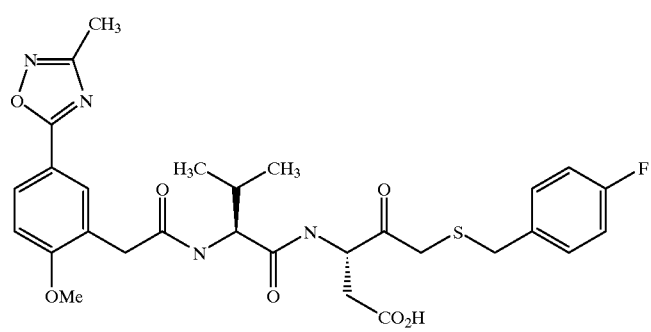
146 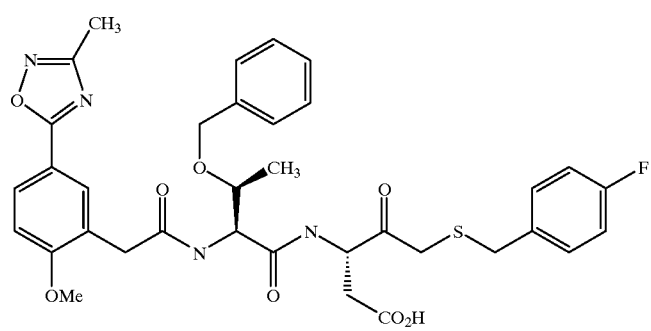

TABLE I-continued
147 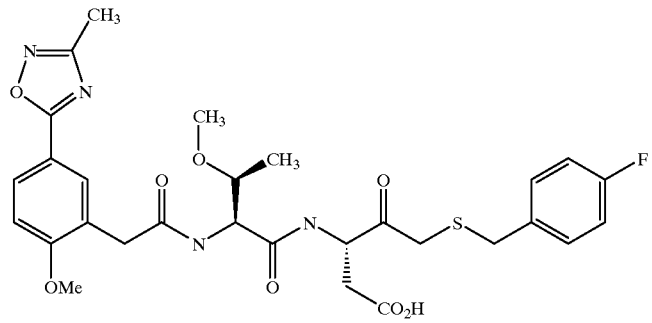
148 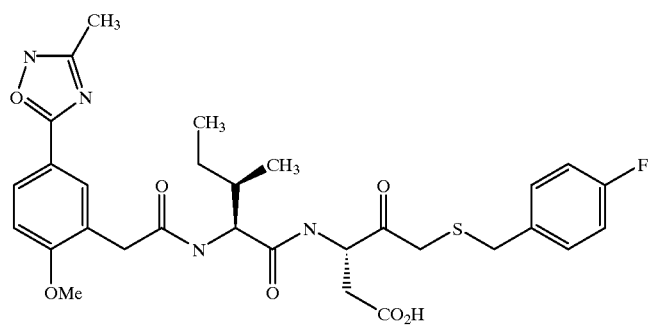
149 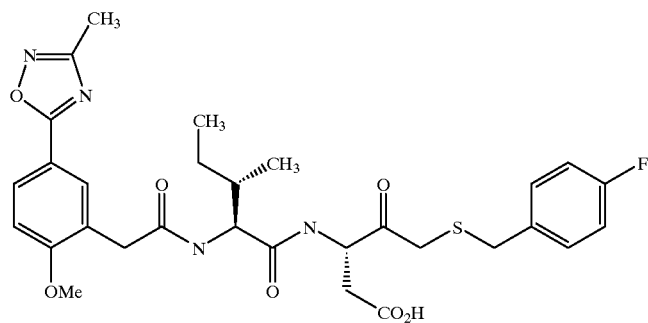
150 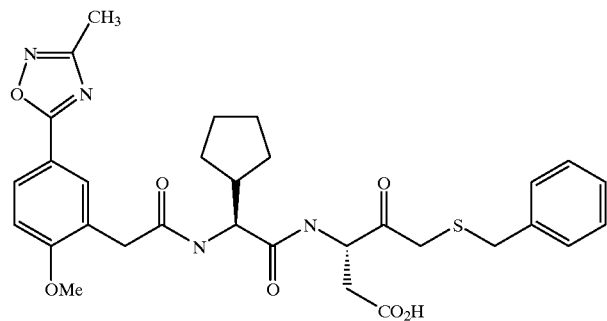

TABLE I-continued

151
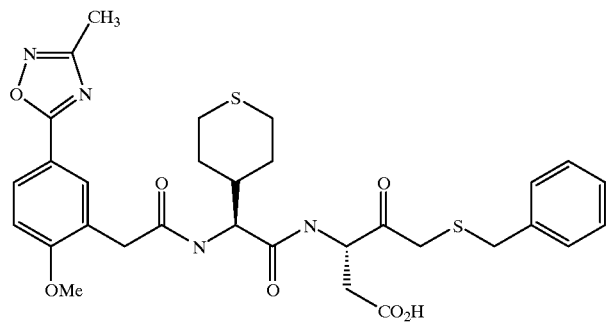

152
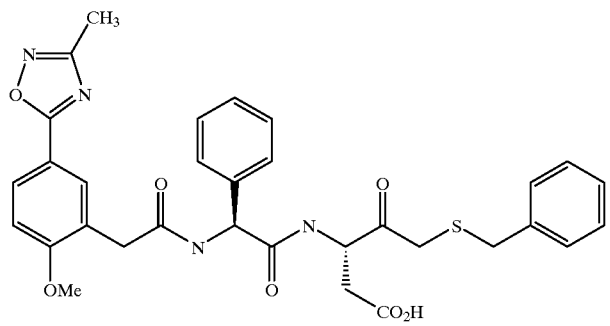

or a salt, hydrate, ester, enantiomer or mixture thereof.

5. A pharmaceutical composition comprised of a compound in accordance with claim 3 in combination with a pharmaceutically acceptable carrier.

6. A method of treating or preventing a caspase-3 mediated disease or condition in a mammalian patient in need of such treatment, comprising administering to said patient a compound in accordance with claim 3 in an amount effective to treat or prevent said caspase-3 mediated disease.

7. A method in accordance with claim 6 wherein the disease or condition is selected from cardiac and cerebral ischemia/ reperfusion injury, spinal cord injury and organ damage during transplantation.

8. A method in accordance with claim 6 wherein the disease or condition is a chronic disorder selected from the group consisting of: a neurodegenerative disease selected from Alzheimer's, polyglutamine-repeat disorders, Down's syndrome, spinal muscular atrophy, multiple sclerosis, immunodeficiency, HIV, diabetes, alopecia and aging.

9. A method in accordance with claim 6 wherein the disease or condition is selected from the group consisting of:
cardiac or cerebral ischemia or reperfusion injury,
type I diabetes,
immune deficiency syndrome or AIDS,
cerebral or spinal cord trauma injury,
organ damage during transplantation,
alopecia,
aging,
Parkinson's disease,
Alzheimer's disease,
Down's syndrome,
spinal muscular atrophy,
multiple sclerosis, and
neurodegenerative disorders.

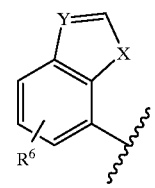

10. A pharmaceutical composition comprised of a compound in accordance with claim 2 in combination with a pharmaceutically acceptable carrier.

11. A method of treating or preventing a caspase-3 mediated disease or condition in a mammalian patient in need of such treatment, comprising administering to said patient a compound in accordance with claim 2 in an amount effective to treat or prevent said caspase-3 mediated disease.

12. A method in accordance with claim 11 wherein the disease or condition is selected from cardiac and cerebral ischemia/reperfusion injury, spinal cord injury and organ damage during transplantation.

13. A method in accordance with claim 11 wherein the disease or condition is a chronic disorder selected from the group consisting of: a neurodegenerative disease selected from Alzheimer's, polyglutamine-repeat disorders, Down's syndrome, spinal muscular atrophy, multiple sclerosis, immunodeficiency, HIV, diabetes, alopecia and aging.

14. A method in accordance with claim 11 wherein the disease or condition is selected from the group consisting of:
cardiac or cerebral ischemia or reperfusion injury, type I diabetes,
immune deficiency syndrome or AIDS,
cerebral or spinal cord trauma injury,
organ damage during transplantation,
alopecia,
aging,
Parkinson's disease,
Alzheimer's disease,
Down's syndrome,
spinal muscular atrophy,
multiple sclerosis, and
neurodegenerative disorders.

\* \* \* \* \*